United States Patent
Harris et al.

(10) Patent No.: US 11,332,749 B2
(45) Date of Patent: May 17, 2022

(54) REAL-TIME REPORTER SYSTEMS FOR MONITORING BASE EDITING

(71) Applicant: Regents of the University of Minnesota, Minneapolis, MN (US)

(72) Inventors: Reuben S. Harris, St. Paul, MN (US); Daniel James Salamango, Crystal, MN (US); Amber Renee St. Martin, Maple Grove, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 323 days.

(21) Appl. No.: 16/035,286

(22) Filed: Jul. 13, 2018

(65) Prior Publication Data

US 2019/0017055 A1    Jan. 17, 2019

Related U.S. Application Data

(60) Provisional application No. 62/532,064, filed on Jul. 13, 2017.

(51) Int. Cl.

| | |
|---|---|
| *C12N 15/00* | (2006.01) |
| *C12N 15/63* | (2006.01) |
| *C12N 15/86* | (2006.01) |
| *C12N 15/10* | (2006.01) |
| *C07K 14/435* | (2006.01) |
| *C07K 16/12* | (2006.01) |
| *C12N 9/78* | (2006.01) |
| *C12N 9/22* | (2006.01) |
| *C07K 16/18* | (2006.01) |
| *C07K 14/00* | (2006.01) |

(52) U.S. Cl.
CPC ...... *C12N 15/635* (2013.01); *C07K 14/43504* (2013.01); *C07K 14/43595* (2013.01); *C07K 16/12* (2013.01); *C07K 16/18* (2013.01); *C12N 9/22* (2013.01); *C12N 9/78* (2013.01); *C12N 15/102* (2013.01); *C12N 15/63* (2013.01); *C12N 15/86* (2013.01); *C07K 14/00* (2013.01); *C07K 2317/24* (2013.01); *C07K 2319/00* (2013.01); *C07K 2319/60* (2013.01); *C12N 2310/20* (2017.05); *C12N 2740/16043* (2013.01)

(58) Field of Classification Search
CPC .......................... C12N 2310/20; C12N 15/635
See application file for complete search history.

(56) References Cited

FOREIGN PATENT DOCUMENTS

WO    WO 2004/067736    8/2004

OTHER PUBLICATIONS

Rabinowitz et al (bioRxiv, published online Jan. 6, 2020) (Year: 2020).*
"Joung Lab gRNA Cloning Protocol," available online at media. addgene.org/data/plasmids/43/43860/43860-attachment_T35tt6ebKxov. pdf, Version 1.2., Oct. 2015.
Boch et al., "Breaking the code of DNA binding specificity of TAL-type III effectors," Science, 326(5959):1509-1512, Dec. 2009.
Bogdanove et al., "TAL effectors: finding plant genes for disease and defense," Curr. Opin. Plant. Biol., 13(4):394-401, Aug. 2010.
Bohn et al., "The ssDNA Mutator APOBEC3A Is Regulated by Cooperative Dimerization," Structure, 23(5):903-911, May 2015.
Burns et al., "APOBEC3B is an enzymatic source of mutation in breast cancer," Nature, 494(7437):366-370, Feb. 2013.
Carpenter et al., "Methylcytosine and normal cytosine deamination by the foreign DNA restriction enzyme APOBEC3A," J. Biol. Chem., 287(41):34801-34808, Oct. 2012.
Chen et al., "Fusion protein linkers: property, design and functionality," Adv. Drug. Deliv. Rev., 65(10):1357-1369, Oct. 2013.
Cho et al., "Targeted genome engineering in human cells with the Cas9 RNA-guided endonuclease," Nat. Biotechnol., 31(3):230-232, Mar. 2013.
Cong et al., "Multiplex genome engineering using CRISPR/Cas systems," Science, 339(6121):819-823, Jan. 2013.
Conticello, "The AID/APOBEC family of nucleic acid mutators," Genome. Biol., 9(6):229, Jun. 2008.
Deltcheva et al., "CRISPR RNA maturation by trans-encoded small RNA and host factor RNase III," Nature, 471(7340):602-607, Mar. 2011.
Di Noia and Neuberger, "Altering the pathway of immunoglobulin hypermutation by inhibiting uracil-DNA glycosylase," Nature, 419(6902):43-48, Sep. 2002.
Dicarlo et al., "Genome engineering in *Saccharomyces cerevisiae* using CRISPR-Cas systems," Nucleic. Acids. Res., 41(7):4336-43, Apr. 2013.
Dong et al., "The crystal structure of Cpf1 in complex with CRISPR RNA," Nature, 532(7600):522-526, Apr. 2016.
Ferretti et al., "Complete genome sequence of an M1 strain of *Streptococcus pyogenes*," Proc. Natl. Acad. Sci. USA., 98(8):4658-4663, Apr. 2001.
GenBank Accession No. AAB02575.1, "neomycin phosphotransferase [Cloning vector pEGFP-N1]," Aug. 22, 2003, 2 pages.
GenBank Accession No. AIC82341.1, "mcherry, partial [Cell-free gateway cloning vector N-term 8xHis mcherry pCellFree_G05]," Feb. 11, 2016, 1 page.
GenBank Accession No. AKP81606.1, "CRISPR-associated endonuclease Cas9/Csn1 [*Streptococcus pyogenes*]," Jul. 9, 2015, 2 pages.
GenBank Accession No. KJ541559.1, "Carpocoris pudicus voucher JSTR00129_0101 cytochrome oxidase subunit I (COI) gene, partial cds; mitochondrial," Jan. 31, 2015, 1 page.
GenBank Accession No. KJ541669.2, "Cell-free gateway cloning vector N-term 8xHis mcherry pCellFree_G05, complete sequence," Feb. 11, 2016, 3 pages.

(Continued)

*Primary Examiner* — Catherine S Hibbert
(74) *Attorney, Agent, or Firm* — Fish & Richardson P.C.

(57) ABSTRACT

Real-time systems for monitoring base editing in living cells, including base editing by APOBEC-Cas9 fusions, is provided herein.

18 Claims, 31 Drawing Sheets
Specification includes a Sequence Listing.

(56) References Cited

OTHER PUBLICATIONS

GenBank Accession No. NC_015683.1, "Corynebacterium ulcerans BR-AD22, complete genome," Mar. 30, 2017, 2 pages.
GenBank Accession No. NC_016782.1, "Corynebacterium diphtheriae 241, complete genome," Mar. 30, 2017, 2 pages.
GenBank Accession No. NC_016786.1, "Corynebacterium diphtheriae HC01, complete genome," Mar. 30, 2017, 2 pages.
GenBank Accession No. NC_017053.1, "*Streptococcus pyogenes* MGAS1882, complete genome," Mar. 22, 2017, 2 pages.
GenBank Accession No. NC_017317.1, "Corynebacterium ulcerans 809, complete genome," Mar. 30, 2017, 2 pages.
GenBank Accession No. NC_017861.1, "Prevotella intermedia 17 chromosome II, complete sequence," Mar. 30, 2017, 2 pages.
GenBank Accession No. NC_018010.1, "Belliella baltica DSM 15883, complete genome," May 18, 2017, 2 pages.
GenBank Accession No. NC_018721.1, "Psychroflexus torquis ATCC 700755, complete genome," May 19, 2017, 2 pages.
GenBank Accession No. NC_021284.1, "Spiroplasma syrphidicola EA-1, complete genome," Apr. 17, 2017, 2 pages.
GenBank Accession No. NC_021314.1, "*Streptococcus iniae* SF1, complete genome," Dec. 18, 2014, 1 page.
GenBank Accession No. NC_021846.1, "Spiroplasma taiwanense CT-1, complete genome," Apr. 17, 2017.
GenBank Accession No. NM_001644.4, "*Homo sapiens* apolipoprotein B mRNA editing enzyme catalytic subunit 1 (APOBEC 1), transcript variant 1, mRNA," Jun. 10, 2017, 3 pagees.
GenBank Accession No. NM_004900.4, "*Homo sapiens* apolipoprotein B mRNA editing enzyme catalytic subunit 3B (APOBEC3B), transcript variant 1, mRNA," Jul. 10, 2017, 4 pages.
GenBank Accession No. NM_014508.2, "*Homo sapiens* apolipoprotein B mRNA editing enzyme catalytic subunit 3C (APOBEC3C), mRNA," May 21, 2017, 3 pages.
GenBank Accession No. NM_020661.3, "*Homo sapiens* activation induced cytidine deaminase (AICDA), transcript variant 1, mRNA," Jul. 10, 2017, 4 pages.
GenBank Accession No. NM_021822.3, "*Homo sapiens* apolipoprotein B mRNA editing enzyme catalytic subunit 3G (APOBEC3G), transcript variant 1, mRNA," Jun. 26, 2017, 4 pages.
GenBank Accession No. NM_145298.5 "*Homo sapiens* apolipoprotein B mRNA editing enzyme catalytic subunit 3F (APOBEC3F), transcript variant 1, mRNA," Jun. 26, 2017, 5 pages.
GenBank Accession No. NM_145699.3, "*Homo sapiens* apolipoprotein B mRNA editing enzyme catalytic subunit 3 A (APOBEC3A), transcript variant 1, mRNA," Jul. 10, 2017, 4 pages.
GenBank Accession No. NM_152426.3, "*Homo sapiens* apolipoprotein B mRNA editing enzyme catalytic subunit 3D (APOBEC3D), mRNA," Jun. 26, 2017, 4 pages.
GenBank Accession No. NM_181773.4, "*Homo sapiens* apolipoprotein B mRNA editing enzyme catalytic subunit 3H (APOBEC3H), transcript variant SV-183, mRNA," Jul. 10, 2017, 3 pages.
GenBank Accession No. NP_004891.4, "DNA dC->dU-editing enzyme APOBEC-3B isoform a [*Homo sapiens*]," Jul. 10, 2017, 3 pages.
GenBank Accession No. NP_472073.1, "hypothetical protein lin2744 [Listeria innocua Clip11262]," Dec. 17, 2014, 2 pages.
GenBank Accession No. NP_663745.1, "DNA dC->dU-editing enzyme APOBEC-3A isoform a [*Homo sapiens*]," Jul. 10, 2017, 3 pages.
GenBank Accession No. U55762.1, "Cloning vector pEGFP-N1, complete sequence, enhanced green fluorescent protein (egfp) and neomycin phosphotransferase genes, complete cds," Aug. 22, 2003, 3 pages.
GenBank Accession No. YP_002342100.1, "hypothetical protein NMA0631 [Neisseria meningitidis Z2491]," Dec. 16, 2014, 2 pages.
GenBank Accession No. YP_002344900.1, "CRISPR-associated protein [*Campylobacter jejuni* subsp. *jejuni* NCTC 11168 = ATCC 700819]," Aug. 3, 2016, 2 pages.

GenBank Accession No. YP_820832.1, "CRISPR-system-like protein [*Streptococcus thermophilus* LMD-9]," Dec. 16, 2014, 2 pages.
Guilinger et al., "Fusion of catalytically inactive Cas9 to FokI nuclease improves the specificity of genome modification," Nat. Biotechnol., 32(6):577-582, Jun. 2014.
Harris and Dudley, "APOBECs and Virus restriction," Virology, 479-480:131-145, May 2015.
Harris et al., "RNA editing enzyme APOBEC1 and some of its homologs can act as DNA mutators," Mol. Cell., 10(5):1247-1253, Nov. 2002.
Hess et al., "Directed evolution using dCas9-targeted somatic hypermutation in mammalian cells," Nat. Methods., 13(12):1036-1042, Dec. 2016.
Hultquist et a;., "Human and rhesus APOBEC3D, APOBEC3F, APOBEC3 G, and APOBEC3H demonstrate a conserved capacity to restrict Vif-deficient HIV-1," J. Virol., 85(21):11220-11234, Nov. 2011.
Hwang et al., "Efficient genome editing in zebrafish using a CRISPR-Cas system," Nat. Biotechnol., 31(3):227-229, Mar. 2013.
Ito et al., "Family-Wide Comparative Analysis of Cytidine and Methylcytidine Deamination by Eleven Human APOBEC Proteins," J. Mol. Biol., 429(12):1787-1799, Jun. 2017.
Jiang et al., "RNA-guided editing of bacterial genomes using CRISPR-Cas systems," Nat. Biotechnol., 31(3):233-239, Mar. 2013.
Jinek et al., "A programmable dual-RNA-guided DNA endonuclease in adaptive bacterial immunity," Science, 337(6096):816-821, Aug. 2012.
Kim et al., "Genome-wide target specificities of CRISPR RNA-guided programmable deaminases," Nat. Biotechnol., 35(5):475-480, May 2017.
Kim et al., "Highly efficient RNA-guided base editing in mouse embryos," Nat. Biotechnol., 35(5):435-437, May 2017.
Kim et al., "Increasing the genome-targeting scope and precision of base editing with engineered Cas9-cytidine deaminase fusions," Nat. Biotechnol., 35(4):371-376, Apr. 2017.
Komor et al., "Programmable editing of a target base in genomic DNA without double-stranded DNA cleavage," Nature, 533(7603):420-424, May 2016.
Kouno et al., "Crystal structure of APOBEC3A bound to single-stranded DNA reveals structural basis for cytidine deamination and specificity," Nat. Commun., 8:15024, Apr. 2017.
Kuscu and Adli, "CRISPR-Cas9-AID base editor is a powerful gain-of-function screening tool," Nat. Methods., 13(12):983-984, Nov. 2016.
Li et al., "Generation of Targeted Point Mutations in Rice by a Modified CRISPR/Cas9 System," Mol. Plant., 10(3):526-529, Mar. 2017.
Lu and Zhu, "Precise Editing of a Target Base in the Rice Genome Using a Modified CRISPR/Cas9 System," Mol. Plant., 10(3):523-525, Mar. 2017.
Makarova et al., "Evolution and classification of the CRISPR-Cas systems," Nat. Rev. Microbiol., 9(6):467-477, Jun. 2011.
Mali et al., "CAS9 transcriptional activators for target specificity screening and paired nickases for cooperative genome engineering," Nat. Biotechnol., 31(9):833-838, Sep. 2013.
Mali et al., "RNA-guided human genome engineering via Cas9," Science, 339(6121):823-826, Feb. 2013.
Mol et al., "Crystal structure of human uracil-DNA glycosylase in complex with a protein inhibitor: protein mimicry of DNA," Cell, 82(5):701-708, Sep. 1995.
Nabel et al., "The curious chemical biology of cytosine: deamination, methylation, and oxidation as modulators of genomic potential," ACS. Chem. Biol., 7(1):20-30, Jan. 2012.
Nishida et al., "Targeted nucleotide editing using hybrid prokaryotic and vertebrate adaptive immune systems," Science, 353(6305), Sep. 2016.
Pham et al., "Activation-induced deoxycytidine deaminase: Structural basis for favoring WRC hot motif specificities unique among APOBEC family members," DNA Repair (Amst)., 54:8-12, Jun. 2017.
Porteus and Baltimore, "Chimeric nucleases stimulate gene targeting in human cells," Science, 300(5620):763, May 2003.

(56) References Cited

OTHER PUBLICATIONS

Porteus, "Plant biotechnology: Zinc fingers on target," Nature, 459(7245):337-338, May 2009.

Qi et al., "Repurposing CRISPR as an RNA-guided platform for sequence-specific control of gene expression," Cell, 152(5):1173-83, Feb. 2013.

Rees et al., "Improving the DNA specificity and applicability of base editing through protein engineering and protein delivery," Nat. Commun., 8:15790, Jun. 2017.

Shi et al., "Crystal Structure of the DNA Deaminase APOBEC3B Catalytic Domain," J. Biol. Chem., 290(47):28120-28130, Nov. 2015,.

Shi et al., "Structural basis for targeted DNA cytosine deamination and mutagenesis by APOBEC3A and APOBEC3B," Nat. Struct. Mol. Biol., 24(2):131-139, Feb. 2017.

Shimatani et al., "Targeted base editing in rice and tomato using a CRISPR-Cas9 cytidine deaminase fusion," Nat. Biotechnol., 35(5):441-443, May 2017.

Shu et al., "Novel chromophores and buried charges control color in mFruits," Biochemistry, 45(32):9639-9647, Aug. 2006.

Stenglein et al., "APOBEC3 proteins mediate the clearance of foreign DNA from human cells," Nat. Struct. Mol. Biol., 17(2):222-229, Feb. 2010.

Yamano et al., "Crystal Structure of Cpf1 in Complex with Guide RNA and Target DNA," Cell, 165(4):949-962, May 2016.

Zong et al., "Precise base editing in rice, wheat and maize with a Cas9-cytidine deaminase fusion," Nat. Biotechnol., 35(5):438-440, May 2017.

Banno et al., "Deaminase-mediated multiplex genome editing in *Escherichia coli*," Nat. Microbiology, 3(4):423-429, Feb. 5, 2018.

Komor et al., "Improved base excision repair inhibition and bacteriophage Mu Gam protein yields C:G-to-T:A base editors with higher efficiency and product purity," Sci. Advances, 3(8):eaao4774, Aug. 30, 2017, 10 pages.

Krokan et al., "Uracil in DNA—occurrence, consequences and repair," Oncogene, 21(58):8935-8948, Dec. 16, 2002.

Lei et al., "APOBEC3 induces mutations during repair of CRISPR-Cas9-generated DNA breaks," Nat. Struct. Mol. Biology, 25(1):45-52, Dec. 11, 2017.

Lindahl et al., "Quality control by DNA repair," Science, 286(5446): 1897-1905, Dec. 1999.

Severi et al., "Analysis of reptilian APOBEC1 suggests that RNA editing may not be its ancestral function," Mol. Biol. Evolution, 28(3):1 125-1129, Mar. 2011.

Simon et al., "Intrinsic host restrictions to HIV-1 and mechanisms of viral escape," Nat. Immunology, 16(6):546-553, Jun. 2015.

St. Martin et al., "A fluorescent reporter for quantification and enrichment of DNA editing by APOBEC-Cas9 or cleavage by Cas9 in living cells," Nucleic Acids Research, 46(14):e84, Aug. 21, 2018, 10 pages.

Wang et al., "Enhanced base editing by co-expression of free uracil DNA glycosvlase inhibitor," Cell Research, 27(10): 1289-1292, Aug. 29, 2017.

* cited by examiner

| Consensus | PAM  *PmlI* TCCAGGTGCTGCAGAAGGGATTCCATG | Edited Sequences | SEQ ID: 80 |
|---|---|---|---|
| A3A Edited | TCCAGG█GCTGCAGAAGGGATTCCATG<br>TCCAGGTG--------GCATTCCATG<br>TCCAGGTGC█TGCAAGGGATTCCATG | 11<br>5<br>1 | 81<br>82<br>83 |
| A3Bctd Edited | TCCAGG█GCTGCAGAAGGGATTCCATG<br>TCCAGGTG--------GCATTCCATG<br>T----------GAAGGGATTCCATG<br>TCCAGGTGCTGC█CAAGGGATTCCATG<br>TCC█G█TGC██AAGGA█TCCGTG | 4<br>3<br>1<br>1<br>1 | 81<br>82<br>84<br>85<br>86 |
| BE3 Edited | TCCAGGTGCT█CAGAAGGGATTCCATG<br>T----------GAAGGGATTCCATG<br>TCCAGG█GCTGCAGAAGGGATTCCATG | 1<br>1<br>1 | 87<br>84<br>81 |

FIG. 6A

```
      Thr54 Lys55 Gly56 Gly57 Pro58 Leu59 Pro60 Phe61 Ala62 Trp63 Asp64  (SEQ ID NO:88)
L59   ACCAAGGGTGGCCCCCTGCCCCTTCGCCTGGGAC                                  (SEQ ID NO:89)

Thr54 Lys55 Gly56 Gly57 Pro58 Ser59 Pro60 Phe61 Ala62 Trp63 Asp64  (SEQ ID NO:90)
S59   ACCAAGGGTGGCCCCTCACCCCTTCGCCTGGGAC                                  (SEQ ID NO:91)

Thr54 Lys55 Gly56 Gly57 Pro58 Ser59 Pro60 Phe61 Ala62 Trp63         (SEQ ID NO:92)
ACE   ACCAAGGGTGGCCCCTCACCCCTTCGCCTGGG (+43bp) AC                        (SEQ ID NO:93)
```

FIG. 9C

SEQUENCE LISTING

<160> NUMBER OF SEQ ID NOS: 125

<210> SEQ ID NO 1
<211> LENGTH: 699
<212> TYPE: DNA
<213> ORGANISM: Artificial Sequence
<220> FEATURE:
<223> OTHER INFORMATION: synthetic oligonucleotide

<400> SEQUENCE: 1

```
aagggcgagg aggataacat ggccatcatc aaggagttca tgcgcttcaa ggtgcacatg      60
gagggctccg tgaacggcca cgagttcgag atcgagggcg agggcgaggg ccgcccctac     120
gagggcaccc agaccgccaa gctgaaggtg accaagggtg ccccctgcc cttcgcctgg     180
gacatcctgt cccctcagtt catgtacggc tccaaggcct acgtgaagca ccccgccgac     240
atccccgact acttgaagct gtccttcccc gagggcttca gtgggagcg cgtgatgaac     300
ttcgaggacg gcggcgtggt gaccgtgacc caggactcct ccctgcagga cggcgagttc     360
atctacaagg tgaagctgcg cggcaccaac ttcccctccg acggcccgt aatgcagaag     420
aagactatgg gctgggaggc ctcctccgag cggatgtacc ccgaggacgg cgccctgaag     480
ggcgagatca gcagaggct gaagctgaag gacggcggcc actacgacgc tgaggtcaag     540
accacctaca aggccaagaa gcccgtgcag ctgcccggcg cctacaacgt caacatcaag     600
ttggacatca cctcccacaa cgaggactac accatcgtgg aacagtacga acgcgccgag     660
ggccgccact ccaccggcgg catggacgag ctgtacaag                            699
```

<210> SEQ ID NO 2
<211> LENGTH: 233
<212> TYPE: PRT
<213> ORGANISM: Artificial Sequence
<220> FEATURE:
<223> OTHER INFORMATION: synthetic polypeptide

<400> SEQUENCE: 2

```
Lys Gly Glu Glu Asp Asn Met Ala Ile Ile Lys Glu Phe Met Arg Phe
1               5                   10                  15

Lys Val His Met Glu Gly Ser Val Asn Gly His Glu Phe Glu Ile Glu
            20                  25                  30

Gly Glu Gly Glu Gly Arg Pro Tyr Glu Gly Thr Gln Thr Ala Lys Leu
        35                  40                  45

Lys Val Thr Lys Gly Gly Pro Leu Pro Phe Ala Trp Asp Ile Leu Ser
    50                  55                  60

Pro Gln Phe Met Tyr Gly Ser Lys Ala Tyr Val Lys His Pro Ala Asp
65                  70                  75                  80

Ile Pro Asp Tyr Leu Lys Leu Ser Phe Pro Glu Gly Phe Lys Trp Glu
                85                  90                  95

Arg Val Met Asn Phe Glu Asp Gly Gly Val Val Thr Val Thr Gln Asp
            100                 105                 110

Ser Ser Leu Gln Asp Gly Glu Phe Ile Tyr Lys Val Lys Leu Arg Gly
        115                 120                 125

Thr Asn Phe Pro Ser Asp Gly Pro Val Met Gln Lys Lys Thr Met Gly
    130                 135                 140

Trp Glu Ala Ser Ser Glu Arg Met Tyr Pro Glu Asp Gly Ala Leu Lys
145                 150                 155                 160

Gly Glu Ile Lys Gln Arg Leu Lys Leu Lys Asp Gly Gly His Tyr Asp
                165                 170                 175
```

```
Ala Glu Val Lys Thr Thr Tyr Lys Ala Lys Lys Pro Val Gln Leu Pro
            180                 185                 190

Gly Ala Tyr Asn Val Asn Ile Lys Leu Asp Ile Thr Ser His Asn Glu
        195                 200                 205

Asp Tyr Thr Ile Val Glu Gln Tyr Glu Arg Ala Glu Gly Arg His Ser
    210                 215                 220

Thr Gly Gly Met Asp Glu Leu Tyr Lys
225                 230
```

```
<210> SEQ ID NO 3
<211> LENGTH: 720
<212> TYPE: DNA
<213> ORGANISM: Artificial Sequence
<220> FEATURE:
<223> OTHER INFORMATION: synthetic oligonucleotide

<400> SEQUENCE: 3
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720
```

```
<210> SEQ ID NO 4
<211> LENGTH: 239
<212> TYPE: PRT
<213> ORGANISM: Artificial Sequence
<220> FEATURE:
<223> OTHER INFORMATION: synthetic polypeptide

<400> SEQUENCE: 4

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125
```

```
Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235

<210> SEQ ID NO 5
<211> LENGTH: 1444
<212> TYPE: DNA
<213> ORGANISM: Homo sapiens

<400> SEQUENCE: 5
ggagaagggg tggggcaggg tatcgctgac tcagcagctt ccaggttgct ctgatgatat      60
attaaggctc ctgaatccta agagaatgtt ggtgaagatc ttaacaccac gccttgagca     120
agtcgcaaga gcgggaggac acagaccagg aaccgagaag gacaagcac atggaagcca      180
gcccagcatc cggcccccaga cacttgatgg atccacacat attcacttcc aactttaaca    240
atggcattgg aaggcataag acctacctgt gctacgaagt ggagcgcctg acaatggca     300
cctcggtcaa gatggaccag cacagggcct tctacacaa ccaggctaag aatcttctct      360
gtggcttta cggccgccat gcggagctgc gcttcttgga cctggttcct tctttgcagt     420
tggacccggc ccagatctac aggtcactt ggttcatctc ctggagcccc tgcttctcct      480
ggggctgtgc cggggaagtg cgtgcgttcc ttcaggagaa cacacacgtg agactgcgta    540
tcttcgctgc ccgcatctat gattacgacc cctatataa ggaggcactg caaatgctgc     600
gggatgctgg ggcccaagtc tccatcatga cctacgatga atttaagcac tgctgggaca    660
cctttgtgga ccaccaggga tgtcccttcc agccctggga tggactagat gagcacagcc    720
aagccctgag tgggaggctg cgggccattc tccagaatca gggaaactga aggatgggcc    780
tcagtctcta aggaaggcag agacctgggt tgagcagcag aataaaagat cttcttccaa    840
gaaatgcaaa cagaccgttc accaccatct ccagctgctc acagacgcca gcaaagcagt    900
atgctcccga tcaagtagat ttttaaaaaa tcagagtggg ccgggcgcgg tggctcacgc    960
ctgtaatccc agcactttgg aggccaaggc gggtggatca cgaggtcagg agatcgagac   1020
catcctggct aacacggtga aaccctgtct ctactaaaaa tacaaaaaat tagccaggcg   1080
tggtggcggg cgcctgtagt cccagctact ctggaggctg aggcaggaga gtagcgtgaa   1140
cccgggaggc agagcttgcg gtgagccgag attgcgctac tgcactccag cctgggcgac   1200
agtaccagac tccatctcaa aaaaaaaaaa accagactga attaatttta actgaaaatt   1260
tctcttatgt tccaagtaca caatagtaag attatgctca atattctcag aataattttc   1320
aatgtattaa tgaaatgaaa tgataatttg gcttcatatc tagactaaca caaaattaag   1380
aatcttccat aattgctttt gctcagtaac tgtgtcatga attgcaagag tttccacaaa   1440
cact                                                                 1444
```

<210> SEQ ID NO 6
<211> LENGTH: 199
<212> TYPE: PRT
<213> ORGANISM: Homo sapiens

<400> SEQUENCE: 6

Met Glu Ala Ser Pro Ala Ser Gly Pro Arg His Leu Met Asp Pro His
1               5                   10                  15

Ile Phe Thr Ser Asn Phe Asn Asn Gly Ile Gly Arg His Lys Thr Tyr
            20                  25                  30

Leu Cys Tyr Glu Val Glu Arg Leu Asp Asn Gly Thr Ser Val Lys Met
        35                  40                  45

Asp Gln His Arg Gly Phe Leu His Asn Gln Ala Lys Asn Leu Leu Cys
    50                  55                  60

Gly Phe Tyr Gly Arg His Ala Glu Leu Arg Phe Leu Asp Leu Val Pro
65                  70                  75                  80

Ser Leu Gln Leu Asp Pro Ala Gln Ile Tyr Arg Val Thr Trp Phe Ile
                85                  90                  95

Ser Trp Ser Pro Cys Phe Ser Trp Gly Cys Ala Gly Glu Val Arg Ala
            100                 105                 110

Phe Leu Gln Glu Asn Thr His Val Arg Leu Arg Ile Phe Ala Ala Arg
        115                 120                 125

Ile Tyr Asp Tyr Asp Pro Leu Tyr Lys Glu Ala Leu Gln Met Leu Arg
    130                 135                 140

Asp Ala Gly Ala Gln Val Ser Ile Met Thr Tyr Asp Glu Phe Lys His
145                 150                 155                 160

Cys Trp Asp Thr Phe Val Asp His Gln Gly Cys Pro Phe Gln Pro Trp
                165                 170                 175

Asp Gly Leu Asp Glu His Ser Gln Ala Leu Ser Gly Arg Leu Arg Ala
            180                 185                 190

Ile Leu Gln Asn Gln Gly Asn
        195

<210> SEQ ID NO 7
<211> LENGTH: 1560
<212> TYPE: DNA
<213> ORGANISM: Homo sapiens

<400> SEQUENCE: 7
cacagagctt caaaaaaaga gcgggacagg gacaagcgta tctaagaggc tgaacatgaa      60
tccacagatc agaaatccga tggagcggat gtatcgagac acattctacg acaactttga    120
aaacgaaccc atcctctatg tcggagcta cacttggctg tgctatgaag tgaaaataaa    180 gagggggccgc tcaaatctcc tttgggacac agggtctttt cgaggccagg tgtatttcaa    240
gcctcagtac cacgcagaaa tgtgcttcct ctcttggttc tgtggcaacc agctgcctgc    300
ttacaagtgt ttccagatca cctggtttgt atcctggacc cctgcccgg actgtgtggc    360 gaagctggcc gaattcctgt ctgagcaccc caatgtcacc ctgaccatct ctgccgcccg    420
cctctactac tactgggaaa gagattaccg aagggcgctc tgcaggctga gtcaggcagg    480
agcccgcgtg aagatcatgg actatgaaga atttgcatac tgctgggaaa actttgtgta    540
caatgaaggt cagcaattca tgccttggta caaattcgat gaaaattatg cattcctgca    600
ccgcacgcta aaggagattc tcagatacct gatggatcca gacacattca ctttcaactt    660
taataatgac cctttggtcc ttcgacggcg ccagacctac ttgtgctatg aggtggagcg    720

```
cctggacaat ggcacctggg tcctgatgga ccagcacatg ggctttctat gcaacgaggc    780
taagaatctt ctctgtggct tttacggccg ccatgcggag ctgcgcttct tggacctggt    840
tccttctttg cagttggacc cggcccagat ctacagggtc acttggttca tctcctggag    900
cccctgcttc tcctggggct gtgccgggga agtgcgtgcg ttccttcagg agaacacaca    960
cgtgagactg cgcatcttcg ctgcccgcat ctatgattac gacccctat ataaggaggc    1020 gctgcaaatg ctgcgggatg ctggggccca gtctccatc atgacctacg atgagtttga    1080
gtactgctgg gacacctttg tgtaccgcca gggatgtccc ttccagccct gggatggact    1140
agaggagcac agccaagccc tgagtgggag gctgcgggcc attctccaga atcagggaaa    1200
ctgaaggatg ggcctcagtc tctaaggaag gcagagacct gggttgagca gcagaataaa    1260
agatcttctt ccaagaaatg caaacagacc gttcaccacc atctccagct gctcacagac    1320
accagcaaag caatgtgctc ctgatcaagt agatttttta aaaatcagag tcaattaatt    1380
ttaattgaaa atttctctta tgttccaagt gtacaagagt aagattatgc tcaatattcc    1440
cagaatagtt ttcaatgtat taatgaagtg attaattggc tccatattta gactaataaa    1500
acattaagaa tcttccataa ttgtttccac aaacactaaa aaaaaaaaa aaaaaaaaa     1560

<210> SEQ ID NO 8
<211> LENGTH: 382
<212> TYPE: PRT
<213> ORGANISM: Homo sapiens

<400> SEQUENCE: 8

Met Asn Pro Gln Ile Arg Asn Pro Met Glu Arg Met Tyr Arg Asp Thr
1               5                   10                  15

Phe Tyr Asp Asn Phe Glu Asn Glu Pro Ile Leu Tyr Gly Arg Ser Tyr
            20                  25                  30

Thr Trp Leu Cys Tyr Glu Val Lys Ile Lys Arg Gly Arg Ser Asn Leu
        35                  40                  45

Leu Trp Asp Thr Gly Val Phe Arg Gly Gln Val Tyr Phe Lys Pro Gln
    50                  55                  60

Tyr His Ala Glu Met Cys Phe Leu Ser Trp Phe Cys Gly Asn Gln Leu
65                  70                  75                  80

Pro Ala Tyr Lys Cys Phe Gln Ile Thr Trp Phe Val Ser Trp Thr Pro
                85                  90                  95

Cys Pro Asp Cys Val Ala Lys Leu Ala Glu Phe Leu Ser Glu His Pro
            100                 105                 110

Asn Val Thr Leu Thr Ile Ser Ala Ala Arg Leu Tyr Tyr Tyr Trp Glu
        115                 120                 125

Arg Asp Tyr Arg Arg Ala Leu Cys Arg Leu Ser Gln Ala Gly Ala Arg
    130                 135                 140

Val Lys Ile Met Asp Tyr Glu Glu Phe Ala Tyr Cys Trp Glu Asn Phe
145                 150                 155                 160

Val Tyr Asn Glu Gly Gln Gln Phe Met Pro Trp Tyr Lys Phe Asp Glu
                165                 170                 175

Asn Tyr Ala Phe Leu His Arg Thr Leu Lys Glu Ile Leu Arg Tyr Leu
            180                 185                 190

Met Asp Pro Asp Thr Phe Thr Phe Asn Phe Asn Asn Asp Pro Leu Val
        195                 200                 205

Leu Arg Arg Arg Gln Thr Tyr Leu Cys Tyr Glu Val Glu Arg Leu Asp
    210                 215                 220
```

```
Asn Gly Thr Trp Val Leu Met Asp Gln His Met Gly Phe Leu Cys Asn
225                 230                 235                 240

Glu Ala Lys Asn Leu Leu Cys Gly Phe Tyr Gly Arg His Ala Glu Leu
            245                 250                 255

Arg Phe Leu Asp Leu Val Pro Ser Leu Gln Leu Asp Pro Ala Gln Ile
        260                 265                 270

Tyr Arg Val Thr Trp Phe Ile Ser Trp Ser Pro Cys Phe Ser Trp Gly
    275                 280                 285

Cys Ala Gly Glu Val Arg Ala Phe Leu Gln Glu Asn Thr His Val Arg
290                 295                 300

Leu Arg Ile Phe Ala Ala Arg Ile Tyr Asp Tyr Asp Pro Leu Tyr Lys
305                 310                 315                 320

Glu Ala Leu Gln Met Leu Arg Asp Ala Gly Ala Gln Val Ser Ile Met
            325                 330                 335

Thr Tyr Asp Glu Phe Glu Tyr Cys Trp Asp Thr Phe Val Tyr Arg Gln
        340                 345                 350

Gly Cys Pro Phe Gln Pro Trp Asp Gly Leu Glu Glu His Ser Gln Ala
    355                 360                 365

Leu Ser Gly Arg Leu Arg Ala Ile Leu Gln Asn Gln Gly Asn
370                 375                 380

<210> SEQ ID NO 9
<211> LENGTH: 4104
<212> TYPE: DNA
<213> ORGANISM: Streptococcus pyogenes

<400> SEQUENCE: 9
atggataaga aatactcaat aggcttagat atcggcacaa atagcgtcgg atgggcggtg      60
atcactgatg aatataaggt tccgtctaaa aagttcaagg ttctgggaaa tacagaccgc     120
cacagtatca aaaaaaatct tataggggct cttttatttg cagtggagag acagcggaa     180 gcgactcgtc tcaaacggac agctcgtaga aggtatacac gtcggaagaa tcgtatttgt     240
tatctacagg agatttttc aaatgagatg gcgaaagtag atgatagttt ctttcatcga     300
cttgaagagt cttttttggt ggaagaagac aagaagcatg aacgtcatcc tatttttgga     360
aatatagtag atgaagttgc ttatcatgag aaatatccaa ctatctatca tctgcgaaaa     420
aaattggcag attctactga taaagcggat ttgcgcttaa tctatttggc cttagcgcat     480
atgattaagt ttcgtggtca ttttttgatt gagggagatt taaatcctga taatagtgat     540
gtggacaaac tatttatcca gttggtacaa atctacaatc aattatttga agaaaaccct     600
attaacgcaa gtagagtaga tgctaaagcg attcttctg cacgattgag taaatcaaga     660
cgattagaaa atctcattgc tcagctcccc ggtgagaaga gaaatggctt gtttgggaat     720
ctcattgctt tgtcattggg attgaccct aatttttaaat caaattttga tttggcagaa     780
gatgctaaat tacagctttc aaaagatact tacgatgatg atttagataa tttattggcg     840
caaattggag atcaatatgc tgatttgttt ttggcagcta gaatttatc agatgctatt     900 ttactttcag atatcctaag agtaaatagt gaaataacta aggctcccct atcagcttca     960
atgattaagc gctacgatga acatcatcaa gacttgactc ttttaaaagc tttagttcga    1020
caacaacttc cagaaaagta taagaaatc ttttttgatc aatcaaaaaa cggatatgca    1080
ggttatattg atgggggagc tagccaagaa gaatttata aatttatcaa accaatttta    1140
gaaaaaatgg atggtactga ggaattattg gtgaaactaa atcgtgaaga tttgctgcgc    1200
aagcaacgga cctttgacaa cggctctatt ccccatcaaa ttcacttggg tgagctgcat    1260
```

```
gctattttga gaagacaaga agactttat ccattttaa aagacaatcg tgagaagatt    1320
gaaaaaatct tgacttttcg aattccttat tatgttggtc cattggcgcg tggcaatagt    1380
cgttttgcat ggatgactcg gaagtctgaa gaaacaatta ccccatggaa ttttgaagaa    1440
gttgtcgata aggtgcttc agctcaatca tttattgaac gcatgacaaa ctttgataaa    1500
aatcttccaa atgaaaagt actaccaaaa catagtttgc tttatgagta ttttacggtt    1560
tataacgaat tgacaaggt caaatatgtt actgagggaa tgcgaaaacc agcatttctt    1620
tcaggtgaac agaagaaagc cattgttgat ttactcttca aaacaaatcg aaaagtaacc    1680
gttaagcaat taaagaaga ttatttcaaa aaatagaat gttttgatag tgttgaaatt    1740
tcaggagttg aagatagatt taatgcttca ttaggcgcct accatgattt gctaaaaatt    1800
attaaagata aagatttttt ggataatgaa gaaaatgaag atatcttaga ggatattgtt    1860
ttaacattga ccttatttga agataggggg atgattgagg aaagacttaa acatatgct     1920 cacctctttg atgataaggt gatgaaacag cttaaacgtc gccgttatac tggttgggga    1980
cgtttgtctc gaaaattgat taatggtatt agggataagc aatctggcaa aacaatatta    2040 gatttttga aatcagatgg ttttgccaat cgcaatttta tgcagctgat ccatgatgat    2100
agtttgacat ttaaagaaga tattcaaaaa gcacaggtgt ctggacaagg ccatagttta    2160
catgaacaga ttgctaactt agctggcagt cctgctatta aaaaggtat tttacagact    2220 gtaaaaattg ttgatgaact ggtcaaagta atggggcata agccagaaaa tatcgttatt    2280
gaaatggcac gtgaaaatca gacaactcaa aagggccaga aaattcgcg agagcgtatg    2340 aaacgaatcg aagaaggtat caagaatta ggaagtcaga ttcttaaaga gcatcctgtt    2400
gaaaatactc aattgcaaaa tgaaaagctc tatctctatt atctacaaaa tggaagagac    2460
atgtatgtgg accaagaatt agatattaat cgtttaagtg attatgatgt cgatcacatt    2520
gttccacaaa gtttcattaa agacgattca atagacaata aggtactaac gcgttctgat    2580
aaaaatcgtg gtaaatcgga taacgttcca agtgaagaag tagtcaaaaa gatgaaaaac    2640
tattggagac aacttctaaa cgccaagtta atcactcaac gtaagtttga taattaacg     2700 aaagctgaac gtggaggttt gagtgaactt gataaagctg gttttatcaa cgccaattg     2760 gttgaaactc gccaaatcac taagcatgtg gcacaaattt tggatagtcg catgaatact    2820
aaatacgatg aaaatgataa acttattcga gaggttaaag tgattacctt aaaatctaaa    2880
ttagtttctg acttccgaaa agatttccaa ttctataaag tacgtgagat taacaattac    2940
catcatgccc atgatgcgta tctaaatgcc gtcgttggaa ctgctttgat taagaaatat    3000
ccaaaacttg aatcggagtt tgtctatggt gattataaag tttatgatgt tcgtaaaatg    3060
attgctaagt ctgagcaaga aataggcaaa gcaaccgcaa atatttctt ttactctaat     3120 atcatgaact tcttcaaaac agaaattaca cttgcaaatg gagagattcg caaacgccct    3180
ctaatcgaaa ctaatgggga aactggagaa attgtctggg ataaagggcg agattttgcc    3240
acagtgcgca agtattgtc catgccccaa gtcaatattg tcaagaaaac agaagtacag    3300
acaggcggat tctccaagga gtcaatttta ccaaaaagaa attcggacaa gcttattgct    3360
cgtaaaaaag actgggatcc aaaaaaatat ggtggttttg atagtccaac ggtagcttat    3420
tcagtcctag tggttgctaa ggtggaaaaa gggaaatcga agaagttaaa atccgttaaa    3480
gagttactag ggatcacaat tatggaaaga agttcctttg aaaaaaatcc gattgacttt    3540
ttagaagcta aaggatataa ggaagttaaa aaagacttaa tcattaaact acctaaatat    3600
```

-continued

```
agtcttttg agttagaaaa cggtcgtaaa cggatgctgg ctagtgccgg agaattacaa    3660
aaaggaaatg agctggctct gccaagcaaa tatgtgaatt ttttatattt agctagtcat   3720
tatgaaaagt tgaagggtag tccagaagat aacgaacaaa acaattgtt tgtggagcag    3780 cataagcatt atttagatga gattattgag caaatcagtg aatttctaa gcgtgttatt    3840 ttagcagatg ccaatttaga taaagttctt agtgcatata caaacatag agacaaacca    3900 atacgtgaac aagcagaaaa tattattcat ttatttacgt tgacgaatct tggagctccc   3960
gctgctttta aatattttga tacaacaatt gatcgtaaac gatatacgtc tacaaaagaa   4020
gttttagatg ccactcttat ccatcaatcc atcactggtc tttatgaaac acgcattgat   4080
ttgagtcagc taggaggtga ctga                                          4104
```

<210> SEQ ID NO 10
<211> LENGTH: 1368
<212> TYPE: PRT
<213> ORGANISM: Streptococcus pyogenes

<400> SEQUENCE: 10

```
Met Asp Lys Lys Tyr Ser Ile Gly Leu Asp Ile Gly Thr Asn Ser Val
1               5                   10                  15

Gly Trp Ala Val Ile Thr Asp Asp Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Ser Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285
```

```
Leu Phe Leu Ala Ala Lys Asn Leu Ser Asp Ala Ile Leu Leu Ser Asp
            290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
        450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
690                 695                 700
```

-continued

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Asp Glu Leu Val Lys Val Met Gly
            740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
        900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro

```
              1115                1120                1125

Lys Lys Tyr Gly Gly Phe Asp Ser Pro Thr Val Ala Tyr Ser Val
            1130                1135                1140

Leu Val Val Ala Lys Val Glu Lys Gly Lys Ser Lys Lys Leu Lys
            1145                1150                1155

Ser Val Lys Glu Leu Leu Gly Ile Thr Ile Met Glu Arg Ser Ser
            1160                1165                1170

Phe Glu Lys Asn Pro Ile Asp Phe Leu Glu Ala Lys Gly Tyr Lys
            1175                1180                1185

Glu Val Lys Lys Asp Leu Ile Ile Lys Leu Pro Lys Tyr Ser Leu
            1190                1195                1200

Phe Glu Leu Glu Asn Gly Arg Lys Arg Met Leu Ala Ser Ala Gly
            1205                1210                1215

Glu Leu Gln Lys Gly Asn Glu Leu Ala Leu Pro Ser Lys Tyr Val
            1220                1225                1230

Asn Phe Leu Tyr Leu Ala Ser His Tyr Glu Lys Leu Lys Gly Ser
            1235                1240                1245

Pro Glu Asp Asn Glu Gln Lys Gln Leu Phe Val Glu Gln His Lys
            1250                1255                1260

His Tyr Leu Asp Glu Ile Ile Glu Gln Ile Ser Glu Phe Ser Lys
            1265                1270                1275

Arg Val Ile Leu Ala Asp Ala Asn Leu Asp Lys Val Leu Ser Ala
            1280                1285                1290

Tyr Asn Lys His Arg Asp Lys Pro Ile Arg Glu Gln Ala Glu Asn
            1295                1300                1305

Ile Ile His Leu Phe Thr Leu Thr Asn Leu Gly Ala Pro Ala Ala
            1310                1315                1320

Phe Lys Tyr Phe Asp Thr Thr Ile Asp Arg Lys Arg Tyr Thr Ser
            1325                1330                1335

Thr Lys Glu Val Leu Asp Ala Thr Leu Ile His Gln Ser Ile Thr
            1340                1345                1350

Gly Leu Tyr Glu Thr Arg Ile Asp Leu Ser Gln Leu Gly Gly Asp
            1355                1360                1365

<210> SEQ ID NO 11
<211> LENGTH: 1368
<212> TYPE: PRT
<213> ORGANISM: Artificial Sequence
<220> FEATURE:
<223> OTHER INFORMATION: synthetic polypeptide

<400> SEQUENCE: 11

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
```

-continued

```
               100                 105                 110
His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
            130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
            195                 200                 205

Lys Ala Ile Leu Ser Ala Arg Leu Ser Lys Ser Arg Arg Leu Glu Asn
            210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
            290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
            355                 360                 365

Gln Glu Glu Phe Tyr Lys Phe Ile Lys Pro Ile Leu Glu Lys Met Asp
            370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
            435                 440                 445

Pro Tyr Tyr Val Gly Pro Leu Ala Arg Gly Asn Ser Arg Phe Ala Trp
            450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
            515                 520                 525
```

-continued

Tyr Val Thr Glu Gly Met Arg Lys Pro Ala Phe Leu Ser Gly Glu Gln
530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp Ala Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
930                 935                 940

```
Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
            995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
```

```
                1340                1345                1350
Gly Leu Tyr Glu Thr Arg Ile Asp Leu Ser Gln Leu Gly Gly Asp
            1355                1360                1365

<210> SEQ ID NO 12
<211> LENGTH: 1368
<212> TYPE: PRT
<213> ORGANISM: Artificial Sequence
<220> FEATURE:
<223> OTHER INFORMATION: synthetic polypeptide

<400> SEQUENCE: 12

Met Asp Lys Lys Tyr Ser Ile Gly Leu Ala Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
```

```
              340                 345                 350
Asp Gln Ser Lys Asn Gly Tyr Ala Gly Tyr Ile Asp Gly Gly Ala Ser
            355                 360                 365
Gln Glu Glu Phe Tyr Lys Phe Ile Lys Pro Ile Leu Glu Lys Met Asp
            370                 375             380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
            435                 440                 445
Pro Tyr Tyr Val Gly Pro Leu Ala Arg Gly Asn Ser Arg Phe Ala Trp
        450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
        530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
                580                 585                 590
Thr Tyr His Asp Leu Leu Lys Ile Ile Lys Asp Lys Asp Phe Leu Asp
            595                 600                 605
Asn Glu Glu Asn Glu Asp Ile Leu Glu Asp Ile Val Leu Thr Leu Thr
        610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
            660                 665                 670
Lys Gln Ser Gly Lys Thr Ile Leu Asp Phe Leu Lys Ser Asp Gly Phe
            675                 680                 685
Ala Asn Arg Asn Phe Met Gln Leu Ile His Asp Asp Ser Leu Thr Phe
        690                 695                 700
Lys Glu Asp Ile Gln Lys Ala Gln Val Ser Gly Gln Gly Asp Ser Leu
705                 710                 715                 720
His Glu His Ile Ala Asn Leu Ala Gly Ser Pro Ala Ile Lys Lys Gly
                725                 730                 735
Ile Leu Gln Thr Val Lys Val Val Asp Glu Leu Val Lys Val Met Gly
            740                 745                 750
Arg His Lys Pro Glu Asn Ile Val Ile Glu Met Ala Arg Glu Asn Gln
        755                 760                 765
```

```
Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
                835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Val Val Lys Lys Met Lys Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
                915                 920                 925

Lys His Val Ala Gln Ile Leu Asp Ser Arg Met Asn Thr Lys Tyr Asp
                930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
                995                1000                1005

Val Tyr Gly Asp Tyr Lys Val Tyr Asp Val Arg Lys Met Ile Ala
                1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170
```

-continued

Phe Glu Lys Asn Pro Ile Asp Phe Leu Glu Ala Lys Gly Tyr Lys
1175                1180                1185

Glu Val Lys Lys Asp Leu Ile Ile Lys Leu Pro Lys Tyr Ser Leu
1190                1195                1200

Phe Glu Leu Glu Asn Gly Arg Lys Arg Met Leu Ala Ser Ala Gly
1205                1210                1215

Glu Leu Gln Lys Gly Asn Glu Leu Ala Leu Pro Ser Lys Tyr Val
1220                1225                1230

Asn Phe Leu Tyr Leu Ala Ser His Tyr Glu Lys Leu Lys Gly Ser
1235                1240                1245

Pro Glu Asp Asn Glu Gln Lys Gln Leu Phe Val Glu Gln His Lys
1250                1255                1260

His Tyr Leu Asp Glu Ile Ile Glu Gln Ile Ser Glu Phe Ser Lys
1265                1270                1275

Arg Val Ile Leu Ala Asp Ala Asn Leu Asp Lys Val Leu Ser Ala
1280                1285                1290

Tyr Asn Lys His Arg Asp Lys Pro Ile Arg Glu Gln Ala Glu Asn
1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
1355                1360                1365

<210> SEQ ID NO 13
<211> LENGTH: 1368
<212> TYPE: PRT
<213> ORGANISM: Artificial Sequence
<220> FEATURE:
<223> OTHER INFORMATION: synthetic polypeptide

<400> SEQUENCE: 13

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
                100                 105                 110

His Glu Arg His Pro Ile Phe Gly Asn Ile Val Asp Glu Val Ala Tyr
            115                 120                 125

His Glu Lys Tyr Pro Thr Ile Tyr His Leu Arg Lys Lys Leu Val Asp
        130                 135                 140

Ser Thr Asp Lys Ala Asp Leu Arg Leu Ile Tyr Leu Ala Leu Ala His
145                 150                 155                 160

-continued

```
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
            180                 185                 190
Asn Gln Leu Phe Glu Glu Asn Pro Ile Asn Ala Ser Gly Val Asp Ala
        195                 200                 205
Lys Ala Ile Leu Ser Ala Arg Leu Ser Lys Ser Arg Arg Leu Glu Asn
    210                 215                 220
Leu Ile Ala Gln Leu Pro Gly Glu Lys Lys Asn Gly Leu Phe Gly Asn
225                 230                 235                 240
Leu Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
            260                 265                 270
Asp Asp Leu Asp Asn Leu Leu Ala Gln Ile Gly Asp Gln Tyr Ala Asp
        275                 280                 285
Leu Phe Leu Ala Ala Lys Asn Leu Ser Asp Ala Ile Leu Leu Ser Asp
    290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
    450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
        515                 520                 525
Tyr Val Thr Glu Gly Met Arg Lys Pro Ala Phe Leu Ser Gly Glu Gln
    530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
```

```
                580               585               590
Thr Tyr His Asp Leu Leu Lys Ile Ile Lys Asp Lys Asp Phe Leu Asp
                595               600               605

Asn Glu Glu Asn Glu Asp Ile Leu Glu Asp Ile Val Leu Thr Leu Thr
                610               615               620

Leu Phe Glu Asp Arg Glu Met Ile Glu Glu Arg Leu Lys Thr Tyr Ala
625               630               635               640

His Leu Phe Asp Asp Lys Val Met Lys Gln Leu Lys Arg Arg Arg Tyr
                645               650               655

Thr Gly Trp Gly Arg Leu Ser Arg Lys Leu Ile Asn Gly Ile Arg Asp
                660               665               670

Lys Gln Ser Gly Lys Thr Ile Leu Asp Phe Leu Lys Ser Asp Gly Phe
                675               680               685

Ala Asn Arg Asn Phe Met Gln Leu Ile His Asp Asp Ser Leu Thr Phe
                690               695               700

Lys Glu Asp Ile Gln Lys Ala Gln Val Ser Gly Gln Gly Asp Ser Leu
705               710               715               720

His Glu His Ile Ala Asn Leu Ala Gly Ser Pro Ala Ile Lys Lys Gly
                725               730               735

Ile Leu Gln Thr Val Lys Val Val Asp Glu Leu Val Lys Val Met Gly
                740               745               750

Arg His Lys Pro Glu Asn Ile Val Ile Glu Met Ala Arg Glu Asn Gln
                755               760               765

Thr Thr Gln Lys Gly Gln Lys Asn Ser Arg Glu Arg Met Lys Arg Ile
                770               775               780

Glu Glu Gly Ile Lys Glu Leu Gly Ser Gln Ile Leu Lys Glu His Pro
785               790               795               800

Val Glu Asn Thr Gln Leu Gln Asn Glu Lys Leu Tyr Leu Tyr Tyr Leu
                805               810               815

Gln Asn Gly Arg Asp Met Tyr Val Asp Gln Glu Leu Asp Ile Asn Arg
                820               825               830

Leu Ser Asp Tyr Asp Val Asp Ala Ile Val Pro Gln Ser Phe Leu Lys
                835               840               845

Asp Asp Ser Ile Asp Asn Lys Val Leu Thr Arg Ser Asp Lys Asn Arg
                850               855               860

Gly Lys Ser Asp Asn Val Pro Ser Glu Glu Val Val Lys Lys Met Lys
865               870               875               880

Asn Tyr Trp Arg Gln Leu Leu Asn Ala Lys Leu Ile Thr Gln Arg Lys
                885               890               895

Phe Asp Asn Leu Thr Lys Ala Glu Arg Gly Gly Leu Ser Glu Leu Asp
                900               905               910

Lys Ala Gly Phe Ile Lys Arg Gln Leu Val Glu Thr Arg Gln Ile Thr
                915               920               925

Lys His Val Ala Gln Ile Leu Asp Ser Arg Met Asn Thr Lys Tyr Asp
                930               935               940

Glu Asn Asp Lys Leu Ile Arg Glu Val Lys Val Ile Thr Leu Lys Ser
945               950               955               960

Lys Leu Val Ser Asp Phe Arg Lys Asp Phe Gln Phe Tyr Lys Val Arg
                965               970               975

Glu Ile Asn Asn Tyr His His Ala His Asp Ala Tyr Leu Asn Ala Val
                980               985               990

Val Gly Thr Ala Leu Ile Lys Lys  Tyr Pro Lys Leu Glu  Ser Glu Phe
                995              1000              1005
```

Val Tyr Gly Asp Tyr Lys Val Tyr Asp Val Arg Lys Met Ile Ala
1010                1015                1020

Lys Ser Glu Gln Glu Ile Gly Lys Ala Thr Ala Lys Tyr Phe Phe
1025                1030                1035

Tyr Ser Asn Ile Met Asn Phe Phe Lys Thr Glu Ile Thr Leu Ala
1040                1045                1050

Asn Gly Glu Ile Arg Lys Arg Pro Leu Ile Glu Thr Asn Gly Glu
1055                1060                1065

Thr Gly Glu Ile Val Trp Asp Lys Gly Arg Asp Phe Ala Thr Val
1070                1075                1080

Arg Lys Val Leu Ser Met Pro Gln Val Asn Ile Val Lys Lys Thr
1085                1090                1095

Glu Val Gln Thr Gly Gly Phe Ser Lys Glu Ser Ile Leu Pro Lys
1100                1105                1110

Arg Asn Ser Asp Lys Leu Ile Ala Arg Lys Lys Asp Trp Asp Pro
1115                1120                1125

Lys Lys Tyr Gly Gly Phe Asp Ser Pro Thr Val Ala Tyr Ser Val
1130                1135                1140

Leu Val Val Ala Lys Val Glu Lys Gly Lys Ser Lys Lys Leu Lys
1145                1150                1155

Ser Val Lys Glu Leu Leu Gly Ile Thr Ile Met Glu Arg Ser Ser
1160                1165                1170

Phe Glu Lys Asn Pro Ile Asp Phe Leu Glu Ala Lys Gly Tyr Lys
1175                1180                1185

Glu Val Lys Lys Asp Leu Ile Ile Lys Leu Pro Lys Tyr Ser Leu
1190                1195                1200

Phe Glu Leu Glu Asn Gly Arg Lys Arg Met Leu Ala Ser Ala Gly
1205                1210                1215

Glu Leu Gln Lys Gly Asn Glu Leu Ala Leu Pro Ser Lys Tyr Val
1220                1225                1230

Asn Phe Leu Tyr Leu Ala Ser His Tyr Glu Lys Leu Lys Gly Ser
1235                1240                1245

Pro Glu Asp Asn Glu Gln Lys Gln Leu Phe Val Glu Gln His Lys
1250                1255                1260

His Tyr Leu Asp Glu Ile Ile Glu Gln Ile Ser Glu Phe Ser Lys
1265                1270                1275

Arg Val Ile Leu Ala Asp Ala Asn Leu Asp Lys Val Leu Ser Ala
1280                1285                1290

Tyr Asn Lys His Arg Asp Lys Pro Ile Arg Glu Gln Ala Glu Asn
1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
1355                1360                1365

<210> SEQ ID NO 14
<211> LENGTH: 5
<212> TYPE: PRT
<213> ORGANISM: Artificial Sequence
<220> FEATURE:

```
<223> OTHER INFORMATION: synthetic

<400> SEQUENCE: 14

Gly Gly Gly Gly Ser
1               5

<210> SEQ ID NO 15
<211> LENGTH: 5
<212> TYPE: PRT
<213> ORGANISM: Artificial Sequence
<220> FEATURE:
<223> OTHER INFORMATION: synthetic

<400> SEQUENCE: 15

Glu Ala Ala Ala Lys
1               5

<210> SEQ ID NO 16
<211> LENGTH: 16
<212> TYPE: PRT
<213> ORGANISM: Artificial Sequence
<220> FEATURE:
<223> OTHER INFORMATION: synthetic

<400> SEQUENCE: 16

Ser Gly Ser Glu Thr Pro Gly Thr Ser Glu Ser Ala Thr Pro Glu Ser
1               5                   10                  15

<210> SEQ ID NO 17
<211> LENGTH: 9
<212> TYPE: PRT
<213> ORGANISM: Artificial Sequence
<220> FEATURE:
<223> OTHER INFORMATION: consensus

<400> SEQUENCE: 17

Leu Ala Gly Leu Ile Asp Ala Asp Gly
1               5

<210> SEQ ID NO 18
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 18
agatccgcgg ccgcgccgcc accatgatgg aagccagccc agcatccggg c            51

<210> SEQ ID NO 19
<211> LENGTH: 52
<212> TYPE: DNA
<213> ORGANISM: Artificial Sequence
<220> FEATURE:
<223> OTHER INFORMATION: synthetic oligonucleotide

<400> SEQUENCE: 19
tgaggtcccg ggagtctcgc tgccgcttcc gtttccctga ttctggagaa tg           52

<210> SEQ ID NO 20
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 20
```

-continued agatccgcgg ccgcgccgcc accatggatc cagacacatt cactttcaac t    51

<210> SEQ ID NO 21
<211> LENGTH: 52
<212> TYPE: DNA
<213> ORGANISM: Artificial Sequence
<220> FEATURE:
<223> OTHER INFORMATION: synthetic oligonucleotide

<400> SEQUENCE: 21
tgaggtcccg ggagtctcgc tgccgctgtt tccctgattc tggagaatgg cc    52

<210> SEQ ID NO 22
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 22
aagggtggcc cctcaccctt cgcctggg    28

<210> SEQ ID NO 23
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 23
cccaggcgaa gggtgagggg ccaccctt    28

<210> SEQ ID NO 24
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 24
acacctggcc cctcaccctt cgcctg    26

<210> SEQ ID NO 25
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 25
aaaacaggcg aagggtgagg ggccag    26

<210> SEQ ID NO 26
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 26
acaccgcact accagagcta actcag    26

<210> SEQ ID NO 27
<211> LENGTH: 26
<212> TYPE: DNA

```
<213> ORGANISM: Artificial Sequence
<220> FEATURE:
<223> OTHER INFORMATION: synthetic oligonucleotide

<400> SEQUENCE: 27
aaaactgagt tagctctggt agtgcg                                          26

<210> SEQ ID NO 28
<211> LENGTH: 31
<212> TYPE: DNA
<213> ORGANISM: Artificial Sequence
<220> FEATURE:
<223> OTHER INFORMATION: synthetic oligonucleotide

<400> SEQUENCE: 28
ctggctaccg gtatggtgag caagggcgag g                                    31

<210> SEQ ID NO 29
<211> LENGTH: 110
<212> TYPE: DNA
<213> ORGANISM: Artificial Sequence
<220> FEATURE:
<223> OTHER INFORMATION: synthetic oligonucleotide

<400> SEQUENCE: 29
ttaaaggtac cagggccggg attctcctcc acgtcaccgc atgttagaag acttcctctg     60
ccctccttgt actcgagatc tgcaccgggc ttgtacagct cgtccatgcc                110

<210> SEQ ID NO 30
<211> LENGTH: 103
<212> TYPE: DNA
<213> ORGANISM: Artificial Sequence
<220> FEATURE:
<223> OTHER INFORMATION: synthetic oligonucleotide

<400> SEQUENCE: 30
gcagatctcg agtacaagga gggcagagga agtcttctaa catgcggtga cgtggaggag     60
aatcccggcc ctctggtcag taaaggtgaa gaactgttca ccg                       103

<210> SEQ ID NO 31
<211> LENGTH: 41
<212> TYPE: DNA
<213> ORGANISM: Artificial Sequence
<220> FEATURE:
<223> OTHER INFORMATION: synthetic oligonucleotide

<400> SEQUENCE: 31
cttaaaggta ccttatttat ataattcatc cataccgaga g                         41

<210> SEQ ID NO 32
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 32
atggccatca tcaaggagtt                                                 20

<210> SEQ ID NO 33
<211> LENGTH: 20
<212> TYPE: DNA
<213> ORGANISM: Artificial Sequence
<220> FEATURE:
<223> OTHER INFORMATION: synthetic oligonucleotide
```

<400> SEQUENCE: 33
ctctgccctc cttgtactcg                                          20

<210> SEQ ID NO 34
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 34
cgactcacta tagggagagc ggc                                      23

<210> SEQ ID NO 35
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 35
aagaacatcg attttccatg gcag                                     24

<210> SEQ ID NO 36
<211> LENGTH: 59
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(3)
<223> OTHER INFORMATION: n is a, c, g, or t

<400> SEQUENCE: 36
nnngagctca gagactggcc cagtggctgt ggaccccaca ttgaggtgag tccaggaga    59

<210> SEQ ID NO 37
<211> LENGTH: 59
<212> TYPE: DNA
<213> ORGANISM: Artificial Sequence
<220> FEATURE:
<223> OTHER INFORMATION: synthetic oligonucleotide
<220> FEATURE:
<221> NAME/KEY: misc_feature
<222> LOCATION: (1)..(3)
<223> OTHER INFORMATION: n is a, c, g, or t

<400> SEQUENCE: 37
nnngagctct ctcggatcga agaatacctc aaactcatgg ggctcgatcc gccgtctgt    59

<210> SEQ ID NO 38
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 38
ccatgcccga aggtcacgta caggagcgga ccatcttc                      38

<210> SEQ ID NO 39
<211> LENGTH: 38
<212> TYPE: DNA
<213> ORGANISM: Artificial Sequence
<220> FEATURE:

<223> OTHER INFORMATION: synthetic oligonucleotide

<400> SEQUENCE: 39
gaagatggtc cgctcctgta cgtgaccttc gggcatgg                    38

<210> SEQ ID NO 40
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 40
ggacggcaac atttcagggc acaagctgga                              30

<210> SEQ ID NO 41
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 41
tccagcttgt gccctgaaat gttgccgtcc                              30

<210> SEQ ID NO 42
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 42
cgacaaccac tattcaagta cccagtcggc cctga                        35

<210> SEQ ID NO 43
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 43
tcagggccga ctgggtactt gaatagtggt tgtcg                        35

<210> SEQ ID NO 44
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 44
agatccgcgg ccgcgccgcc accatgaatc cacagatcag aaatccgatg g     51

<210> SEQ ID NO 45
<211> LENGTH: 52
<212> TYPE: DNA
<213> ORGANISM: Artificial Sequence
<220> FEATURE:
<223> OTHER INFORMATION: synthetic oligonucleotide

<400> SEQUENCE: 45
tgaggtcccg ggagtctcgc tgccgctgtt tccctgattc tggagaatgg cc    52

```
<210> SEQ ID NO 46
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 46
agatccgcgg ccgcgccgcc accatgaatc cacagatcag aaacccgatg a        51

<210> SEQ ID NO 47
<211> LENGTH: 52
<212> TYPE: DNA
<213> ORGANISM: Artificial Sequence
<220> FEATURE:
<223> OTHER INFORMATION: synthetic oligonucleotide

<400> SEQUENCE: 47
tgaggtcccg ggagtctcgc tgccgctctg gagactctcc cgtagccttc tt       52

<210> SEQ ID NO 48
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 48
agatccgcgg ccgcgccgcc accatgaatc cacagatcag aaatccgatg g        51

<210> SEQ ID NO 49
<211> LENGTH: 52
<212> TYPE: DNA
<213> ORGANISM: Artificial Sequence
<220> FEATURE:
<223> OTHER INFORMATION: synthetic oligonucleotide

<400> SEQUENCE: 49
tgaggtcccg ggagtctcgc tgccgctctg gagaatctcc cgtagccttc tt       52

<210> SEQ ID NO 50
<211> LENGTH: 51
<212> TYPE: DNA
<213> ORGANISM: Artificial Sequence
<220> FEATURE:
<223> OTHER INFORMATION: synthetic oligonucleotide

<400> SEQUENCE: 50
agatccgcgg ccgcgccgcc accatgaagc ctcacttcag aaacacagtg g        51

<210> SEQ ID NO 51
<211> LENGTH: 52
<212> TYPE: DNA
<213> ORGANISM: Artificial Sequence
<220> FEATURE:
<223> OTHER INFORMATION: synthetic oligonucleotide

<400> SEQUENCE: 51
tgaggtcccg ggagtctcgc tgccgctctc gagaatctcc tgcagcttgc tg       52

<210> SEQ ID NO 52
<211> LENGTH: 51
<212> TYPE: DNA
<213> ORGANISM: Artificial Sequence
<220> FEATURE:
<223> OTHER INFORMATION: synthetic oligonucleotide
```

<400> SEQUENCE: 52
agatccgcgg ccgcgccgcc accatgaagc tcacttcag aaacacagtg g        51

<210> SEQ ID NO 53
<211> LENGTH: 52
<212> TYPE: DNA
<213> ORGANISM: Artificial Sequence
<220> FEATURE:
<223> OTHER INFORMATION: synthetic oligonucleotide

<400> SEQUENCE: 53
tgaggtcccg ggagtctcgc tgccgctgtt ttcctgattc tggagaatgg cc        52

<210> SEQ ID NO 54
<211> LENGTH: 52
<212> TYPE: DNA
<213> ORGANISM: Artificial Sequence
<220> FEATURE:
<223> OTHER INFORMATION: synthetic oligonucleotide

<400> SEQUENCE: 54
agatccgcgg ccgcgccgcc accatggctc tgttaacagc cgaaacattc cg        52

<210> SEQ ID NO 55
<211> LENGTH: 52
<212> TYPE: DNA
<213> ORGANISM: Artificial Sequence
<220> FEATURE:
<223> OTHER INFORMATION: synthetic oligonucleotide

<400> SEQUENCE: 55
tgaggtcccg ggagtctcgc tgccgcttca ggactgcttt atcctgtcaa gc        52

<210> SEQ ID NO 56
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 56
acaccccgaa ggtcacgtac aggag        25

<210> SEQ ID NO 57
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 57
aaaacctcct gtacgtgacc ttcggg        26

<210> SEQ ID NO 58
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 58
acacccaaca tttcagggca caagcg        26

<210> SEQ ID NO 59
<211> LENGTH: 26

```
<212> TYPE: DNA
<213> ORGANISM: Artificial Sequence
<220> FEATURE:
<223> OTHER INFORMATION: synthetic oligonucleotide

<400> SEQUENCE: 59
aaaacgcttg tgccctgaaa tgttgg                                          26

<210> SEQ ID NO 60
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 60
acaccccact attcaagtac ccagtg                                          26

<210> SEQ ID NO 61
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 61
aaaacactgg gtacttgaat agtggg                                          26

<210> SEQ ID NO 62
<211> LENGTH: 81
<212> TYPE: DNA
<213> ORGANISM: Artificial Sequence
<220> FEATURE:
<223> OTHER INFORMATION: synthetic oligonucleotide

<400> SEQUENCE: 62
ggtgaccaag ggtggcccct cacccttcgc ctggggtggc ccctcaccct tcgcctggcc     60
cctcaccctt cgcctgggac a                                               81

<210> SEQ ID NO 63
<211> LENGTH: 81
<212> TYPE: DNA
<213> ORGANISM: Artificial Sequence
<220> FEATURE:
<223> OTHER INFORMATION: synthetic oligonucleotide

<400> SEQUENCE: 63
ggtgaccaag ggtggcccct uacccttcgc ctggggtggc ccctcaccct tcgcctggcc     60
cctuaccctt cgcctgggac a                                               81

<210> SEQ ID NO 64
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 64
ggtgaccaag ggtggcccct cagcctggga ca                                   32

<210> SEQ ID NO 65
<211> LENGTH: 32
<212> TYPE: DNA
<213> ORGANISM: Artificial Sequence
<220> FEATURE:
```

<223> OTHER INFORMATION: synthetic oligonucleotide

<400> SEQUENCE: 65
ggtgaccaag ggtggcccct cagcctggga ca                          32

<210> SEQ ID NO 66
<211> LENGTH: 37
<212> TYPE: DNA
<213> ORGANISM: Artificial Sequence
<220> FEATURE:
<223> OTHER INFORMATION: synthetic oligonucleotide

<400> SEQUENCE: 66
ggtgaccaag ggtggttctt acccttcgcc tgggaca                     37

<210> SEQ ID NO 67
<211> LENGTH: 20
<212> TYPE: DNA
<213> ORGANISM: Artificial Sequence
<220> FEATURE:
<223> OTHER INFORMATION: synthetic oligonucleotide

<400> SEQUENCE: 67
ggtacccttc gcctgggaca                                        20

<210> SEQ ID NO 68
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 68
ggtgaccaag ggtttttat ccttcgcctg ggaca                        35

<210> SEQ ID NO 69
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 69
ggtgaccaag ggtggttttt tacccttcgc ctgggaca                    38

<210> SEQ ID NO 70
<211> LENGTH: 56
<212> TYPE: DNA
<213> ORGANISM: Artificial Sequence
<220> FEATURE:
<223> OTHER INFORMATION: synthetic oligonucleotide

<400> SEQUENCE: 70
ggtgaccaag ggtggttttt taacccttg cctggggtgg ccctcgcct gggaca  56

<210> SEQ ID NO 71
<211> LENGTH: 74
<212> TYPE: DNA
<213> ORGANISM: Artificial Sequence
<220> FEATURE:
<223> OTHER INFORMATION: synthetic oligonucleotide

<400> SEQUENCE: 71
ggtgaccaag ggtggctttt tacccttcgc ctggggtggc ttttacccct tcgcctggcc  60
cttcgcctgg gaca                                              74

<210> SEQ ID NO 72
<211> LENGTH: 56
<212> TYPE: DNA
<213> ORGANISM: Artificial Sequence
<220> FEATURE:
<223> OTHER INFORMATION: synthetic oligonucleotide

<400> SEQUENCE: 72
ggtgaccaag ggtggttttt tacccttcgc ctggcccctc accttcgcct gggaca      56

<210> SEQ ID NO 73
<211> LENGTH: 50
<212> TYPE: DNA
<213> ORGANISM: Artificial Sequence
<220> FEATURE:
<223> OTHER INFORMATION: synthetic oligonucleotide

<400> SEQUENCE: 73
ggtgaccaag ggtggctctt cgcctggctt tttacccttc gcctgggaca      50

<210> SEQ ID NO 74
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 74
ggtgaccaag ggtggcccct cacccttcgc ctgggaca      38

<210> SEQ ID NO 75
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 75
ggtgaccaag ggtggctcct ttcgcctggg aca      33

<210> SEQ ID NO 76
<211> LENGTH: 62
<212> TYPE: DNA
<213> ORGANISM: Artificial Sequence
<220> FEATURE:
<223> OTHER INFORMATION: synthetic oligonucleotide

<400> SEQUENCE: 76
ggtgaccaag ggtggctcct tacccttcgc ctggggtggc cctcaccct tcgcctggga      60 ca      62

<210> SEQ ID NO 77
<211> LENGTH: 62
<212> TYPE: DNA
<213> ORGANISM: Artificial Sequence
<220> FEATURE:
<223> OTHER INFORMATION: synthetic oligonucleotide

<400> SEQUENCE: 77
ggtgaccaag ggtggctgtt tacccttcgc ctggggtggc cctcaccct tcgcctggga      60 ca      62

<210> SEQ ID NO 78

```
<211> LENGTH: 81
<212> TYPE: DNA
<213> ORGANISM: Artificial Sequence
<220> FEATURE:
<223> OTHER INFORMATION: synthetic oligonucleotide

<400> SEQUENCE: 78
ggtgaccaag ggtggcccct tacccttcgc ctggggtggc ctttcaccct tcgcctggtt    60
tttcaccctt cgcctgggac a                                              81

<210> SEQ ID NO 79
<211> LENGTH: 24
<212> TYPE: DNA
<213> ORGANISM: Artificial Sequence
<220> FEATURE:
<223> OTHER INFORMATION: synthetic oligonucleotide

<400> SEQUENCE: 79
ggtgaccacc cttcgcctgg gaca                                           24

<210> SEQ ID NO 80
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 80
tccaggtgct gcagaaggga ttccatg                                        27

<210> SEQ ID NO 81
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 81
tccaggcgct gcagaaggga ttccatg                                        27

<210> SEQ ID NO 82
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 82
tccaggtggg attccatg                                                  18

<210> SEQ ID NO 83
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 83
tccaggtgtt gcagaaggga ttccatg                                        27

<210> SEQ ID NO 84
<211> LENGTH: 15
<212> TYPE: DNA
<213> ORGANISM: Artificial Sequence
<220> FEATURE:
<223> OTHER INFORMATION: synthetic oligonucleotide
```

```
<400> SEQUENCE: 84
tgaagggatt ccatg                                                     15

<210> SEQ ID NO 85
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 85
tccaggtgct gctgaaggga ttccatg                                        27

<210> SEQ ID NO 86
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 86
tccgcgcgct gctaaacgga ctccgtg                                        27

<210> SEQ ID NO 87
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 87
tccaggtgct acagaaggga ttccatg                                        27

<210> SEQ ID NO 88
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 88

Thr Lys Gly Gly Pro Leu Pro Phe Ala Trp Asp
1               5                   10

<210> SEQ ID NO 89
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 89
accaagggtg gcccctgcc cttcgcctgg gac                                  33

<210> SEQ ID NO 90
<211> LENGTH: 11
<212> TYPE: PRT
<213> ORGANISM: Artificial Sequence
<220> FEATURE:
<223> OTHER INFORMATION: synthetic polypeptide

<400> SEQUENCE: 90

Thr Lys Gly Gly Pro Ser Pro Phe Ala Trp Asp
1               5                   10
```

<210> SEQ ID NO 91
<211> LENGTH: 33
<212> TYPE: DNA
<213> ORGANISM: Artificial Sequence
<220> FEATURE:
<223> OTHER INFORMATION: synthetic oligonucleotide

<400> SEQUENCE: 91
accaagggtg gcccctcacc cttcgcctgg gac         33

<210> SEQ ID NO 92
<211> LENGTH: 10
<212> TYPE: PRT
<213> ORGANISM: Artificial Sequence
<220> FEATURE:
<223> OTHER INFORMATION: synthetic polypeptide

<400> SEQUENCE: 92

Thr Lys Gly Gly Pro Ser Pro Phe Ala Trp
1               5                   10

<210> SEQ ID NO 93
<211> LENGTH: 76
<212> TYPE: DNA
<213> ORGANISM: Artificial Sequence
<220> FEATURE:
<223> OTHER INFORMATION: synthetic oligonucleotide

<400> SEQUENCE: 93
accaagggtg gcccctcacc cttcgcctgg ggtggcccct caccttcgc ctggccctc         60 accttcgcc tgggac         76

<210> SEQ ID NO 94
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 94

His Tyr Leu Ser Thr Gln Ser
1               5

<210> SEQ ID NO 95
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 95
ccactacctg agcacccagt ccg         23

<210> SEQ ID NO 96
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 96

His Tyr Ser Ser Thr Gln Ser
1               5

<210> SEQ ID NO 97

```
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 97
ccactattca agtacccagt cgg                                             23

<210> SEQ ID NO 98
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 98
ccactattta agtacccagt cgg                                             23

<210> SEQ ID NO 99
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 99

Asn Ile Leu Gly His Lys Leu
1               5

<210> SEQ ID NO 100
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 100
caacatcctg gggcacaagc tgg                                             23

<210> SEQ ID NO 101
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 101

Asn Ile Ser Gly His Lys Leu
1               5

<210> SEQ ID NO 102
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 102
caacatttca gggcacaagc tgg                                             23

<210> SEQ ID NO 103
<211> LENGTH: 23
<212> TYPE: DNA
<213> ORGANISM: Artificial Sequence
<220> FEATURE:
<223> OTHER INFORMATION: synthetic oligonucleotide
```

<400> SEQUENCE: 103 caacattta gggcacaagc tgg                                               23

<210> SEQ ID NO 104
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 104

Glu Gly Tyr Val Gln Gly Arg
1               5

<210> SEQ ID NO 105
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 105
ccgaaggcta cgtccaggag cgc                                              23

<210> SEQ ID NO 106
<211> LENGTH: 7
<212> TYPE: PRT
<213> ORGANISM: Artificial Sequence
<220> FEATURE:
<223> OTHER INFORMATION: synthetic polypeptide

<400> SEQUENCE: 106

Glu Gly His Val Gln Gly Arg
1               5

<210> SEQ ID NO 107
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 107
ccgaaggtca cgtacaggag cgg                                              23

<210> SEQ ID NO 108
<211> LENGTH: 23
<212> TYPE: DNA
<213> ORGANISM: Artificial Sequence
<220> FEATURE:
<223> OTHER INFORMATION: synthetic oligonucleotide

<400> SEQUENCE: 108
ccgaaggtta cgtacaggag cgg                                              23

<210> SEQ ID NO 109
<211> LENGTH: 103
<212> TYPE: DNA
<213> ORGANISM: Artificial Sequence
<220> FEATURE:
<223> OTHER INFORMATION: synthetic oligonucleotide

<400> SEQUENCE: 109 acaccccat cggcgacggc cccgtgctgc tgcccgacaa ccactattca agtacccagt        60

```
cggccctgag caaagacccc aacgagaagc gcgatcacat ggt              103
```

<210> SEQ ID NO 110
<211> LENGTH: 103
<212> TYPE: DNA
<213> ORGANISM: Artificial Sequence
<220> FEATURE:
<223> OTHER INFORMATION: synthetic oligonucleotide

<400> SEQUENCE: 110

```
acaccccccat cggcgacggc cccgtgctgc tgcccgacaa ccattattta agtacccagt   60
cggccctgag caaagacccc aacgagaagc gcgatcacat ggt                     103
```

<210> SEQ ID NO 111
<211> LENGTH: 103
<212> TYPE: DNA
<213> ORGANISM: Artificial Sequence
<220> FEATURE:
<223> OTHER INFORMATION: synthetic oligonucleotide

<400> SEQUENCE: 111

```
acaccccccat tggcgacggc cccgtgctgc tgcccgacaa ccattattta agtacccagt   60
cggccctgag caaagacccc aacgagaagc gcgatcacat ggt                     103
```

<210> SEQ ID NO 112
<211> LENGTH: 103
<212> TYPE: DNA
<213> ORGANISM: Artificial Sequence
<220> FEATURE:
<223> OTHER INFORMATION: synthetic oligonucleotide

<400> SEQUENCE: 112

```
acaccccccat cggcgacggc cccgtgctgc tgcccgacaa ccactattta agtacccagt   60
cggccctgag caaagacccc aacgagaagc gcgatcacat ggt                     103
```

<210> SEQ ID NO 113
<211> LENGTH: 98
<212> TYPE: DNA
<213> ORGANISM: Artificial Sequence
<220> FEATURE:
<223> OTHER INFORMATION: synthetic oligonucleotide

<400> SEQUENCE: 113

```
acaccccccat cggcgacggc cccgtgctgc tgcccgacaa ccactagtac ccagtcggcc   60
ctgagcaaag accccaacga gaagcgcgat cacatggt                           98
```

<210> SEQ ID NO 114
<211> LENGTH: 67
<212> TYPE: DNA
<213> ORGANISM: Artificial Sequence
<220> FEATURE:
<223> OTHER INFORMATION: synthetic oligonucleotide

<400> SEQUENCE: 114

```
acaccccccat cggcgacggc cccgtgctgc tgagcaaaga ccccaacgag aagcgcgatc   60
acatggt                                                              67
```

<210> SEQ ID NO 115
<211> LENGTH: 103
<212> TYPE: DNA
<213> ORGANISM: Artificial Sequence
<220> FEATURE:
<223> OTHER INFORMATION: synthetic oligonucleotide

<400> SEQUENCE: 115
accgcatcga gctgaagggc atcgacttca aggaggacgg caacatttca gggcacaagc    60
tggagtacaa ctacaacagc cacaacgtct atatcatggc cga    103

<210> SEQ ID NO 116
<211> LENGTH: 103
<212> TYPE: DNA
<213> ORGANISM: Artificial Sequence
<220> FEATURE:
<223> OTHER INFORMATION: synthetic oligonucleotide

<400> SEQUENCE: 116
accgcatcga gctgaagggc atcgacttca aggaggacgg caacatttta gggcacaagc    60
tggagtacaa ctacaacagc cacaacgtct atatcatggc cga    103

<210> SEQ ID NO 117
<211> LENGTH: 103
<212> TYPE: DNA
<213> ORGANISM: Artificial Sequence
<220> FEATURE:
<223> OTHER INFORMATION: synthetic oligonucleotide

<400> SEQUENCE: 117
accgcatcga gctgaagggc atcgacttta aggaggacgg caacatttta gggcacaagc    60
tggagtacaa ctacaacagc cacaacgtct atatcatggc cga    103

<210> SEQ ID NO 118
<211> LENGTH: 102
<212> TYPE: DNA
<213> ORGANISM: Artificial Sequence
<220> FEATURE:
<223> OTHER INFORMATION: synthetic oligonucleotide

<400> SEQUENCE: 118
accgcatcga gctgaagggc atcgacttga aggaggacgg caacatttag ggcacaagct    60
ggagtacaac tacaacagcc acaacgtcta tatcatggcc ga    102

<210> SEQ ID NO 119
<211> LENGTH: 93
<212> TYPE: DNA
<213> ORGANISM: Artificial Sequence
<220> FEATURE:
<223> OTHER INFORMATION: synthetic oligonucleotide

<400> SEQUENCE: 119
accgcatcga gctgaagggc atcgacttca aggaggacgg caacacaagc tggagtacaa    60
ctacaacagc cacaacgtct atatcatggc cga    93

<210> SEQ ID NO 120
<211> LENGTH: 99
<212> TYPE: DNA
<213> ORGANISM: Artificial Sequence
<220> FEATURE:
<223> OTHER INFORMATION: synthetic oligonucleotide

<400> SEQUENCE: 120
accgcatcga gctgaagggc atcgacttca aggaggacgg caacaagggc acaagctgga    60
gtacaactac aacagccaca acgtctatat catggccga    99

<210> SEQ ID NO 121

-continued

```
<211> LENGTH: 73
<212> TYPE: DNA
<213> ORGANISM: Artificial Sequence
<220> FEATURE:
<223> OTHER INFORMATION: synthetic oligonucleotide

<400> SEQUENCE: 121
accgcatcga gctgaagggc atcgacaagc tggagtacaa ctacaacagc cacaacgtct      60
atatcatggc cga                                                        73

<210> SEQ ID NO 122
<211> LENGTH: 103
<212> TYPE: DNA
<213> ORGANISM: Artificial Sequence
<220> FEATURE:
<223> OTHER INFORMATION: synthetic oligonucleotide

<400> SEQUENCE: 122
accgcatcga gctgaagggc atcgacttta aggagaacgg caacatttta gggcacaagc      60
tggagtacaa ctacaacagc cacaacgtct atatcatggc cga                      103

<210> SEQ ID NO 123
<211> LENGTH: 103
<212> TYPE: DNA
<213> ORGANISM: Artificial Sequence
<220> FEATURE:
<223> OTHER INFORMATION: synthetic oligonucleotide

<400> SEQUENCE: 123
accgcatcga gctgaagggc atcgacttca aggaggacgg caatatttta gggcacaagc      60
tggagtacaa ctacaacagc cacaacgtct atatcatggc cga                      103

<210> SEQ ID NO 124
<211> LENGTH: 103
<212> TYPE: DNA
<213> ORGANISM: Artificial Sequence
<220> FEATURE:
<223> OTHER INFORMATION: synthetic oligonucleotide

<400> SEQUENCE: 124
accgcatcca gctcaagggc atcgactttta aggaaaacgg caatatttta gggcacaagc     60
tggagtacaa ctacaacagc cacaacgtct atatcatggc cga                      103

<210> SEQ ID NO 125
<211> LENGTH: 9434
<212> TYPE: DNA
<213> ORGANISM: Artificial Sequence
<220> FEATURE:
<223> OTHER INFORMATION: synthetic oligonucleotide

<400> SEQUENCE: 125
atatgccaag tacgcccccct attgacgtca atgacggtaa atggcccgcc tggcattatg     60
cccagtacat gaccttatgg gactttccta cttggcagta catctacgta ttagtcatcg    120
ctattaccat ggtgatgcgg ttttggcagt acatcaatgg gcgtggatag cggtttgact    180
cacggggatt tccaagtctc cacccccattg acgtcaatgg gagtttgttt tggcaccaaa   240
atcaacggga ctttccaaaa tgtcgtaaca actccgcccc attgacgcaa atgggcggta    300
ggcgtgtacg gtgggaggtc tatataagca gagctggttt agtgaaccgt cagatccgct    360
agagatccgc ggccgctaat acgactcact atagggagag ccgccaccat gagctcagag    420
actggcccag tggctgtgga ccccacattg aggtgagtcc aggagatgtt tcagcactgt    480
```

| | |
|---|---|
| tgcctttagt ctcgaggcaa cttagacaac tgagtattga tctgagcaca gcagggtgtg | 540 |
| agctgtttga agatactggg gttggggtga agaaactgc agaggactaa ctgggctgag | 600 |
| acccagtggc aatgttttag ggcctaagga atgcctctga aaatctagat ggacaacttt | 660 |
| gactttgaga aaagagaggt ggaaatgagg aaaatgactt ttctttatta gatttcggta | 720 |
| gaaagaactt tcatctttcc cctattttg ttattcgttt taaaacatct atctggaggc | 780 |
| aggacaagta tggtcattaa aaagatgcag gcagaaggca tatattggct cagtcaaagt | 840 |
| ggggaacttt ggtggccaaa catacattgc taaggctatt cctatatcag ctggacacat | 900 |
| ataaaatgct gctaatgctt cattacaaac ttatatcctt taattccaga tgggggcaaa | 960 |
| gtatgtccag gggtgaggaa caattgaaac atttgggctg gagtagattt tgaaagtcag | 1020 |
| ctctgtgtgt gtgtgtgtgt gtgtgtgtgt gtgtgtgtgc gcgcacgtgt gtttgtgtgt | 1080 |
| gtgtgagagc gtgtgtttct tttaacgttt tcagcctaca gcatacaggg ttcatggtgg | 1140 |
| caagaagata acaagattta aattatggcc agtgactagt gctgcaagaa gaacaactac | 1200 |
| ctgcatttaa tgggaaagca aaatctcagg cttttgaggga agttaacata ggcttgattc | 1260 |
| tgggtggaag ctgggtgtgt agttatctgg aggccaggct ggagctctca gctcactatg | 1320 |
| ggttcatctt tattgtctcc tttcatctca acagacggcg gatcgagccc catgagtttg | 1380 |
| aggtattctt cgatccgaga gagctccgca aggagacctg cctgctttac gaaattaatt | 1440 |
| gggggggccg gcactccatt tggcgacata catcacagaa cactaacaag cacgtcgaag | 1500 |
| tcaacttcat cgagaagttc acgacagaaa gatatttctg tccgaacaca aggtgcagca | 1560 |
| ttacctggtt tctcagctgg agcccatgcg gcgaatgtag tagggccatc actgaattcc | 1620 |
| tgtcaaggta tccccacgtc actctgttta tttacatcgc aaggctgtac caccacgctg | 1680 |
| acccccgcaa tcgacaaggc ctgcgggatt tgatctcttc aggtgtgact atccaaatta | 1740 |
| tgactgagca ggagtcagga tactgctgga gaaactttgt gaattatagc ccgagtaatg | 1800 |
| aagcccactg gcctaggtat ccccatctgt gggtacgact gtacgttctt gaactgtact | 1860 |
| gcatcatact gggcctgcct ccttgtctca acattctgag aaggaagcag ccacagctga | 1920 |
| cattctttac catcgctctt cagtcttgtc attaccagcg actgccccca cacattctct | 1980 |
| gggccaccgg gttgaaaagc ggcagcgaga ctcccgggac ctcagagtcc gccacacccg | 2040 |
| aaagtgataa aaagtattct attggttag ccatcggcac taattccgtt ggatgggctg | 2100 |
| tcataaccga tgaatacaaa gtaccttcaa agaaatttaa ggtgttgggg aacacagacc | 2160 |
| gtcattcgat taaaaagaat cttatcggtg ccctcctatt cgatagtggc gaaacggcag | 2220 |
| aggcgactcg cctgaaacga accgctcgga gaaggtatac acgtcgcaag aaccgaatat | 2280 |
| gttacttaca agaatttttt agcaatgaga tggccaaagt tgacgattct ttctttcacc | 2340 |
| gtttggaaga gtccttcctt gtcgaagagg acaagaaaca tgaacggcac cccatctttg | 2400 |
| gaaacatagt agatgaggtg gcatatcatg aaaagtaccc aacgatttat cacctcagaa | 2460 |
| aaaagctagt tgactcaact gataaagcgg acctgaggtt aatctacttg gctcttgccc | 2520 |
| atatgataaa gttccgtggg cactttctca ttgagggtga tctaaatccg gacaactcgg | 2580 |
| atgtcgacaa actgttcatc cagttagtac aaacctataa tcagttgttt gaagagaacc | 2640 |
| ctataaatgc aagtggcgtg gatgcgaagg ctattcttag cgcccgcctc tctaaatccc | 2700 |
| gacggctaga aaacctgatc gcacaattac ccggagagaa gaaaaatggg ttgttcggta | 2760 |
| accttatagc gctctcacta ggcctgacac caaatttaa gtcgaacttc gacttagctg | 2820 |

-continued

```
aagatgccaa attgcagctt agtaaggaca cgtacgatga cgatctcgac aatctactgg    2880
cacaaattgg agatcagtat gcggacttat ttttggctgc caaaaaccct agcgatgcaa    2940
tcctcctatc tgacatactg agagttaata ctgagattac caaggcgccg ttatccgctt    3000
caatgatcaa aaggtacgat gaacatcacc aagacttgac acttctcaag gccctagtcc    3060
gtcagcaact gcctgagaaa tataaggaaa tattctttga tcagtcgaaa aacgggtacg    3120
caggttatat tgacggcgga gcgagtcaag aggaattcta caagtttatc aaacccatat    3180
tagagaagat ggatgggacg gaagagttgc ttgtaaaact caatcgcgaa gatctactgc    3240
gaaagcagcg gactttcgac aacggtagca ttccacatca aatccactta ggcgaattgc    3300
atgctatact tagaaggcag gaggattttt atccgttcct caaagacaat cgtgaaaaga    3360
ttgagaaaat cctaaccttt cgcataccct actatgtggg accctgcc cgagggaact     3420 ctcggttcgc atggatgaca agaaagtccg aagaaacgat tactccatgg aattttgagg    3480
aagttgtcga taaaggtgcg tcagctcaat cgttcatcga gaggatgacc aactttgaca    3540
agaatttacc gaacgaaaaa gtattgccta agcacagttt actttacgag tatttcacag    3600
tgtacaatga actcacgaaa gttaagtatg tcactgaggg catgcgtaaa cccgccttc    3660 taagcggaga acagaagaaa gcaatagtag atctgttatt caagaccaac cgcaaagtga    3720
cagttaagca attgaaagag gactacttta agaaaattga atgcttcgat tctgtcgaga    3780
tctccggggt agaagatcga tttaatgcgt cacttggtac gtatcatgac ctcctaaaga    3840
taattaaaga taaggacttc ctggataacg aagagaatga agatatctta gaagatatag    3900
tgttgactct taccctcttt gaagatcggg aaatgattga ggaaagacta aaaacatacg    3960
ctcacctgtt cgacgataag gttatgaaac agttaaagag gcgtcgctat acgggctggg    4020
gacgattgtc gcggaaactt atcaacggga taagagacaa gcaaagtggt aaaactattc    4080
tcgattttct aaagagcgac ggcttcgcca ataggaactt tatgcagctg atccatgatg    4140
actctttaac cttcaaagag gatatacaaa aggcacaggt ttccggacaa ggggactcat    4200
tgcacgaaca tattgcgaat cttgctggtt cgccagccat caaaaagggc atactccaga    4260
cagtcaaagt agtggatgag ctagttaagg tcatgggacg tcacaaaccg gaaaacattg    4320
taatcgagat ggcacgcgaa aatcaaacga ctcagaaggg gcaaaaaaac agtcgagagc    4380
ggatgaagag aatagaagag ggtattaaag aactgggcag ccagatctta aaggagcatc    4440
ctgtggaaaa taccccaattg cagaacgaga aactttacct ctattaccta caaaatggaa    4500
gggacatgta tgttgatcag gaactggaca taaaccgttt atctgattac gacgtcgatc    4560
acattgtacc ccaatccttt ttgaaggacg attcaatcga caataaagtg cttacacgct    4620
cggataagaa ccgagggaaa agtgacaatg ttccaagcga ggaagtcgta aagaaaatga    4680
agaactattg gcggcagctc ctaaatgcga aactgataac gcaaagaaag ttcgataact    4740
taactaaagc tgagagggt ggcttgtctg aacttgacaa ggccggattt attaaacgtc    4800
agctcgtgga aacccgccaa atcacaaagc atgttgcaca gatactagat tcccgaatga    4860
atacgaaata cgacgagaac gataagctga ttcgggaagt caaagtaatc actttaaagt    4920
caaaattggt gtcggacttc agaaaggatt ttcaattcta taaagttagg gagataaata    4980
actaccacca tgcgcacgac gcttatctta atgccgtcgt agggaccgca ctcattaaga    5040
aatacccgaa gctagaaagt gagtttgtgt atggtgatta caaagtttat gacgtccgta    5100
agatgatcgc gaaaagcgaa caggagatag gcaaggctac agccaaatac ttcttttatt    5160
ctaacattat gaatttcttt aagacggaaa tcactctggc aaacggagag atacgcaaac    5220
```

```
gacctttaat tgaaaccaat ggggagacag gtgaaatcgt atgggataag ggccgggact    5280
tcgcgacggt gagaaaagtt ttgtccatgc cccaagtcaa catagtaaag aaaactgagg    5340
tgcagaccgg agggttttca aaggaatcga ttcttccaaa aaggaatagt gataagctca    5400
tcgctcgtaa aaaggactgg gacccgaaaa agtacggtgg cttcgatagc cctacagttg    5460
cctattctgt cctagtagtg gcaaaagttg agaagggaaa atccaagaaa ctgaagtcag    5520
tcaaagaatt attggggata acgattatgg agcgctcgtc ttttgaaaag aaccccatcg    5580
acttccttga ggcgaaaggt tacaaggaag taaaaaagga tctcataatt aaactaccaa    5640
agtatagtct gtttgagtta gaaaatggcc gaaaacggat gttggctagc gccggagagc    5700
ttcaaaaggg gaacgaactc gcactaccgt ctaaatacgt gaatttcctg tatttagcgt    5760
cccattacga gaagttgaaa ggttcacctg aagataacga acagaagcaa ctttttgttg    5820
agcagcacaa acattatctc gacgaaatca tagagcaaat ttcggaattc agtaagagag    5880
tcatcctagc tgatgccaat ctggacaaag tattaagcgc atacaacaag cacagggata    5940
aacccatacg tgagcaggcg gaaaatatta tccatttgtt tactcttacc aacctcggcg    6000
ctccagccgc attcaagtat tttgacacaa cgatagatcg caaacgatac acttctacca    6060
aggaggtgct agacgcgaca ctgattcacc aatccatcac gggattatat gaaactcgga    6120
tagatttgtc acagcttggg ggtgactctg gtgttctac taatctgtca gatattattg    6180
aaaaggagac cggtaagcaa ctggttatcc aggaatccat cctcatgctc ccagaggagg    6240
tggaagaagt cattgggaac aagccggaaa gcgatatact cgtgcacacc gcctacgacg    6300
agagcaccga cgagaatgtc atgcttctga ctagcgacgc ccctgaatac aagccttggg    6360
ctctggtcat acaggatagc aacggtgaga caagattaa gatgctctct ggtggttctc    6420
ccaagaagaa gaggaaagtc taaccggtca tcatcaccat caccattgag tttaaacccg    6480
ctgatcagcc tcgactgtgc cttctagttg ccagccatct gttgtttgcc cctccccgt    6540 gccttccttg accctggaag gtgccactcc cactgtcctt tcctaataaa atgaggaaat    6600
tgcatcgcat tgtctgagta ggtgtcattc tattctgggg ggtggggtgg ggcaggacag    6660 caaggggag gattgggaag acaatagcag gcatgctggg gatgcggtgg gctctatggc    6720
ttctgaggcg gaaagaacca gctgggctc gataccgtcg acctctagct agagcttggc    6780
gtaatcatgg tcatagctgt ttcctgtgtg aaattgttat ccgctcacaa ttccacacaa    6840
catacgagcc ggaagcataa agtgtaaagc ctagggtgcc taatgagtga gctaactcac    6900
attaattgcg ttgcgctcac tgcccgcttt ccagtcggga aacctgtcgt gccagctgca    6960
ttaatgaatc ggccaacgcg cggggagagg cggtttgcgt attgggcgct cttccgcttc    7020
ctcgctcact gactcgctgc gctcggtcgt tcggctgcgg cgagcggtat cagctcactc    7080
aaaggcggta atacggttat ccacagaatc aggggataac gcaggaaaga acatgtgagc    7140
aaaaggccag caaaaggcca ggaaccgtaa aaaggccgcg ttgctggcgt ttttccatag    7200
gctccgcccc cctgacgagc atcacaaaaa tcgacgctca agtcagaggt ggcgaaaccc    7260
gacaggacta taaagatacc aggcgtttcc ccctggaagc tccctcgtgc gctctcctgt    7320
tccgaccctg ccgcttaccg gatacctgtc cgcctttctc ccttcgggaa gcgtggcgct    7380
ttctcatagc tcacgctgta ggtatctcag ttcggtgtag tcgttcgct ccaagctggg    7440 ctgtgtgcac gaaccccccg ttcagcccga ccgctgcgcc ttatccggta actatcgtct    7500
tgagtccaac ccggtaagac acgacttatc gccactggca gcagccactg gtaacaggat    7560
```

```
tagcagagcg aggtatgtag gcggtgctac agagttcttg aagtggtggc ctaactacgg    7620
ctacactaga agaacagtat ttggtatctg cgctctgctg aagccagtta ccttcggaaa    7680
aagagttggt agctcttgat ccggcaaaca aaccaccgct ggtagcggtg gttttttgt     7740 ttgcaagcag cagattacgc gcagaaaaaa aggatctcaa gaagatcctt tgatcttttc    7800
tacggggtct gacgctcagt ggaacgaaaa ctcacgttaa gggattttgg tcatgagatt    7860
atcaaaaagg atcttcacct agatcctttt aaattaaaaa tgaagtttta aatcaatcta    7920
aagtatatat gagtaaactt ggtctgacag ttaccaatgc ttaatcagtg aggcacctat    7980
ctcagcgatc tgtctatttc gttcatccat agttgcctga ctccccgtcg tgtagataac    8040
tacgatacgg gagggcttac catctggccc cagtgctgca atgataccgc gagacccacg    8100
ctcaccggct ccagatttat cagcaataaa ccagccagcc ggaagggccg agcgcagaag    8160
tggtcctgca actttatccg cctccatcca gtctattaat tgttgccggg aagctagagt    8220
aagtagttcg ccagttaata gtttgcgcaa cgttgttgcc attgctacag gcatcgtggt    8280
gtcacgctcg tcgtttggta tggcttcatt cagctccggt tcccaacgat caaggcgagt    8340
tacatgatcc cccatgttgt gcaaaaaagc ggttagctcc ttcggtcctc cgatcgttgt    8400
cagaagtaag ttggccgcag tgttatcact catggttatg gcagcactgc ataattctct    8460
tactgtcatg ccatccgtaa gatgcttttc tgtgactggt gagtactcaa ccaagtcatt    8520
ctgagaatag tgtatgcggc gaccgagttg ctcttgcccg gcgtcaatac gggataatac    8580
cgcgccacat agcagaactt taaaagtgct catcattgga aaacgttctt cggggcgaaa    8640
actctcaagg atcttaccgc tgttgagatc cagttcgatg taacccactc gtgcacccaa    8700
ctgatcttca gcatctttta ctttcaccag cgtttctggg tgagcaaaaa caggaaggca    8760
aaatgccgca aaaagggaa taagggcgac acggaaatgt tgaatactca tactcttcct    8820
ttttcaatat tattgaagca tttatcaggg ttattgtctc atgagcggat acatatttga    8880
atgtatttag aaaaataaac aaatagggggt tccgcgcaca tttccccgaa aagtgccacc    8940
tgacgtcgac ggatcgggag atcgatctcc cgatcccta gggtcgactc tcagtacaat    9000
ctgctctgat gccgcatagt taagccagta tctgctccct gcttgtgtgt tggaggtcgc    9060
tgagtagtgc gcgagcaaaa tttaagctac aacaaggcaa ggcttgaccg acaattgcat    9120
gaagaatctg cttagggtta ggcgttttgc gctgcttcgc gatgtacggg ccagatatac    9180
gcgttgacat tgattattga ctagttatta atagtaatca attacggggt cattagttca    9240
tagcccatat atggagttcc gcgttacata acttacggta aatggcccgc ctggctgacc    9300
gcccaacgac ccccgcccat tgacgtcaat aatgacgtat gttcccatag taacgccaat    9360
agggactttc cattgacgtc aatgggtgga gtatttacgg taaactgccc acttggcagt    9420
acatcaagtg tatc                                                      9434
```

REAL-TIME REPORTER SYSTEMS FOR MONITORING BASE EDITING

CROSS-REFERENCE TO RELATED APPLICATIONS

This application claims benefit of priority from U.S. Provisional Application No. 62/532,064, filed on Jul. 13, 2017.

STATEMENT AS TO FEDERALLY SPONSORED RESEARCH

This invention was made with government support under GM118000, AI064046, and CA206309 awarded by the National Institutes of Health. The government has certain rights in the invention.

SEQUENCE LISTING

This application includes a Sequence Listing that has been submitted electronically as an ASCII text file named 09531 0401001 ST25.txt. The ASCII text file, created on Jul. 12, 2018, is 102 kilobytes in size. The material in the ASCII text file is hereby incorporated by reference in its entirety.

TECHNICAL FIELD

This document relates to materials and methods for real-time monitoring base editing in living cells, and particularly to a real-time reporter for monitoring base editing by APOBEC-Cas9 fusions.

BACKGROUND

Single base editing is an exciting application for clustered regularly interspaced short palindromic repeats (CRISPR) technology. Single C-to-T mutations in genomic DNA can be achieved using ribonucleoprotein complexes containing, for example, an apolipoprotein B mRNA editing enzyme, catalytic polypeptide-like-1 (APOBEC1) single-stranded DNA deaminase, a CRISPR-associated-9 (Cas9) nickase (Cas9n), a uracil DNA glycosylase inhibitor (UGI), and guide RNA (gRNA). The main experimental readout for base editing to date is DNA sequencing, which can be cumbersome and expensive, and is not amenable to screening and optimization.

SUMMARY

This document is based, at least in part, on the development of a real-time reporter for quantification of single base editing in living human cells, and also on the development of next-generation editing constructs that achieve higher editing frequencies. As described herein, for example, mutation of a single APOBEC hotspot, 5'-TCA-to-TTA (5'-UCA-to-UUA in RNA), can restore fluorescence to a first reporter (e.g., enhanced green fluorescent protein; eGFP) marked by a second reporter (e.g., mCherry), which enables editing frequencies to be quantified based on the ratio of first reporter-positive to second reporter-positive cells. Such systems are referred to herein as APOBEC-Mediated Base-Editing Reporter ("AMBER") systems. In some cases, mutation of an APOBEC hotspot, 5'-TCA-to-TTA (5'-UCA-to-UUA in RNA), can restore fluorescence to a first reporter (e.g., mCherry) marked by a second reporter (e.g., enhanced green fluorescent protein; eGFP), which enables editing frequencies to be quantified based on the ratio of first reporter-positive to second reporter-positive cells. As described herein, a reporter system with mCherry as the first reporter also quantified the DNA cleavage activity of Cas9, and may therefore also be adaptable for use with different CRISPR systems. Because it can be used to monitor both APOBEC- and Cas9-mediated Editing in real time, this type of reporter is referred to herein as "ACE". The combination of a rapid, fluorescence-based base editing reporter system and more efficient, structurally defined DNA editing enzymes provides a strong foundation for optimization, and ultimately for tailoring editosome complexes to target single cytosine nucleobases with negligible off-target effects.

In a first aspect, this document features a nucleic acid containing: a first nucleotide sequence encoding a first reporter, where the first reporter is inactivated by a revertible mutation within the nucleotide sequence encoding the first reporter, as compared to a reference sequence for the first reporter, and where the mutation can be reverted by a base editing complex; and a second nucleotide sequence encoding a second reporter that is active when it is expressed, where the first and second nucleotide sequences are operably linked to one or more promoters that drive expression of the first and second nucleotide sequences, and where the first and second nucleotide sequences are separated by a nucleotide sequence encoding a self-cleaving peptide. The revertible mutation can include a point mutation. The point mutation can be a thymine to cytosine mutation (e.g., a thymine to cytosine mutation that results in a TCA motif). The first and second reporters can be fluorescent reporter polypeptides. The first reporter or the second reporter can be a mCherry polypeptide. The first reporter can be a mCherry polypeptide containing the amino acid sequence set forth in SEQ ID NO:2, with the proviso that the leucine residue at position 56 of SEQ ID NO:2 is replaced with a serine residue. The serine residue can be encoded by a TCA codon. The second reporter can be a mCherry polypeptide containing the amino acid sequence set forth in SEQ ID NO:2. The first or second reporter can be a green fluorescent protein (GFP) polypeptide. The GFP polypeptide can be an enhanced GFP (eGFP) polypeptide. The first reporter can be an eGFP polypeptide containing the amino acid sequence set forth in SEQ ID NO:4, with the proviso that the leucine residue at position 202 of SEQ ID NO:4 is replaced with a serine residue, the leucine residue at position 138 of SEQ ID NO:4 is replaced by a serine residue, or the tyrosine at position 93 of SEQ ID NO:4 is replaced by a histidine residue. The serine residue at position 202 or position 138 can be encoded by a TCA codon, and the histidine at position 93 can be encoded by a CAC codon. The second reporter can be an eGFP polypeptide containing the amino acid sequence set forth in SEQ ID NO:4. The self-cleaving polypeptide can be a T2A polypeptide. The first and second nucleotide sequences can be operably linked to a single promoter, or can be operably linked to separate promoters. The revertible mutation can be a point mutation that can be reverted by a base editing complex containing an apolipoprotein B mRNA-editing complex (APOBEC) polypeptide, or a portion thereof. The APOBEC polypeptide can be rat APOBEC1 or a portion thereof, human APOBEC3A or a portion thereof, human APOBEC3B or a portion thereof, or human APOBEC3H or a portion thereof. For example, the APOBEC polypeptide can be a human APOBEC3B C-terminal domain. The base editing complex can include an APOBEC polypeptide, a Clustered Regularly Interspersed Short Palindromic Repeats (CRISPR)-associated-9 (Cas9) polypeptide, and a uracil DNA glycosylase inhibitor (UGI).

This document also features vectors containing the nucleic acids described herein. In another aspect, this document features a method that includes: (a) introducing into a cell a base editing fusion polypeptide or a nucleic acid encoding the fusion polypeptide, where the fusion polypeptide includes (i) a first portion containing an APOBEC polypeptide having single-stranded DNA cytosine deaminase activity, and (ii) a second portion containing a Cas9 polypeptide having the ability to complex with a CRISPR guide RNA (gRNA), but lacking nuclease activity; (b) introducing into the cell a nucleic acid containing (i) a first nucleotide sequence encoding a first reporter, where the first reporter is inactivated by a revertible mutation, where the revertible mutation can be reverted by the base editing fusion polypeptide, and (ii) a second nucleotide sequence encoding a second reporter, where the first and second nucleotide sequences are operably linked to one or more promoters that drive expression of the first and second nucleotide sequences, and where the first and second nucleotide sequences are separated by a nucleotide sequence encoding a self-cleaving peptide; (c) detecting a first signal generated by the first reporter and a second signal generated by the second reporter; and (d) determining a ratio of the first signal to the second signal, or determining a ratio of the second signal to the first signal. The revertible mutation can include a point mutation. The point mutation can be a thymine to cytosine mutation (e.g., a thymine to cytosine mutation that results in a TCA motif). The first and second reporters can be fluorescent reporter polypeptides. The first reporter or the second reporter can be a mCherry polypeptide. The first reporter can be a mCherry polypeptide containing the amino acid sequence set forth in SEQ ID NO:2, with the proviso that the leucine residue at position 56 of SEQ ID NO:2 is replaced with a serine residue. The serine residue can be encoded by a TCA codon. The second reporter can be a mCherry polypeptide containing the amino acid sequence set forth in SEQ ID NO:2. The first or second reporter can be a GFP polypeptide. The GFP polypeptide can be an eGFP polypeptide. The first reporter can be an eGFP polypeptide containing the amino acid sequence set forth in SEQ ID NO:4, with the proviso that the leucine residue at position 202 of SEQ ID NO:4 is replaced with a serine residue, the leucine residue at position 138 of SEQ ID NO:4 is replaced by a serine residue, or the tyrosine at position 93 of SEQ ID NO:4 is replaced by a histidine residue. The serine residue at position 202 or position 138 can be encoded by a TCA codon, and the histidine at position 93 can be encoded by a CAC codon. The second reporter can be an eGFP polypeptide containing the amino acid sequence set forth in SEQ ID NO:4. The self-cleaving polypeptide can be a T2A polypeptide. The first and second nucleotide sequences can be operably linked to a single promoter, or can be operably linked to separate promoters. The APOBEC polypeptide can be rat APOBEC1 or a portion thereof, human APOBEC3A or a portion thereof, human APOBEC3B or a portion thereof, or human APOBEC3H or a portion thereof. For example, the APOBEC polypeptide can be a human APOBEC3B C-terminal domain. The base editing fusion polypeptide can further contain a UGI.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1A is a schematic of an APOBEC-Cas9/gRNA editosome engaging a DNA target. C-to-T editing (changing a TCA codon into a TTA codon) occurs in the ssDNA loop displaced by Cas9-mediated gRNA annealing to target DNA. The non-edited strand is broken by the Cas9 nickase, which targets DNA repair mechanisms (not shown) to the nicked strand and facilitates conversion of the uracil lesion into a thymine mutation. FIG. 1B is a schematic of the ACE system in the context of a lentiviral construct with a CMV promoter that drives expression of a bicistronic message encoding mutant mCherry and wild-type eGFP. Reversion of 5'-TCA (Ser59) to 5'-TTA (Leu59) by APOBEC-mediated editing restores mCherry fluorescence. FIG. 1C is a schematic of the ACE reporter in the context of a lentiviral construct with a CMV promoter that drives expression of a bicistronic message encoding mutant mCherry and wild-type eGFP. The sequence of the gRNA displaced DNA strand (SEQ ID NO:62) is shown below with flanking APOBEC 5'-TCA deamination hotspots boxed, and protospacer adjacent motif (PAM) sites and 43 bp insertion labeled. The sequence after editing (SEQ ID NO:63) also is shown. Ribbon schematics depict the defective mCherry and functionally restored mCherry with the flexible loop position of residue 59 shown (model based on pdb 2H5Q). FIG. 1D contains representative images of Cherry-positive cells catalyzed by BE3 (a rat APOBEC1-Cas9n-UGI fusion) and mCherry codon 59-directed gRNA (top panels). Cherry-positive cells were not observed with a non-specific (NS) gRNA (bottom panels). White bar=30 FIG. 1E is a graph plotting quantification of the base editing experiment in FIG. 1D (n=3; average+/−SD). FIG. 1F is a ribbon schematic of the mCherry structure with a zoom-in highlighting essential interactions between Leu59 and β-barrel residues required for fluorescence (Leu59 is labeled Leu54 in the mCherry Protein Data Bank structure PDB 2H5Q). FIG. 1G is a graph plotting base editing activity catalyzed by BE3 in transfected HeLa cells (n=3; average±SD).

FIG. 2A contains representative fluorescent microscopy images of ACE-activated, mCherry-positive 293T cells catalyzed by human A3A, human A3Bctd, or rat APOBEC1 editosomes as indicated (mCherry codon 59-directed gRNA versus NS gRNA). Inset white bar=30 μm. The top portion of FIG. 2B is a graph plotting quantification of the experiment in FIG. 2A, together with two independent parallel experiments (n=3; average±SD). The bottom portion of FIG. 2B is an image showing the corresponding immunoblots of expressed APOBEC-Cas9-UGI constructs and HSP90 as a loading control (low and high exposures to help visualize BE3). FIG. 2C is a graph plotting the time course of ACE activity in 293T cells catalyzed by A3A, A3Bctd, or APOBEC1 editosomes (mCherry codon 59-directed gRNA versus NS-gRNA; n=3; mean+/−SD; error bars smaller than symbols are not shown). The top portion of FIG. 2D is a graph plotting titration data for 293T cells co-transfected with the ACE reporter, mCherry codon 59-directed gRNA, and different amounts of the indicated editosome constructs (100-600 ng; n=3; mean±SD). BE3i includes an intron in the rat APOBEC1 portion of the construct, identical to the intron required for propagation of A3A and A3Bctd constructs in *E. coli* and for expression in mammalian cells. The corresponding immunoblots are shown below the graph.

FIGS. 3A-3C show chromosomal DNA editing by A3A and A3Bctd editosomes. FIG. 3A is a graph plotting the level of base editing of a single copy genomic ACE reporter by the indicated editosomes in 293T and HeLa cells (n=3; average±SD). FIG. 3B shows immunoblots corresponding to the representative experiment plotted in FIG. 3A, showing APOBEC-Cas9n-UGI expression levels and HSP90 as a loading control. FIG. 3C shows Sanger sequencing results for the gRNA-binding region of the ACE reporter recovered by high-fidelity PCR of mCherry-positive 293T. Mutated nucleotides are highlighted, and deleted nucleotides are indicated by hyphens. The number of times each sequence was recovered ("n") is indicated to the right. Sequence identifiers also are provided.

FIGS. 5A-5C show that ACE enriches for base-editing events at heterologous genomic loci. FIG. 5A is a schematic of a co-transfection experiment resulting in ACE reporter activation (shading represents mCherry and eGFP double-positive cells). The FANCF (Fanconi anemia group F gene) and a PstI restriction assay were used to quantify chromosomal base editing of this locus, as base editing events destroy the PstI cleavage site and block cleavage of the 452 bp amplicon into 260 and 192 bp products. FIG. 5B is representative agarose gels image, showing the results of FANCF base editing by A3A (left) and A3Bctd (right) editosomes in 293T cells. The percentage of base editing was calculated by dividing the percentage of substrate band by the total of substrate and product bands following PstI cleavage for both unsorted and mCherry-positive cell populations. FIG. 5C shows Sanger sequencing results for the gRNA-binding region of the FANCF gene, which was recovered by high-fidelity PCR using genomic DNA from mCherry-positive 293T. Mutated nucleotides are highlighted, and deleted nucleotides are indicated by hyphens. The number of times each sequence was recovered ("n") is indicated to the right. Sequence identifiers also are provided.

FIGS. 6A and 6B provide data for selected mCherry mutant constructs. FIG. 6A shows DNA and amino sequences for the codon 59 region of wild-type mCherry (L59; SEQ ID NO:89), a single amino acid derivative (S59; SEQ ID NO:91), and the ACE reporter (an abbreviated depiction of the full sequence shown in FIG. 1C with the +43 bp insertion; SEQ ID NO:93). FIG. 6B includes representative fluorescence microscopy images showing mCherry activity for the L59 and S59 constructs, and no mCherry activity for the ACE reporter until editing by gRNA59 and a functional editosome (e.g., A3A-Cas9n-UGI; inset white bars=30 µm).

FIG. 7A is a graph plotting quantification of ACE reporter activation in SSM2c, COS7, and CHO cells 48 hours after co-transfection of ACE reporter, mCherry codon 59 targeting gRNA or NS-gRNA, and A3A-Cas9n-UGI, A3Bctd-Cas9n-UGI, or rat APOBEC1-Cas9n-UGI (BE3) constructs (n=3; mean±SD). FIG. 7B shows anti-Cas9 and anti-HSP90 immunoblots from a representative experiment as plotted in FIG. 7A.

FIGS. 9A-9C show AMBER results for single base editing in chromosomal contexts. FIG. 9A is a graph plotting the quantification of editing for a single-copy genomic eGFP codon 138 AMBER reporter in 293T cells (n=3, ±SD). FIG. 9B is a graph plotting the quantification of editing for a single-copy genomic eGFP codon 202 AMBER reporter in 293T cells (n=3, ±SD). FIG. 9C shows Sanger sequencing results of the gRNA binding region for the eGFP codon 202 reporter and the eGFP codon 138 reporter with forty base pairs flanking up- and downstream recovered by high-fidelity PCR of relevant portions of the eGFP reporter from eGFP-positive 293T cells. Mutated nucleotides are boxed and deleted nucleotides are indicated by hyphens. The number of times each sequence was recovered ("n") is shown to the right. Sequence identifiers also are shown.

DETAILED DESCRIPTION

Figure 1A:
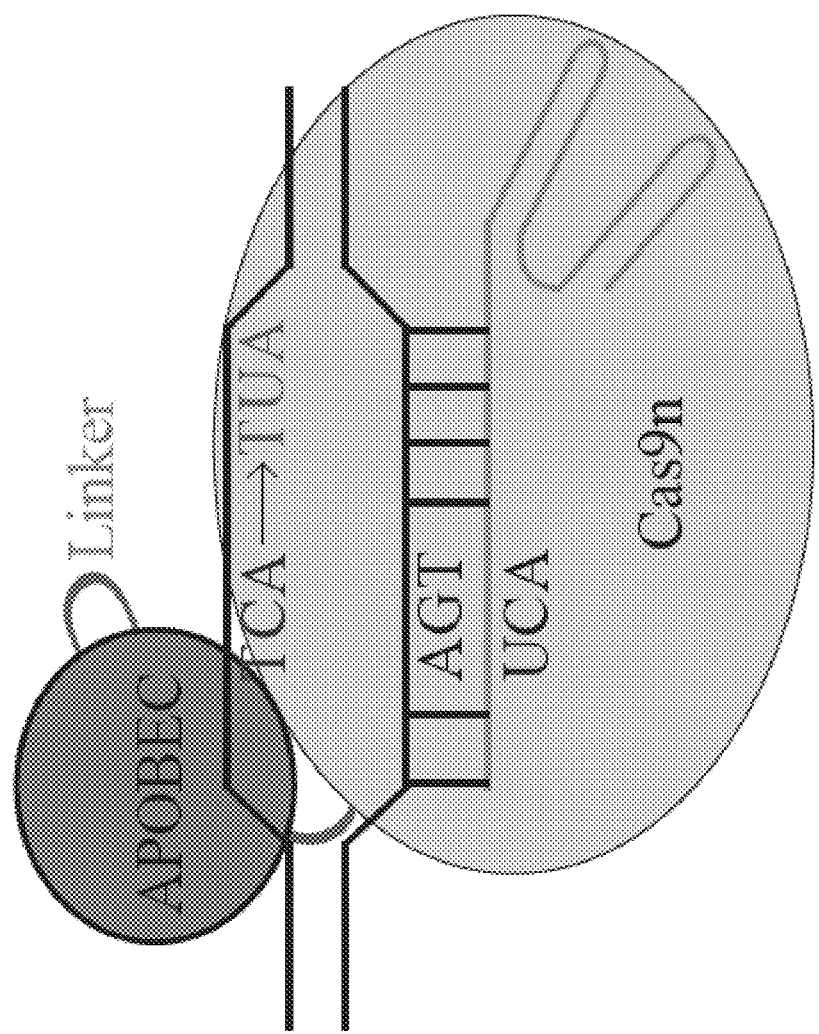
FIGS. 1A-1G illustrate an APOBEC- and Cas9-mediated base editing (ACE) real-time reporter for APOBEC-Cas9 base editing.

APOBEC enzymes are single-stranded (ss) polynucleotide cytosine deaminases. Human cells encode nine active family members, including activation-induced deaminase (AID), which functions in antibody DNA diversification, APOBEC1, which functions in mRNA editing, and APOBEC3A-H (A3A, A3B, A3C, A3D, A3F, A3G, and A3H), which function in virus and transposon DNA restriction (Conticello, *Genome Biol* 9:229, 2008; Harris and Dudley, *Virology* 479-480C:131-145, 2015; and Nabel et al., *ACS Chem Biol* 7:20-30, 2012). APOBEC1 also is an efficient DNA mutator (Harris et al., *Mol Cell* 10:1247-1253, 2002). The rat APOBEC1 enzyme can be combined with Cas9 and a guide RNA (gRNA) to create ribonucleoprotein complexes capable of editing single cytosine nucleobases and making site-specific C-to-T mutations in genomic DNA (Komor et al., *Nature* 533:420-424, 2016) (FIG. 1A). A fusion polypeptide ("BE3") containing rat APOBEC1, Cas9 nickase (Cas9n), and uracil DNA glycosylase inhibitor (UGI) can yield base editing frequencies ranging from 5% to 50%, and can be harnessed for biotechnology applications. See, e.g., Komor et al., supra; Rees et al., *Nat Commun* 8:15790, 2017; Kim et al., *Nat Biotechnol* 35:371-376, 2017; Kim et al., *Nat Biotechnol* 35:475-480, 2017; Kim et al., *Nat Biotechnol* 35:435-437, 2017; Li et al., *Mol Plant* 10:526-529, 2017; Lu and Zhu, *Mol Plant* 10:523-525, 2017; and Zong et al., *Nat Biotechnol* 35:438-440, 2017).

Two orthologs, human AID and lamprey PmCDA1, also have been combined with Cas9n but with lower overall base editing efficiencies that likely resulted from lower intrinsic enzyme activities (Hess et al., *Nat Methods* 13:1036-1042, 2016; Nishida et al., *Science* 353(6305):aaf8729, 2016; Shimatani et al., *Nat Biotechnol* 35:441-443, 2017; and Kuscu and Adli, *Nat Methods* 13:983-984, 2016). PmCDA1 also has been used in plant genome engineering (Shimatani et al., supra).

Figure 1B:
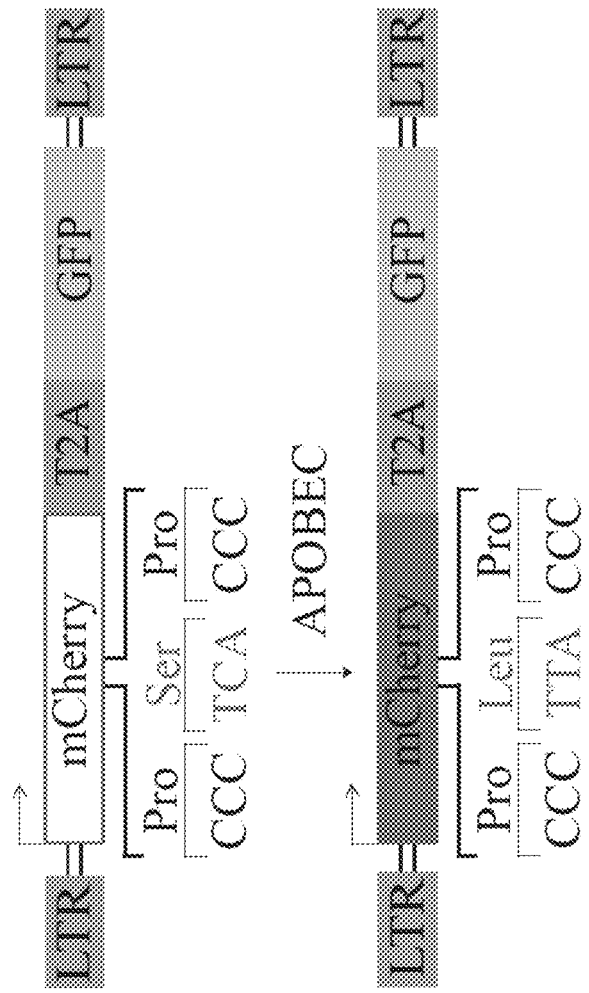
Figure 1C:
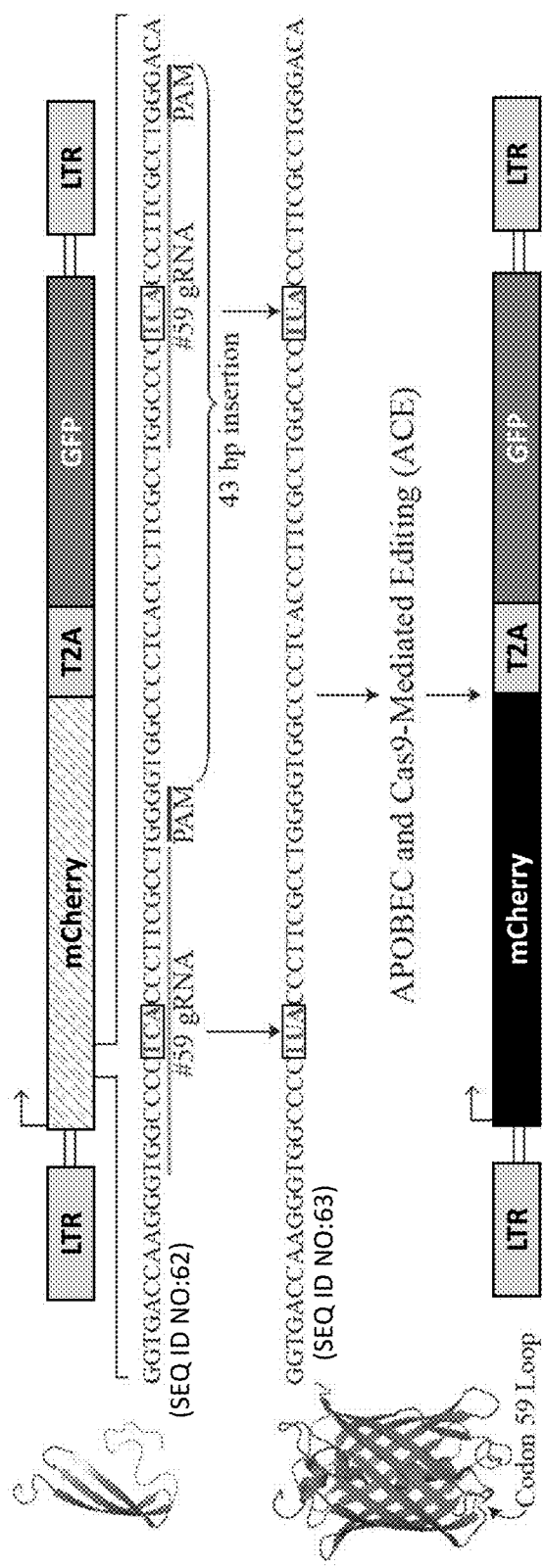

The materials and methods disclosed herein can facilitate optimization of base editing technologies, and promote deployment of the technologies in limitless cell types. The reporter system provides an efficient, rapid, and quantitative editing assay that can be done in real-time, is transferable across species, and is independent of DNA sequencing read-outs. In general, the system includes any two reporter components, where one reporter is always "on" to provide an internal control, and the other reporter is inactive, or has reduced activity, due to the presence of a revertible mutation (e.g., a T-to-C mutation) at a position that is essential for activity. Schematics of such a system, previously referred to as an "APOBEC-mediated base editing reporter" (AMBER) system and referred to herein as an "APOBEC- and Cas9-mediated editing (ACE) reporter, are shown in FIGS. 1B and 1C. The exemplary ACE system depicted in FIGS. 1B and 1C is a dual mCherry/eGFP reporter system that is based on creating an APOBEC editing hotspot, TCA, at a codon essential for mCherry function. A C-to-T (or C-to-U in the case of RNA) editing event at this codon results in reversion of TCA-to-TTA and restoration of fluorescence activity in a tight "off-to-on" gain of function system.

Figure 1D:
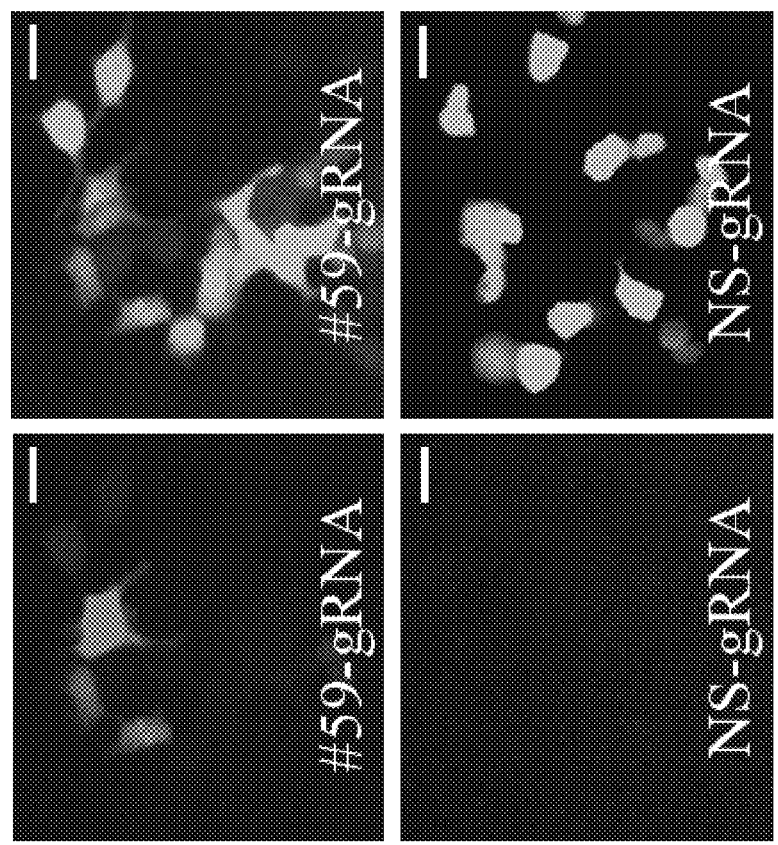
Figure 1E:
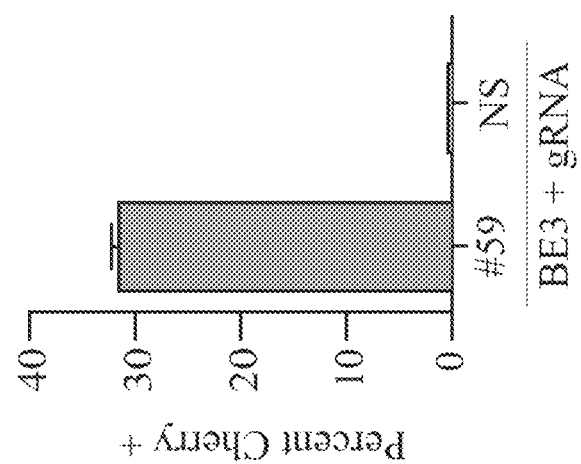
Figure 1F:
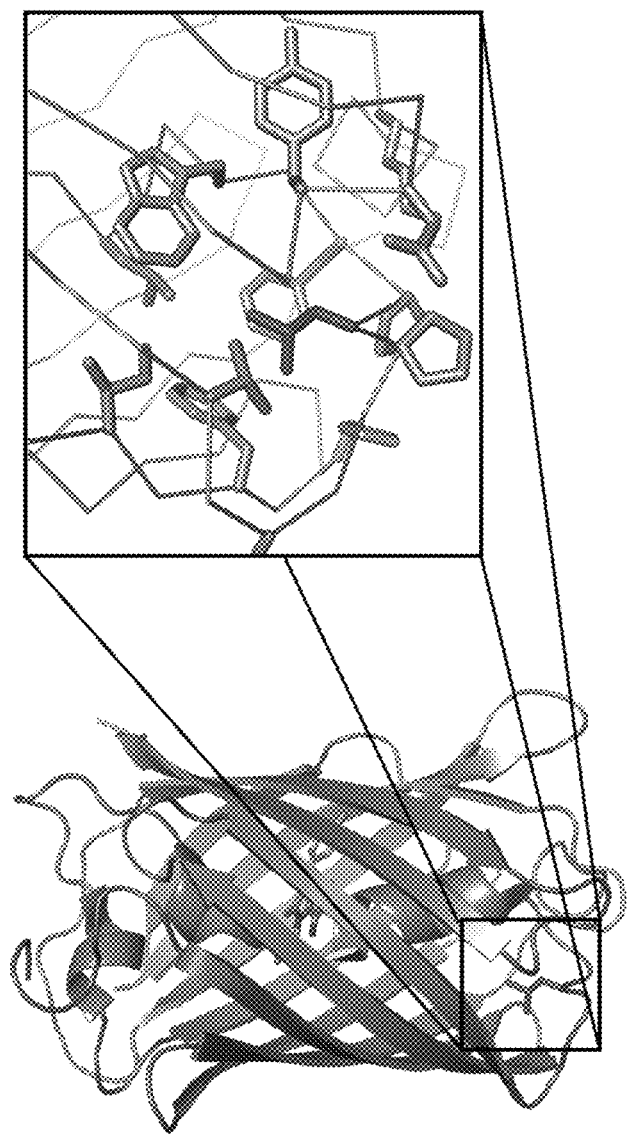
Figure 1G:
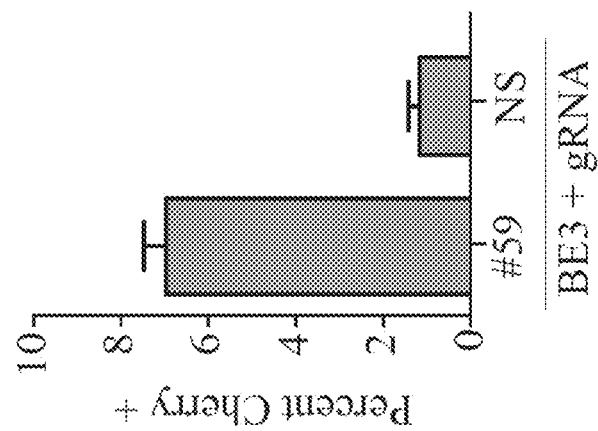
Figure 7A:
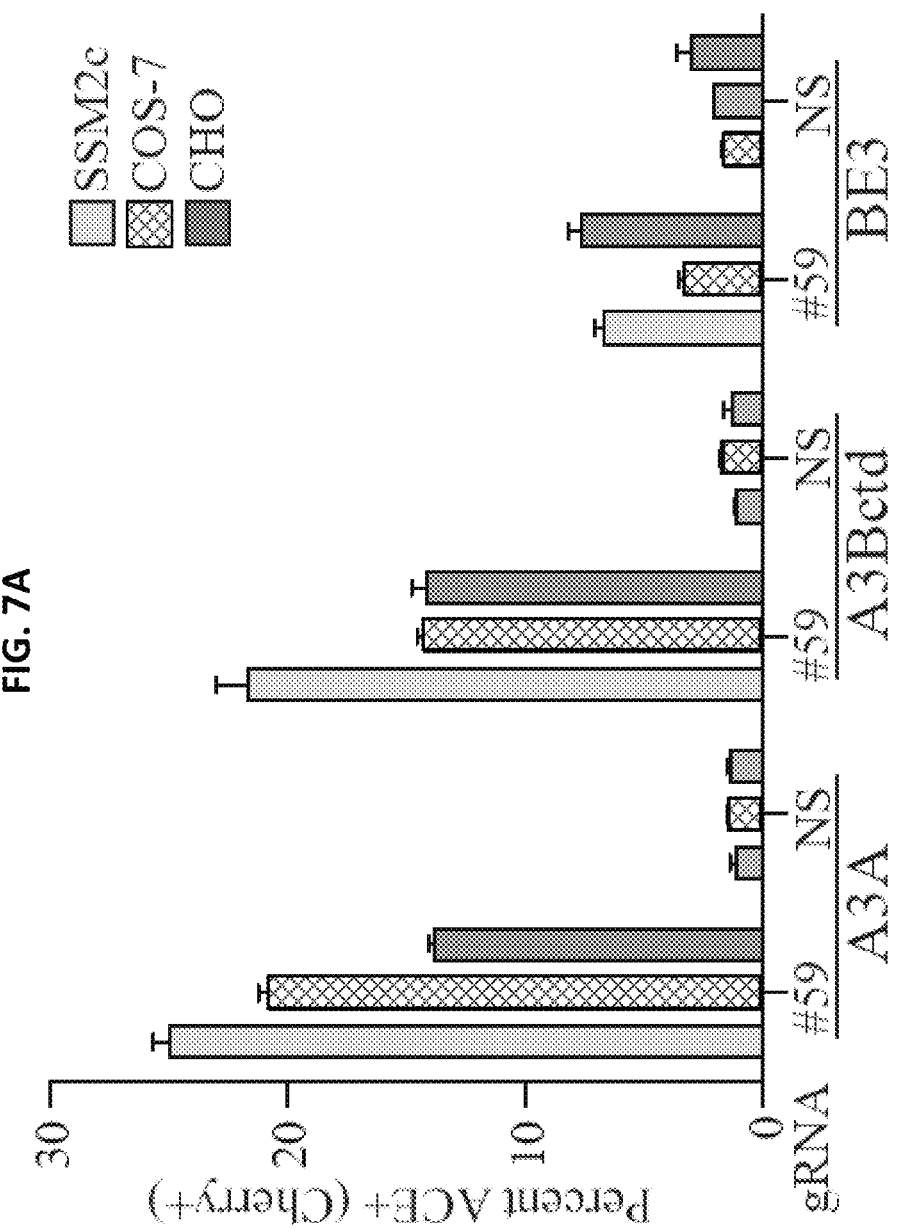
FIGS. 7A and 7B show ACE reporter activity in other cell types.
Figure 7B:
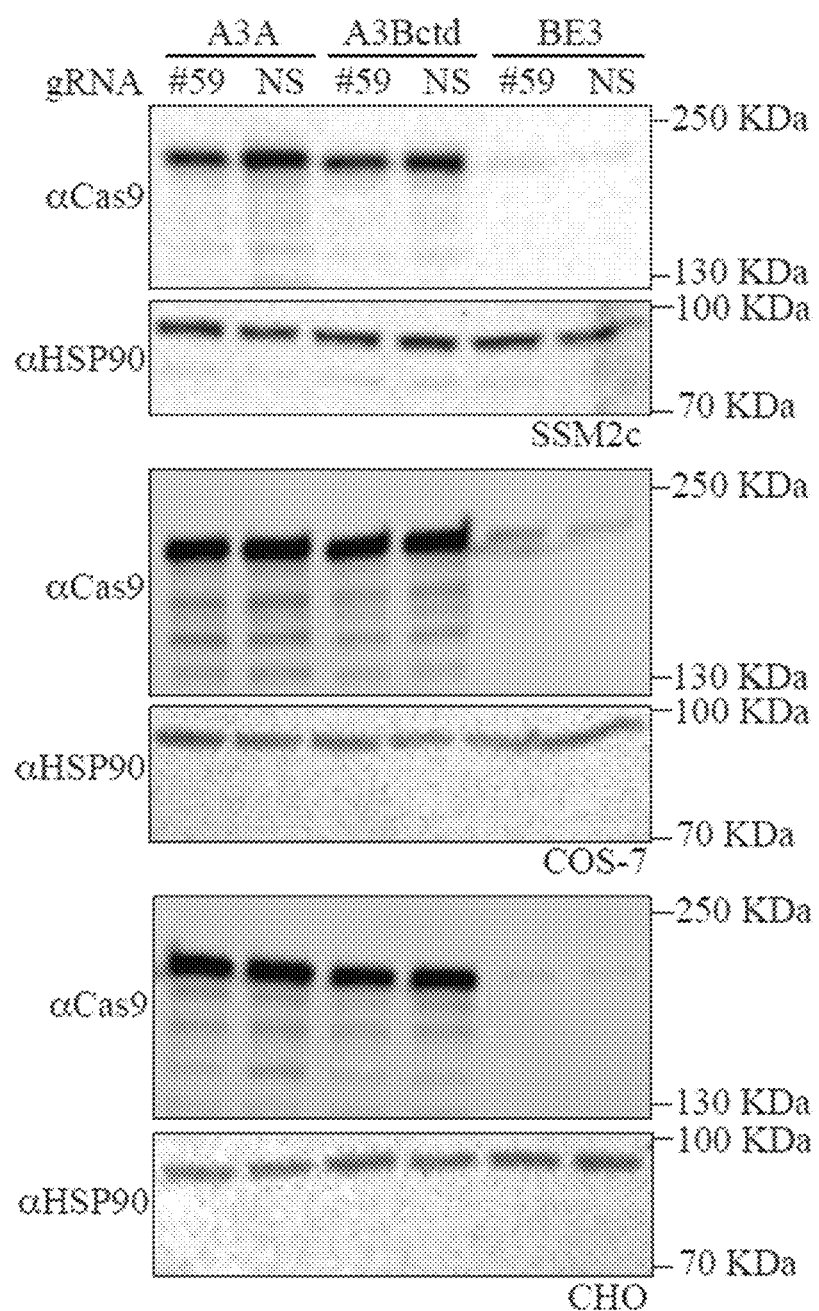
Figure 9A:
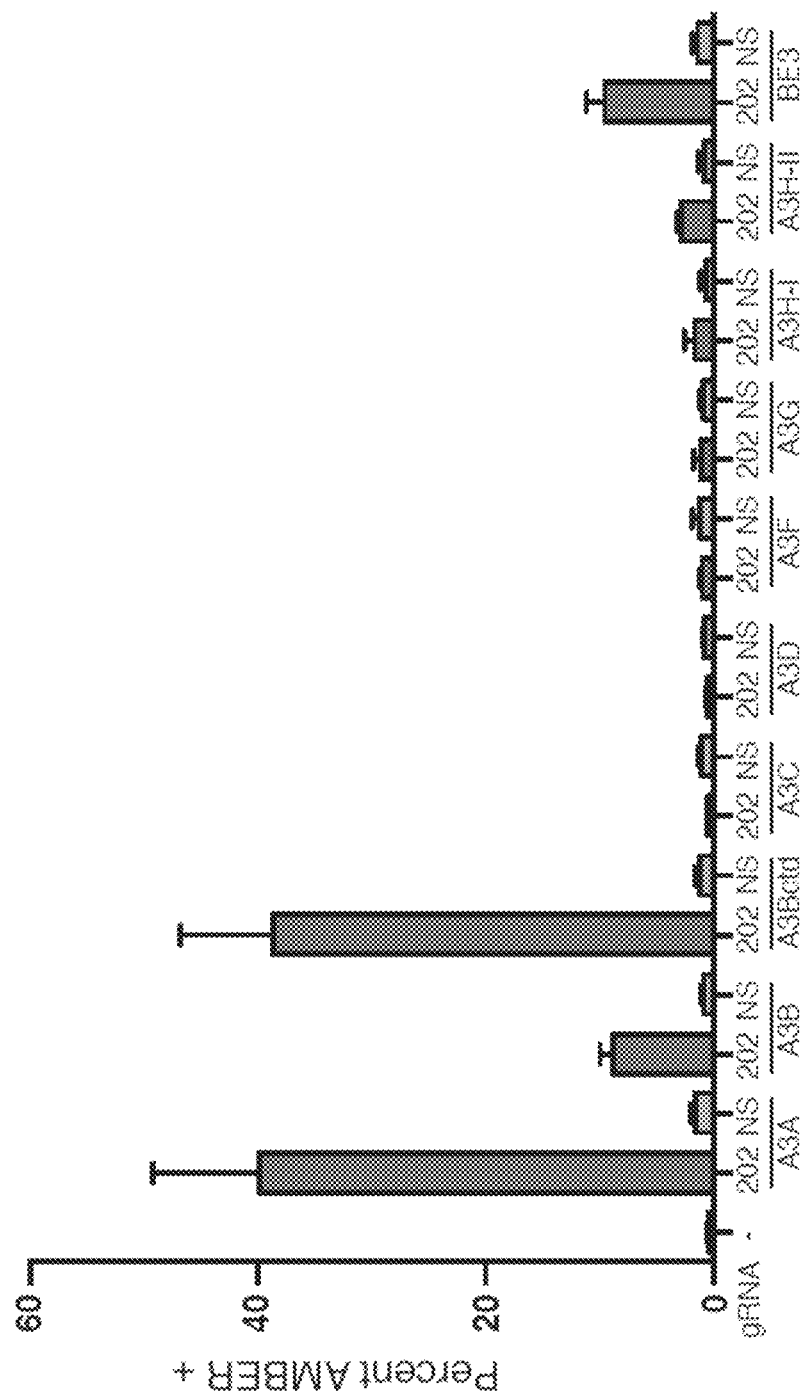
Figure 9B:
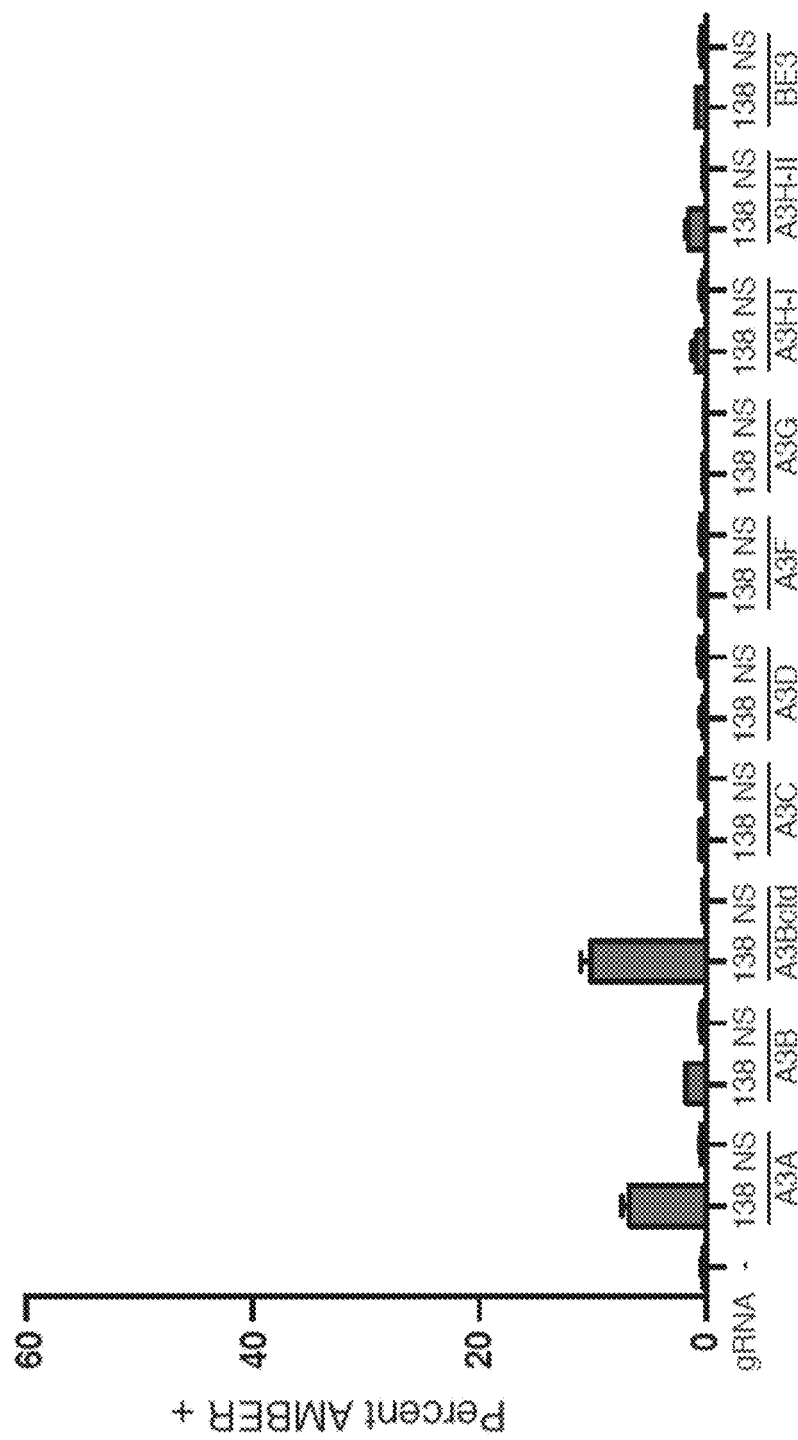
Figure 9C:
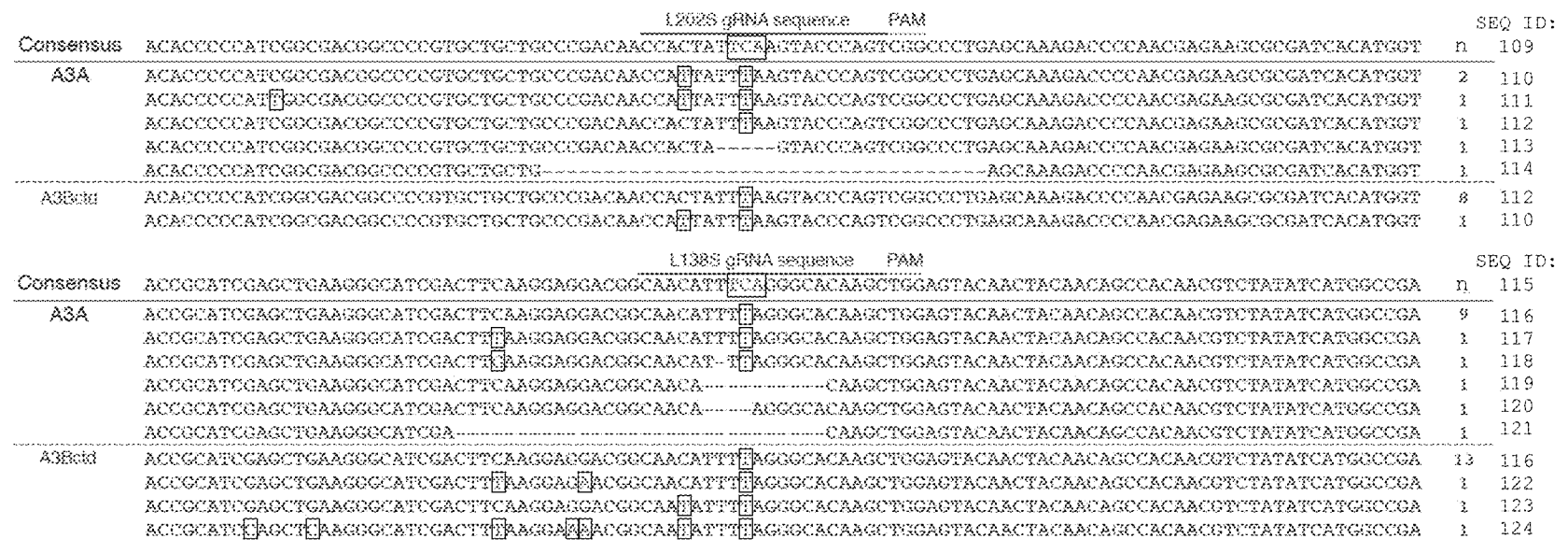

The reporter system provided herein is portable and capable of providing real-time read-outs of editing activity in a variety of different cell lines, including human cell lines (e.g., HeLa cells, as shown in FIG. 1G, SSM2c, COS7, and CHO cells as shown in FIGS. 7A and 7B, and 293T cells as shown in FIGS. 9A-9C). The system can be particularly useful with base editing technologies utilizing editosomes that have high efficiency and defined structural information that can guide rational improvements such as single nucleobase specificity. APOBEC1 and PmCDA1 have not yet yielded structures, and the crystallized form of AID is significantly divergent (Pham et al., *DNA Repair* (Amst) 54:8-12, 2017). Thus, APOBEC3A (A3A) and APOBEC3B (A3B) were initially tested for Cas9n-directed base editing, as described the Examples herein. These enzymes are the most efficient ssDNA C-to-U deaminases in human cells (see, e.g., Stenglein et al., *Nat Struct Mol Biol* 17:222-229, 2010; Carpenter et al., *J Biol Chem* 287:34801-34808, 2012; Burns et al., *Nature* 494:366-370, 2013; and Ito et al., *J Mol Biol*, 429(12):1787-1799, 2017), and high-resolution crystal structures of both apo- and ssDNA-bound forms have been determined (Bohn et al., *Structure* 23:903-911, 2015; Shi et al., *J Biol Chem* 290:28120-28130, 2015; Shi et al., *Nat Struct Mol Biol* 24:131-139, 2017; and Kouno *Nat Commun* 8:15024, 2017). A3A-ssDNA and A3B C-terminal domain (A3Bctd)-ssDNA structures share a unique U-shaped bound ssDNA conformation that provides an atomic explanation for their intrinsic 5'-TC specificity (Shi et al. 2017, supra; and Kouno et al. supra). As testament to the utility of this structural information, it informed a single amino acid change in a loop region adjacent to the active site of A3A that altered its intrinsic specificity from 5'-TC to 5'-CC (Shi et al. 2017, supra). These results strongly suggest that additional enzyme customization will enable tailoring these enzymes to all possible dinucleotide (5'-NC) and trinucleotide (5'-NCN) contexts: 5'-AC, 5'-CC, 5'-GC, 5'-TC, 5'-ACA, 5'-ACC, 5'-ACG, 5'-ACT, 5'-CCA, 5'-CCC, 5'-CCG, 5'-CCT, 5'-GCA, 5'-GCC, 5'-GCG, 5'-GCT, 5'-TCA, 5'-TCC, 5'-TCG, and 5'-TCT.

Thus, this document provides nucleic acids containing sequences that encode the components of the ACE reporter system disclosed herein. This document also provides vectors containing the nucleic acids, cells containing the nucleic acids and/or vectors, and methods for using the ACE reporter system to monitor base editing in cells.

The nucleic acids provided herein can include, for example, a sequence encoding a first reporter that is inactive or has reduced activity, and a sequence encoding a second reporter that is active. In some cases, the first reporter can be a mutant mCherry reporter having a T to C mutation at the second position of the codon encoding amino acid 59 (corresponding to amino acid 56 in the representative sequence set forth in SEQ ID NO:2), which results in a Leu to Ser substitution in the expressed mCherry polypeptide, and the second reporter can be a GFP polypeptide, such as an eGFP polypeptide having the sequence set forth in SEQ ID NO:4).

In some cases, the first reporter can be a mutant eGFP reporter having a mutation at codon 202, codon 138, or codon 93 that ablates fluorescence, where fluorescence can be restored when a C within the mutant codon is changed to T by an editosome as described herein. For example, the codon encoding leucine at position 202 of SEQ ID NO:4 can be changed from CTG to TCA, such that it encodes serine, and editing of the codon to TTA restores the leucine and fluorescence. The codon encoding leucine at position 138 of SEQ ID NO:4 also can be changed from CTG to TCA, such that it encodes serine, and editing of the codon to TTA restores the leucine and fluorescence. The codon encoding tyrosine at position 93 of SEQ ID NO:4 can be changed from TAC to CAC, and editing of the codon back to TAC can restore fluorescence. The second reporter can be, for example, a mCherry polypeptide, such as a mCherry polypeptide having the sequence set forth in SEQ ID NO:2.

The sequences encoding the first and second reporters can be operably linked to a single promoter, and may be separated by a cleavage sequence (e.g., a T2A self-cleaving peptide sequence) to permit separation of the first and second reporters after they are expressed. When an ACE reporter nucleic acid is contacted with an APOBEC-Cas9 base editing complex that can trigger deamination of the mutant cytosine, changing it to a thymine/uracil, fluorescence of the first reporter will be fully restored, and the ratio of first reporter:second reporter (e.g., mCherry:eGFP) fluorescence will increase (and conversely, the ratio of second reporter:first reporter fluorescence will decrease). The restoration of first reporter fluorescence and an increased first reporter:second reporter fluorescence ratio (or reduced second reporter:first reporter ratio) can serve as a real time indicator of APOBEC-Cas9 activity.

The exemplary reporter systems that were generated and tested as described herein utilized mCherry as the first reporter and eGFP as the second reporter, or utilized eGFP as the first reporter and mCherry as the second reporter. A representative mCherry nucleotide sequence is set forth in SEQ ID NO:1 (GENBANK® accession no. KJ541669.2), which encodes a mCherry polypeptide having SEQ ID NO:2 (GENBANK® accession no. AIC82341.1). A representative eGFP nucleotide sequence is set forth in SEQ ID NO:3 (GENBANK® accession no. U55762.1), which encodes a full-length eGFP polypeptide having SEQ ID NO:4 (GENBANK® accession no. AAB02575.1). SEQ ID NOS:1-4 are set forth below.

mCherry (KJ541559.2):
(SEQ ID NO: 1)
AAGGGCGAGGAGGATAACATGGCCATCATCAAGGAGTTCATGCGCTTCAA

GGTGCACATGGAGGGCTCCGTGAACGGCCACGAGTTCGAGATCGAGGGCG

AGGGCGAGGGCCGCCCCTACGAGGGCACCCAGACCGCCAAGCTGAAGGTG

ACCAAGGGTGGCCCCCTGCCCTTCGCCTGGGACATCCTGTCCCCTCAGTT

CATGTACGGCTCCAAGGCCTACGTGAAGCACCCCGCCGACATCCCCGACT

ACTTGAAGCTGTCCTTCCCCGAGGGCTTCAAGTGGGAGCGCGTGATGAAC

TTCGAGGACGGCGGCGTGGTGACCGTGACCCAGGACTCCTCCCTGCAGGA

CGGCGAGTTCATCTACAAGGTGAAGCTGCGCGGCACCAACTTCCCCTCCG

ACGGCCCCGTAATGCAGAAGAAGACTATGGGCTGGGAGGCCTCCTCCGAG

CGGATGTACCCCGAGGACGGCGCCCTGAAGGGCGAGATCAAGCAGAGGCT

GAAGCTGAAGGACGGCGGCCACTACGACGCTGAGGTCAAGACCACCTACA

AGGCCAAGAAGCCCGTGCAGCTGCCCGGCGCCTACAACGTCAACATCAAG

TTGGACATCACCTCCCACAACGAGGACTACACCATCGTGGAACAGTACGA

ACGCGCCGAGGGCCGCCACTCCACCGGCGGCATGGACGAGCTGTACAAG mCherry (AIC82341.1):
(SEQ ID NO: 2)
KGEEDNMAIIKEFMRFKVHMEGSVNGHEFEIEGEGEGRPYEGTQTAKLKV

TKGGPLPFAWDILSPQFMYGSKAYVKHPADIPDYLKLSFPEGFKWERVMN

FEDGGVVTVTQDSSLQDGEFIYKVKLRGTNFPSDGPVMQKKTMGWEASSE

RMYPEDGALKGEIKQRLKLKDGGHYDAEVKTTYKAKKPVQLPGAYNVNIK

LDITSHNEDYTIVEQYERAEGRHSTGGMDELYK eGFP (U55762.1):
(SEQ ID NO: 3)
ATGGTGAGCAAGGGCGAGGAGCTGTTCACCGGGGTGGTGCCCATCCTGGT

CGAGCTGGACGGCGACGTAAACGGCCACAAGTTCAGCGTGTCCGGCGAGG

GCGAGGGCGATGCCACCTACGGCAAGCTGACCCTGAAGTTCATCTGCACC

ACCGGCAAGCTGCCCGTGCCCTGGCCCACCCTCGTGACCACCCTGACCTA

CGGCGTGCAGTGCTTCAGCCGCTACCCCGACCACATGAAGCAGCACGACT

TCTTCAAGTCCGCCATGCCCGAAGGCTACGTCCAGGAGCGCACCATCTTC

TTCAAGGACGACGGCAACTACAAGACCCGCGCCGAGGTGAAGTTCGAGGG

CGACACCCTGGTGAACCGCATCGAGCTGAAGGGCATCGACTTCAAGGAGG

ACGGCAACATCCTGGGGCACAAGCTGGAGTACAACTACAACAGCCACAAC

GTCTATATCATGGCCGACAAGCAGAAGAACGGCATCAAGGTGAACTTCAA

GATCCGCCACAACATCGAGGACGGCAGCGTGCAGCTCGCCGACCACTACC

AGCAGAACACCCCCATCGGCGACGGCCCCGTGCTGCTGCCCGACAACCAC

TACCTGAGCACCCAGTCCGCCCTGAGCAAAGACCCCAACGAGAAGCGCGA

TCACATGGTCCTGCTGGAGTTCGTGACCGCCGCCGGGATCACTCTCGGCA

TGGACGAGCTGTACAAGTAA eGFP (AAB02575.1):
(SEQ ID NO: 4)
MVSKGEELFTGVVPILVELDGDVNGHKFSVSGEGEGDATYGKLTLKFICT

TGKLPVPWPTLVTTLTYGVQCFSRYPDHMKQHDFFKSAMPEGYVQERTIF

FKDDGNYKTRAEVKFEGDTLVNRIELKGIDFKEDGNILGHKLEYNYNSHN

VYIMADKQKNGIKVNFKIRHNIEDGSVQLADHYQQNTPIGDGPVLLPDNH

YLSTQSALSKDPNEKRDHMVLLEFVTAAGITLGMDELYK

It is to be noted that other reporters also can be used in the systems and methods provided herein. These include, without limitation, Cyan Fluorescent Protein (e.g., AmCyan1), other GFPs (e.g., AcGFP1 and ZsGreen1), Yellow Fluorescent Proteins (e.g., ZsYellow1 and mBanana), Orange Fluorescent Proteins (e.g., mOrange and mOrange2), other Red Fluorescent Proteins (e.g., DsRed-Express2, DsRed-Express, tdTomato, DsRed-Monomer, DsRed2, AsRed2, and mStrawberry), Far-red fluorescent Proteins (e.g., HcRedl, mRaspberry, E2-Crimson, and mPlum), and Switchable Fluorescent Proteins (e.g., Dendra2, Timer, and PAm-Cherry). All of the aforementioned are available from, for example, Takara Bio USA, Inc. (formerly Clontech Laboratories, Inc.; Mountain View, Calif.). Any of these or other fluorescent reporters can be used in the materials and methods described herein, as they all have sites that can be adapted to report APOBEC base editing. For example, in the CFP sequence (taken, for example, from Addgene Plasmid #13030), amino acids L16, L54, L138, Y93, Y152 all meet the criteria of having a PAM that exists or that can be mutated within an appropriate distance (typically about 5 to 20 bp, such as 7 to 18 bp, or 9 to 16 bp) from the target cytosine. Further, in the mOrange sequence (from Addgene Plasmid #29748), L50, L59, L90, L170, L172, Y72, and Y186 all meet the criteria of having a PAM that exists or that can be mutated in at an appropriate distance from the target cytosine.

The terms "nucleic acid" and "polynucleotide" are used interchangeably, and refer to both RNA and DNA, including cDNA, genomic DNA, synthetic (e.g., chemically synthesized) DNA, and DNA (or RNA) containing nucleic acid analogs. Polynucleotides can have any three-dimensional structure. A nucleic acid can be double-stranded or single-stranded (i.e., a sense strand or an antisense single strand). Non-limiting examples of polynucleotides include genes, gene fragments, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers, as well as nucleic acid analogs.

As used herein, "isolated," when in reference to a nucleic acid, refers to a nucleic acid that is separated from other nucleic acids that are present in a genome, e.g., a plant genome, including nucleic acids that normally flank one or both sides of the nucleic acid in the genome. The term "isolated" as used herein with respect to nucleic acids also includes any non-naturally-occurring sequence, since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences, as well as DNA that is incorporated into a vector, an autonomously replicating plasmid, a virus (e.g., a pararetrovirus, a retrovirus, lentivirus, adenovirus, or herpes virus), or the genomic DNA of a prokaryote or eukaryote. In addition, an isolated nucleic acid can include a recombinant nucleic acid such as a DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

A nucleic acid can be made by, for example, chemical synthesis or polymerase chain reaction (PCR). PCR refers to a procedure or technique in which target nucleic acids are amplified. PCR can be used to amplify specific sequences from DNA as well as RNA, including sequences from total genomic DNA or total cellular RNA. Various PCR methods are described, for example, in *PCR Primer: A Laboratory Manual*, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid.

Isolated nucleic acids also can be obtained by mutagenesis. For example, a donor nucleic acid sequence can be mutated using standard techniques, including oligonucleotide-directed mutagenesis and site-directed mutagenesis through PCR. See, *Short Protocols in Molecular Biology*, Chapter 8, Green Publishing Associates and John Wiley & Sons, edited by Ausubel et al., 1992.

Recombinant nucleic acid constructs (e.g., vectors) also are provided herein. A "vector" is a replicon, such as a plasmid, phage, or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs, or PACs. The term "vector" includes cloning and expression vectors, as well as viral vectors and integrating vectors. An "expression vector" is a vector that includes one or more expression control sequences, and an "expression control sequence" is a DNA sequence that controls and regulates the transcription and/or translation of another DNA sequence. Suitable expression vectors include, without limitation, plasmids and viral vectors derived from, for example, bacteriophage, baculoviruses, tobacco mosaic virus, herpes viruses, cytomegalovirus, retroviruses, vaccinia viruses, adenoviruses, and adeno-associated viruses. Numerous vectors and expression systems are commercially available from such corporations as Novagen (Madison, Wis.), Clontech (Palo Alto, Calif.), Stratagene (La Jolla, Calif.), and Invitrogen/Life Technologies (Carlsbad, Calif.).

The terms "regulatory region," "control element," and "expression control sequence" refer to nucleotide sequences that influence transcription or translation initiation and rate, and stability and/or mobility of the transcript or polypeptide product. Regulatory regions include, without limitation, promoter sequences, enhancer sequences, response elements, protein recognition sites, inducible elements, promoter control elements, protein binding sequences, 5' and 3' untranslated regions (UTRs), transcriptional start sites, termination sequences, polyadenylation sequences, introns, and other regulatory regions that can reside within coding sequences, such as secretory signals, nuclear localization sequences (NLS), and protease cleavage sites.

As used herein, "operably linked" means incorporated into a genetic construct so that expression control sequences effectively control expression of a coding sequence of interest. A coding sequence is "operably linked" and "under the control" of expression control sequences in a cell when RNA polymerase is able to transcribe the coding sequence into RNA, which if an mRNA, then can be translated into the protein encoded by the coding sequence. Thus, a regulatory region can modulate, e.g., regulate, facilitate or drive, transcription in the plant cell, plant, or plant tissue in which it is desired to express a modified target nucleic acid.

A promoter is an expression control sequence composed of a region of a DNA molecule, typically within 1000 nucleotides upstream of the point at which transcription starts (generally near the initiation site for RNA polymerase II). Promoters are involved in recognition and binding of RNA polymerase and other proteins to initiate and modulate transcription. To bring a coding sequence under the control of a promoter, it typically is necessary to position the translation initiation site of the translational reading frame of the polypeptide between one and about fifty nucleotides downstream of the promoter. A promoter can, however, be positioned as much as about 5,000 nucleotides upstream of the translation start site, or about 2,000 nucleotides upstream of the transcription start site. A promoter typically contains at least a core (basal) promoter. A promoter also may include at least one control element such as an upstream element. Such elements include upstream activation regions (UARs) and, optionally, other DNA sequences that affect transcription of a polynucleotide such as a synthetic upstream element.

The percent sequence identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (B12seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the B12seq program can be found in the readme file accompanying BLASTZ. B12seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -1; -r is set to 2; and all other options are left at their default setting. For example, the following command can be used to generate an output file containing a comparison between two sequences: C:\B12seq c:\seq1.txt -j c:\seq2.txt -p blastn -o c:\output.txt -q -1 -r 2. To compare two amino acid sequences, the options of B12seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\B12seq c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence (e.g., SEQ ID NO:2), or by an articulated length (e.g., 100 consecutive nucleotides or amino acid residues from a sequence set forth in an identified sequence), followed by multiplying the resulting value by 100. For example, an amino acid sequence that has 220 matches when aligned with the sequence set forth in SEQ ID NO:2 is 94.4 percent identical to the sequence set forth in SEQ ID NO:2 (i.e., 220/233×100=94.4%). It is noted that the percent sequence identity value is rounded to the nearest tenth. For example, 75.11, 75.12, 75.13, and 75.14 is rounded down to 75.1, while 75.15, 75.16, 7.17, 75.18, and 7.19 is rounded up to 7.2. It also is noted that the length value will always be an integer.

The reporter system disclosed herein can be used with isolated fusion polypeptides containing an APOBEC portion and a DNA-targeting (e.g., Cas9) portion. The term "polypeptide" as used herein refers to a compound of two or more subunit amino acids regardless of post-translational modification (e.g., phosphorylation or glycosylation). The subunits may be linked by peptide bonds or other bonds such as, for example, ester or ether bonds. The term "amino acid" refers to either natural and/or unnatural or synthetic amino acids, including D/L optical isomers.

By "isolated" or "purified" with respect to a polypeptide it is meant that the polypeptide is separated to some extent from the cellular components with which it is normally found in nature (e.g., other polypeptides, lipids, carbohydrates, and nucleic acids). A purified polypeptide can yield a single major band on a non-reducing polyacrylamide gel. A purified polypeptide can be at least about 75% pure (e.g., at least 80%, 85%, 90%, 95%, 97%, 98%, 99%, or 100% pure). Purified polypeptides can be obtained by, for example, extraction from a natural source, by chemical synthesis, or by recombinant production in a host cell or transgenic plant, and can be purified using, for example, affinity chromatography, immunoprecipitation, size exclusion chromatography, and ion exchange chromatography. The extent of purification can be measured using any appropriate method, including, without limitation, column chromatography, polyacrylamide gel electrophoresis, or high-performance liquid chromatography.

A representative A3A sequence is set forth in SEQ ID NO:5 (NCBI reference sequence NM_145699), which encodes a full-length human A3A polypeptide having SEQ ID NO:6 (NCBI reference sequence NP_663745.1). A representative A3B sequence is set forth in SEQ ID NO:7 (NCBI reference sequence NM_004900), which encodes a full-length human A3B polypeptide having SEQ ID NO:8 (NCBI reference sequence NP_004891.4). SEQ ID NOS:5-8 are set forth below. Other human and non-human APOBEC sequences are set forth elsewhere (e.g., human APOBEC1, AID, APOBEC3C, APOBEC3D, APOBEC3F, APOBEC3G, and APOBEC3H; GENBANK® accession nos. NM_001644, NM_020661, NM_014508, NM_152426, NM_145298, NM_021822, and NM_181773, respectively), and may be used with the reporter system and the methods provided herein. Of note, A3H may be useful, as described in Example 7 herein. Haplotypes II and V of A3H have 182, 183, and 200 residue splice forms, and all have similar activity.

Human APOBEC3A (NM_145699):
(SEQ ID NO: 5)
GGAGAAGGGGTGGGGCAGGGTATCGCTGACTCAGCAGCTTCCAGGTTGCT

CTGATGATATATTAAGGCTCCTGAATCCTAAGAGAATGTTGGTGAAGATC

TTAACACCACGCCTTGAGCAAGTCGCAAGAGCGGGAGGACACAGACCAGG

AACCGAGAAGGGACAAGCACATGGAAGCCAGCCCAGCATCCGGGCCCAGA

CACTTGATGGATCCACACATATTCACTTCCAACTTTAACAATGGCATTGG

AAGGCATAAGACCTACCTGTGCTACGAAGTGGAGCGCCTGGACAATGGCA

CCTCGGTCAAGATGGACCAGCACAGGGGCTTTCTACACAACCAGGCTAAG

AATCTTCTCTGTGGCTTTTACGGCCGCCATGCGGAGCTGCGCTTCTTGGA

CCTGGTTCCTTCTTTGCAGTTGGACCCGGCCCAGATCTACAGGGTCACTT

GGTTCATCTCCTGGAGCCCCTGCTTCTCCTGGGGCTGTGCCGGGGAAGTG

CGTGCGTTCCTTCAGGAGAACACACACGTGAGACTGCGTATCTTCGCTGC

CCGCATCTATGATTACGACCCCCTATATAAGGAGGCACTGCAAATGCTGC

GGGATGCTGGGGCCCAAGTCTCCATCATGACCTACGATGAATTTAAGCAC

TGCTGGGACACCTTTGTGGACCACCAGGGATGTCCCTTCCAGCCCTGGGA

TGGACTAGATGAGCACAGCCAAGCCCTGAGTGGGAGGCTGCGGGCCATTC

TCCAGAATCAGGGAAACTGAAGGATGGGCCTCAGTCTCTAAGGAAGGCAG

AGACCTGGGTTGAGCAGCAGAATAAAAGATCTTCTTCCAAGAAATGCAAA

CAGACCGTTCACCACCATCTCCAGCTGCTCACAGACGCCAGCAAAGCAGT

ATGCTCCCGATCAAGTAGATTTTTAAAAAATCAGAGTGGGCCGGGCGCGG

TGGCTCACGCCTGTAATCCCAGCACTTTGGAGGCCAAGGCGGGTGGATCA

CGAGGTCAGGAGATCGAGACCATCCTGGCTAACACGGTGAAACCCTGTCT

CTACTAAAAATACAAAAAATTAGCCAGGCGTGGTGGCGGGCGCCTGTAGT

CCCAGCTACTCTGGAGGCTGAGGCAGGAGAGTAGCGTGAACCCGGGAGGC

AGAGCTTGCGGTGAGCCGAGATTGCGCTACTGCACTCCAGCCTGGGCGAC

AGTACCAGACTCCATCTCAAAAAAAAAAAAACCAGACTGAATTAATTTTA

ACTGAAAATTTCTCTTATGTTCCAAGTACACAATAGTAAGATTATGCTCA

ATATTCTCAGAATAATTTTCAATGTATTAATGAAATGAAATGATAATTTG

GCTTCATATCTAGACTAACACAAAATTAAGAATCTTCCATAATTGCTTTT

GCTCAGTAACTGTGTCATGAATTGCAAGAGTTTCCACAAACACT

Human APOBEC3A (NP_663745.1):
(SEQ ID NO: 6)
MEASPASGPRHLMDPHIFTSNFNNGIGRHKTYLCYEVERLDNGTSVKMDQ

HRGFLHNQAKNLLCGFYGRHAELRFLDLVPSLQLDPAQIYRVTWFISWSP

CFSWGCAGEVRAFLQENTHVRLRIFAARIYDYDPLYKEALQMLRDAGAQV

SIMTYDEFKHCWDTFVDHQGCPFQPWDGLDEHSQALSGRLRAILQNQGN

Human APOBEC3B (NM_004900):

(SEQ ID NO: 7)
CACAGAGCTTCAAAAAAGAGCGGGACAGGGACAAGCGTATCTAAGAGGC

TGAACATGAATCCACAGATCAGAAATCCGATGGAGCGGATGTATCGAGAC

ACATTCTACGACAACTTTGAAAACGAACCCATCCTCTATGGTCGGAGCTA

CACTTGGCTGTGCTATGAAGTGAAAATAAAGAGGGGCCGCTCAAATCTCC

TTTGGGACACAGGGGTCTTTCGAGGCCAGGTGTATTTCAAGCCTCAGTAC

CACGCAGAAATGTGCTTCCTCTCTTGGTTCTGTGGCAACCAGCTGCCTGC

TTACAAGTGTTTCCAGATCACCTGGTTTGTATCCTGGACCCCCTGCCCGG

ACTGTGTGGCGAAGCTGGCCGAATTCCTGTCTGAGCACCCCAATGTCACC

CTGACCATCTCTGCCGCCCGCCTCTACTACTACTGGGAAAGAGATTACCG

AAGGGCGCTCTGCAGGCTGAGTCAGGCAGGAGCCCGCGTGAAGATCATGG

ACTATGAAGAATTTGCATACTGCTGGGAAAACTTTGTGTACAATGAAGGT

CAGCAATTCATGCCTTGGTACAAATTCGATGAAAATTATGCATTCCTGCA

CCGCACGCTAAAGGAGATTCTCAGATACCTGATGGATCCAGACACATTCA

CTTTCAACTTTAATAATGACCCTTTGGTCCTTCGACGGCGCCAGACCTAC

TTGTGCTATGAGGTGGAGCGCCTGGACAATGGCACCTGGGTCCTGATGGA

CCAGCACATGGGCTTTCTATGCAACGAGGCTAAGAATCTTCTCTGTGGCT

TTTACGGCCGCCATGCGGAGCTGCGCTTCTTGGACCTGGTTCCTTCTTTG

CAGTTGGACCCGGCCCAGATCTACAGGGTCACTTGGTTCATCTCCTGGAG

CCCCTGCTTCTCCTGGGGCTGTGCCGGGGAAGTGCGTGCGTTCCTTCAGG

AGAACACACGTGAGACTGCGCATCTTCGCTGCCCGCCATCTATGATTAC

GACCCCCTATATAAGGAGGCGCTGCAAATGCTGCGGGATGCTGGGGCCCA

AGTCTCCATCATGACCTACGATGAGTTTGAGTACTGCTGGGACACCTTTG

TGTACCGCCAGGGATGTCCCTTCCAGCCCTGGGATGGACTAGAGGAGCAC

AGCCAAGCCCTGAGTGGGAGGCTGCGGGCCATTCTCCAGAATCAGGGAAA

CTGAAGGATGGGCCTCAGTCTCTAAGGAAGGCAGAGACCTGGGTTGAGCA

GCAGAATAAAGATCTTCTTCCAAGAAATGCAAACAGACCGTTCACCACC

ATCTCCAGCTGCTCACAGACACCAGCAAAGCAATGTGCTCCTGATCAAGT

AGATTTTTTAAAAATCAGAGTCAATTAATTTTAATTGAAAATTTCTCTTA

TGTTCCAAGTGTACAAGAGTAAGATTATGCTCAATATTCCCAGAATAGTT

TTCAATGTATTAATGAAGTGATTAATTGGCTCCATATTTAGACTAATAAA

ACATTAAGAATCTTCCATAATTGTTTCCACAAACACTAAAAAAAAAAAA

AAAAAAAAAA

Human APOBEC3B (NP_004891.4):

(SEQ ID NO: 8)
MNPQIRNPMERMYRDTFYDNFENEPILYGRSYTWLCYEVKIKRGRSNLLW

DTGVFRGQVYFKPQYHAEMCFLSWFCGNQLPAYKCFQITWFVSWTPCPDC

VAKLAEFLSEHPNVTLTISAARLYYYWERDYRRALCRLSQAGARVKIMDY

EEFAYCWENFVYNEGQQFMPWYKFDENYAFLHRTLKEILRYLMDPDTFTF

NFNNDPLVLRRRQTYLCYEVERLDNGTWVLMDQHMGFLCNEAKNLLCGFY

GRHAELRFLDLVPSLQLDPAQIYRVTWFISWSPCFSWGCAGEVRAFLQEN

THVRLRIFAARIYDYDPLYKEALQMLRDAGAQVSIMTYDEFEYCWDTFVY

RQGCPFQPWDGLEEHSQALSGRLRAILQNQGN

An APOBEC-Cas9 fusion polypeptide can include the full-length amino acid sequence of an APOBEC protein, or a catalytic fragment of an APOBEC protein (e.g., a fragment that includes the C-terminal catalytic domain). The APOBEC portion of an APOBEC-Cas9 fusion also may contain a variant APOBEC polypeptide having an amino acid sequence that is at least about 90% identical to a reference APOBEC sequence or a fragment thereof (e.g., at least about 91%, 92%, 93%, 94%, 95%, 96%, 97%, 98%, 99%, 99.5%, or 99.8% identical to SEQ ID NO:6 or SEQ ID NO:8, or a fragment thereof). In some embodiments, for example, an APOBEC-Cas9 fusion polypeptide can include an APOBEC portion that consists essentially of amino acids 13 to 199 of SEQ ID NO:6, amino acids 1 to 195 of SEQ ID NO:6, amino acids 13 to 195 of SEQ ID NO:6, or a sequence that is at least about 90% identical to such a fragment of SEQ ID NO:6. In some embodiments, the APOBEC portion can lack at least amino acids 1-12 of SEQ ID NO:6, at least amino acids 196-199 of SEQ ID NO:6, or at least amino acids 1-12 and 196-199 of SEQ ID NO:6. In some embodiments, the APOBEC portion of an APOBEC-Cas9 fusion polypeptide can consist essentially of amino acids 193 to 382 of SEQ ID NO:8, amino acids 193 to 378 of SEQ ID NO:8, or a sequence that is at least about 90% identical to such a fragment of SEQ ID NO:8. In some embodiments, the APOBEC portion can lack at least amino acids 1-192 of SEQ ID NO:8, or at least amino acids 1-192 and 379-382 of SEQ ID NO:8.

The CRISPR/Cas system includes components of a prokaryotic adaptive immune system that is functionally analogous to eukaryotic RNA interference, using RNA base pairing to direct DNA or RNA cleavage. The Cas9 protein functions as an endonuclease, and CRISPR RNA (crRNA) and tracer RNA (tracrRNA) sequences complex with the Cas9 enzyme and direct it to a target DNA sequence (Makarova et al., *Nat Rev Microbial* 9(6):467-477, 2011). The modification of a single targeting RNA can be sufficient to alter the nucleotide target of a Cas protein. In some cases, crRNA and tracrRNA can be engineered as a single cr/tracrRNA hybrid (also referred to as a "guide RNA" or "gRNA") to direct Cas9 cleavage activity (Jinek et al., *Science,* 337(6096):816-821, 2012). The CRISPR/Cas system can be used in a variety of prokaryotic and eukaryotic organisms (see, e.g., Jiang et al., *Nat Biotechnol,* 31(3):233-239, 2013; Dicarlo et al., *Nucleic Acids Res,* doi:10.1093/nar/gkt135, 2013; Cong et al., *Science,* 339(6121):819-823, 2013; Mali et al., *Science,* 339(6121):823-826, 2013; Cho et al., *Nat Biotechnol,* 31(3):230-232, 2013; and Hwang et al., *Nat Biotechnol,* 31(3):227-229, 2013).

CRISPR clusters are transcribed and processed into crRNA; the correct processing into crRNA requires a trans-encoded small tracrRNA. The combination of Cas9, crRNA, and tracrRNA can then cleave linear or circular dsDNA targets that are complementary to a spacer within the CRISPR cluster. Cas9 recognizes a short protospacer adjacent motif (PAM) in the CRISPR repeat sequences, which aids in distinguishing self from non-self. Cas9 nuclease sequences and structures are well known to those of skill in the art (see, e.g., Ferretti et al., *Proc Natl Acad Sci USA* 98:4658-4663, 2001; Deltcheva et al., *Nature* 471:602-607, 2011; and Jinek Science 337:816-821, 2012). Cas9 orthologs also have been described in species such as S. pyogenes and S. thermophilus.

The homology region within the crRNA sequence (the sequence that targets the crRNA to the desired DNA sequence) can be between about 10 and about 40 (e.g., 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40) nucleotides in length. The tracrRNA hybridizing region within each crRNA sequence can be between about 8 and about 20 (e.g., 8, 9, 10, 11, 12, 13, 14, 15, 16, 17, 18, 19, or 20) nucleotides in length. The overall length of a crRNA sequence can be, for example, between about 20 and about 80 (e.g., 20, 25, 30, 35, 40, 45, 50, 55, 60, 65, 70, 75, or 80) nucleotides, while the overall length of a tracrRNA can be, for example, between about 10 and about 30 (e.g., 10, 12, 14, 16, 18, 20, 22, 24, 26, 28, or 30) nucleotides. The overall length of a gRNA sequence, which includes a homology region and a stem loop region that contains a crRNA/tracrRNA hybridizing region and a linker-loop sequence, can be between about 30 and about 110 (e.g., 30, 35, 40, 45, 50, 55, 60, 65, 70, 75, 80, 85, 90, 95, 100, 105, 110, 115, 120, 125, or 130) nucleotides.

In some embodiments, the Cas9 portion of an APOBEC-Cas9 fusion polypeptide can include the non-catalytic portion of a wild type Cas9 polypeptide, or a Cas9 polypeptide containing one or more mutations (e.g., substitutions, deletions, or additions) within its amino acid sequence as compared to the amino acid sequence of a corresponding wild type Cas9 protein, where the mutant Cas9 does not have nuclease activity. In some embodiments, additional amino acids may be added to the N- and/or C-terminus. For example, Cas9 protein can be modified by the addition of a VP64 activation domain or a green fluorescent protein to the C-terminus, or by the addition of nuclear-localization signals to both the N- and C-termini (see, e.g., Mali et al. Nature Biotechnol 31:833-838, 2013; and Cong et al. Science 339:819-823). A representative Cas9 nucleic acid sequence is set forth in SEQ ID NO:9, and a representative Cas9 amino acid sequence is set forth in SEQ ID NO:10.

```
Streptococcus pyogenes Cas9 (NCBI Ref.
NC_017053.1):
                                        (SEQ ID NO: 9)
ATGGATAAGAAATACTCAATAGGCTTAGATATCGGCACAAATAGCGTCGG

ATGGGCGGTGATCACTGATGATTATAAGGTTCCGTCTAAAAAGTTCAAGG

TTCTGGGAAATACAGACCGCCACAGTATCAAAAAAAATCTTATAGGGCT

CTTTTATTTGGCAGTGGAGAGACAGCGGAAGCGACTCGTCTCAAACGGAC

AGCTCGTAGAAGGTATACACGTCGGAAGAATCGTATTTGTTATCTACAGG

AGATTTTTTCAAATGAGATGGCGAAAGTAGATGATAGTTTCTTTCATCGA

CTTGAAGAGTCTTTTTTGGTGGAAGAAGACAAGAAGCATGAACGTCATCC

TATTTTTGGAAATATAGTAGATGAAGTTGCTTATCATGAGAAATATCCAA

CTATCTATCATCTGCGAAAAAAATTGGCAGATTCTACTGATAAAGCGGAT

TTGCGCTTAATCTATTTGGCCTTAGCGCATATGATTAAGTTTCGTGGTCA

TTTTTTGATTGAGGGAGATTTAAATCCTGATAATAGTGATGTGGACAAAC

TATTTATCCAGTTGGTACAAATCTACAATCAATTATTTGAAGAAACCCT

ATTAACGCAAGTAGAGTAGATGCTAAAGCGATTCTTTCTGCACGATTGAG

TAAATCAAGACGATTAGAAAATCTCATTGCTCAGCTCCCCGGTGAGAAGA

GAAATGGCTTGTTTGGGAATCTCATTGCTTTGTCATTGGGATTGACCCCT

AATTTTAAATCAAATTTTGATTTGGCAGAAGATGCTAAATTACAGCTTTC

AAAAGATACTTACGATGATGATTTAGATAATTTATTGGCGCAAATTGGAG

ATCAATATGCTGATTTGTTTTTGGCAGCTAAGAATTTATCAGATGCTATT

TTACTTTCAGATATCCTAAGAGTAAATAGTGAAATAACTAAGGCTCCCCT

ATCAGCTTCAATGATTAAGCGCTACGATGAACATCATCAAGACTTGACTC

TTTTAAAAGCTTTAGTTCGACAACAACTTCCAGAAAAGTATAAAGAAATC

TTTTTTGATCAATCAAAAAACGGATATGCAGGTTATATTGATGGGGGAGC

TAGCCAAGAAGAATTTTATAAATTTATCAAACCAATTTTAGAAAAAATGG

ATGGTACTGAGGAATTATTGGTGAAACTAAATCGTGAAGATTTGCTGCGC

AAGCAACGGACCTTTGACAACGGCTCTATTCCCCATCAAATTCACTTGGG

TGAGCTGCATGCTATTTTGAGAAGACAAGAAGACTTTTATCCATTTTTAA

AAGACAATCGTGAGAAGATTGAAAAAATCTTGACTTTTCGAATTCCTTAT

TATGTTGGTCCATTGGCGCGTGGCAATAGTCGTTTTGCATGGATGACTCG

GAAGTCTGAAGAAACAATTACCCCATGGAATTTTGAAGAAGTTGTCGATA

AAGGTGCTTCAGCTCAATCATTTATTGAACGCATGACAAACTTTGATAAA

AATCTTCCAAATGAAAAGTACTACCAAAACATAGTTTGCTTTATGAGTA

TTTTACGGTTTATAACGAATTGACAAAGGTCAAATATGTTACTGAGGGAA

TGCGAAAACCAGCATTTCTTTCAGGTGAACAGAAGAAAGCCATTGTTGAT

TTACTCTTCAAAACAAATCGAAAAGTAACCGTTAAGCAATTAAAAGAAGA

TTATTTCAAAAAAATAGAATGTTTTGATAGTGTTGAAATTTCAGGAGTTG

AAGATAGATTTAATGCTTCATTAGGCGCCTACCATGATTTGCTAAAAATT

ATTAAAGATAAAGATTTTTTGGATAATGAAGAAATGAAGATATCTTAGA

GGATATTGTTTTAACATTGACCTTATTTGAAGATAGGGGGATGATTGAGG

AAAGACTTAAAACATATGCTCACCTCTTTGATGATAAGGTGATGAAACAG

CTTAAACGTCGCCGTTATACTGGTTGGGGACGTTTGTCTCGAAAATTGAT

TAATGGTATTAGGGATAAGCAATCTGGCAAAACAATATTAGATTTTTTGA

AATCAGATGGTTTTGCCAATCGCAATTTTATGCAGCTGATCCATGATGAT

AGTTTGACATTTAAAGAAGATATTCAAAAAGCACAGGTGTCTGGACAAGG

CCATAGTTTACATGAACAGATTGCTAACTTAGCTGGCAGTCCTGCTATTA

AAAAAGGTATTTTACGACTGTAAAAATTGTTGATGAACTGGTCAAAGTA

ATGGGGCATAAGCCAGAAAATATCGTTATTGAAATGGCACGTGAAAATCA

GACAACTCAAAAGGGCCAGAAAAATTCGCGAGAGCGTATGAAACGAATCG

AAGAAGGTATCAAAGAATTAGGAAGTCAGATTCTTAAAGAGCATCCTGTT

GAAAATACTCAATTGCAAAATGAAAAGCTCTATCTCTATTATCTACAAAA

TGGAAGAGACATGTATGTGGACCAAGAATTAGATATTAATCGTTTAAGTG

ATTATGATGTCGATCACATTGTTCCACAAAGTTTCATTAAAGACGATTCA

ATAGACAATAAGGTACTAACGCGTTCTGATAAAAATCGTGGTAAATCGGA

TAACGTTCAAGTGAAGAAGTAGTCAAAAAGATGAAAAACTATTGGAGAC

AACTTCTAAACGCCAAGTTAATCACTCAACGTAAGTTTGATAATTTAACG
```

```
-continued
AAAGCTGAACGTGGAGGTTTGAGTGAACTTGATAAAGCTGGTTTTATCAA

ACGCCAATTGGTTGAAACTCGCCAAATCACTAAGCATGTGGCACAAATTT

TGGATAGTCGCATGAATACTAAATACGATGAAAATGATAAACTTATTCGA

GAGGTTAAAGTGATTACCTTAAAATCTAAATTAGTTTCTGACTTCCGAAA

AGATTTCCAATTCTATAAAGTACGTGAGATTAACAATTACCATCATGCCC

ATGATGCGTATCTAAATGCCGTCGTTGGAACTGCTTTGATTAAGAAATAT

CCAAAACTTGAATCGGAGTTTGTCTATGGTGATTATAAAGTTTATGATGT

TCGTAAAATGATTGCTAAGTCTGAGCAAGAAATAGGCAAAGCAACCGCAA

AATATTTCTTTTACTCTAATATCATGAACTTCTTCAAAACAGAAATTACA

CTTGCAAATGGAGAGATTCGCAAACGCCCTCTAATCGAAACTAATGGGGA

AACTGGAGAAATTGTCTGGGATAAAGGGCGAGATTTTGCCACAGTGCGCA

AAGTATTGTCCATGCCCCAAGTCAATATTGTCAAGAAAACAGAAGTACAG

ACAGGCGGATTCTCCAAGGAGTCAATTTTACCAAAAAGAAATTCGGACAA

GCTTATTGCTCGTAAAAAAGACTGGGATCCAAAAAAATATGGTGGTTTTG

ATAGTCCAACGGTAGCTTATTCAGTCCTAGTGGTTGCTAAGGTGGAAAAA

GGGAAATCGAAGAAGTTAAAATCCGTTAAAGAGTTACTAGGGATCACAAT

TATGGAAAGAAGTTCCTTTGAAAAAAATCCGATTGACTTTTTAGAAGCTA

AAGGATATAAGGAAGTTAAAAAAGACTTAATCATTAAACTACCTAAATAT

AGTCTTTTTGAGTTAGAAAACGGTCGTAAACGGATGCTGGCTAGTGCCGG

AGAATTACAAAAGGAAATGAGCTGGCTCTGCCAAGCAAATATGTGAATT

TTTTATATTTAGCTAGTCATTATGAAAAGTTGAAGGGTAGTCCAGAAGAT

AACGAACAAAAACAATTGTTTGTGGAGCAGCATAAGCATTATTTAGATGA

GATTATTGAGCAAATCAGTGAATTTTCTAAGCGTGTTATTTTAGCAGATG

CCAATTTAGATAAAGTTCTTAGTGCATATAACAAACATAGAGACAAACCA

ATACGTGAACAAGCAGAAAATATTATTCATTTATTTACGTTGACGAATCT

TGGAGCTCCCGCTGCTTTTAAATATTTTGATACAACAATTGATCGTAAAC

GATATACGTCTACAAAAGAAGTTTTAGATGCCACTCTTATCCATCAATCC

ATCACTGGTCTTTATGAAACACGCATTGATTTGAGTCAGCTAGGAGGTGA

CTGA

S. pyogenes Cas9 protein (GENBANK ® accession no.
AKP81606.1):
                                            (SEQ ID NO: 10)
MDKKYSIGLDIGTNSVGWAVITDDYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNSLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD.
```

An APOBEC-Cas9 fusion polypeptide used in the methods provided herein can include the full-length amino acid sequence of a Cas9 protein, or a fragment of a Cas9 protein. Typically, an APOBEC-Cas9 fusion polypeptide includes a Cas9 fragment that can bind to a gRNA, but does not include a functional nuclease domain. For example, the fusion may contain a non-functional nuclease domain, or a portion of a nuclease domain that is not sufficient to confer nuclease activity, or may lack a nuclease domain altogether. Thus, in some cases, an APOBEC-Cas9 fusion polypeptide can contain a fragment of Cas9, such as a fragment including the Cas9 gRNA binding domain, or a fragment that includes both the gRNA binding domain and an inactivated version of the DNA cleavage domain. The Cas portion of an APOBEC-Cas9 fusion also may contain a variant Cas polypeptide having an amino acid sequence that is at least about 90% identical to a wild type Cas9 sequence (e.g., at least about 91%, 92%, 93%, 94%, 95%, 96%, 97%, 98%, 99%, 99.5%, or 99.8% identical to a wild type Cas9 amino acid sequence).

In some embodiments, an APOBEC-Cas9 fusion polypeptide can include a "nuclease-dead" Cas9 polypeptide that lacks nuclease activity and may or may not have nickase activity (such that it cuts one strand of a double-stranded DNA), but can bind to a preselected target sequence when complexed with a gRNA. Without being bound by a particular mechanism, the use of a DNA targeting polypeptide with nickase activity, where the nickase generates a strand-specific cut on the strand opposing the uracil to be modified, can have the subsequent effect of directing repair machinery to non-modified strand, resulting in repair of the nick so both strands are modified. For example, with respect to the Cas9 sequence of SEQ ID NO:10, a Cas9 polypeptide can be a D10A Cas9 polypeptide (or a portion thereof) that has nickase activity but not nuclease activity, or a H840A Cas9 polypeptide (or a portion thereof) that has nickase activity but not nuclease activity.

In some embodiments, a "nuclease-dead" polypeptide can be a D10A H840A Cas9 polypeptide (or a portion thereof) that has neither nickase nor nuclease activity. A Cas9 polypeptide also can be a D10A D839A H840A N863A Cas9 polypeptide in which alanine residues are substituted for the aspartic acid residues at positions 10 and 839, the histidine residue at position 840, and the asparagine residue at position 863 (with respect to SEQ ID NO:10). See, e.g., Mali et al., *Nature Biotechnol*, supra; Jinek et al., supra; and Qi et al., *Cell* 152(5):1173-83, 2013.

An exemplary reference Cas9 amino acid sequence having an inactivated nuclease domain with D10A and H840A mutations (underlined) is:

```
                                          (SEQ ID NO: 11)
MDKKYSIGLAIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDAIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD.
```

An exemplary reference Cas9 amino acid sequence having an inactivated nuclease domain with a D10A mutation (underlined) is:

```
                                          (SEQ ID NO: 12)
MDKKYSIGLAIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI

LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDHIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD.
```

An exemplary reference Cas9 amino acid sequence having an inactivated nuclease domain with a H840A mutation (underlined) is:

```
                                          (SEQ ID NO: 13)
MDKKYSIGLDIGTNSVGWAVITDEYKVPSKKFKVLGNTDRHSIKKNLIGA

LLFDSGETAEATRLKRTARRRYTRRKNRICYLQEIFSNEMAKVDDSFFHR

LEESFLVEEDKKHERHPIFGNIVDEVAYHEKYPTIYHLRKKLVDSTDKAD

LRLIYLALAHMIKFRGHFLIEGDLNPDNSDVDKLFIQLVQTYNQLFEENP

INASGVDAKAILSARLSKSRRLENLIAQLPGEKKNGLFGNLIALSLGLTP

NFKSNFDLAEDAKLQLSKDTYDDDLDNLLAQIGDQYADLFLAAKNLSDAI
```

```
LLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLR

KQRTFDNGSIPHQIHLGELHAILRRQEDFYPFLKDNREKIEKILTFRIPY

YVGPLARGNSRFAWMTRKSEETITPWNFEEVVDKGASAQSFIERMTNFDK

NLPNEKVLPKHSLLYEYFTVYNELTKVKYVTEGMRKPAFLSGEQKKAIVD

LLFKTNRKVTVKQLKEDYFKKIECFDSVEISGVEDRFNASLGTYHDLLKI

IKDKDFLDNEENEDILEDIVLTLTLFEDREMIEERLKTYAHLFDDKVMKQ

LKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKV

MGRHKPENIVIEMARENQTTQKGQKNSRERMKRIEEGIKELGSQILKEHP

VENTQLQNEKLYLYYLQNGRDMYVDQELDINRLSDYDVDAIVPQSFLKDD

SIDNKVLTRSDKNRGKSDNVPSEEVVKKMKNYWRQLLNAKLITQRKFDNL

TKAERGGLSELDKAGFIKRQLVETRQITKHVAQILDSRMNTKYDENDKLI

REVKVITLKSKLVSDFRKDFQFYKVREINNYHHAHDAYLNAVVGTALIKK

YPKLESEFVYGDYKVYDVRKMIAKSEQEIGKATAKYFFYSNIMNFFKTEI

TLANGEIRKRPLIETNGETGEIVWDKGRDFATVRKVLSMPQVNIVKKTEV

QTGGFSKESILPKRNSDKLIARKKDWDPKKYGGFDSPTVAYSVLVVAKVE

KGKSKKLKSVKELLGITIMERSSFEKNPIDFLEAKGYKEVKKDLIIKLPK

YSLFELENGRKRMLASAGELQKGNELALPSKYVNFLYLASHYEKLKGSPE

DNEQKQLFVEQHKHYLDEIIEQISEFSKRVILADANLDKVLSAYNKHRDK

PIREQAENIIHLFTLTNLGAPAAFKYFDTTIDRKRYTSTKEVLDATLIHQ

SITGLYETRIDLSQLGGD.
```

In some embodiments, Cas9 variants containing mutations other than D10A and H840A and lacking nuclease activity are provided herein. Such variants include, without limitation, include other amino acid substitutions at D10 and H840, or other substitutions within the Cas9 nuclease domains. In some embodiments, a Cas9 variant can have one or more amino acid additions or deletions (e.g., one, two, three, four, five, six, seven, eight, nine, 10, 10 to 20, 20 to 40, 40 to 50, or 50 to 100 additions or deletions) as compared to a reference Cas9 sequence (e.g., the sequence set forth in SEQ ID NO:10. It is noted, for example, that Cas9 has two separate nuclease domains that allow it to cut both strands of a double-stranded DNA. These are referred to as the "RuvC" and "HNH" domains. Each includes several active site metal-chelating residues. In the RuvC domain, the metal-chelating residues are D10, E762, H983, and D986, while in the HNH domain, the metal-chelating residues are D839, H840, and N863. Mutation of one or more of these residues (e.g., by substituting an alanine for the natural amino acid) may convert Cas9 into a nickase, while mutating one residue from each domain can result in a nuclease-dead and nickase-dead Cas9.

The Cas9 sequence used in an APOBEC-Cas9 fusion polypeptide also can be based on natural or engineered Cas9 molecules from organisms such as *Corynebacterium ulcerans* (NCBI Refs: NC_015683.1 and NC_017317.1), *C. diphtheria* (NCBI Refs: NC_016782.1 and NC_016786.1), *Spiroplasma syrphidicola* (NCBI Ref: NC_021284.1), *Prevotella intermedia* (NCBI Ref: NC_017861.1), *Spiroplasma taiwanense* (NCBI Ref: NC_021846.1), *Streptococcus iniae* (NCBI Ref: NC_021314.1), *Belliella baltica* (NCBI Ref: NC_018010.1), *Psychroflexus torquis* (NCBI Ref: NC_018721.1), *Streptococcus thermophilus* (NCBI Ref: YP_820832.1), *Listeria innocua* (NCBI Ref: NP_472073.1), *Campylobacter jejuni* (NCBI Ref: YP_002344900.1), *Neisseria meningitidis* (NCBI Ref: YP_002342100.1), and *Francisella novicida*. RNA-guided nucleases that have similar activity to Cas9 but are from other types of CRISPR/Cas systems, such as *Acidaminococcus* sp. or *Lachnospiraceae* bacterium ND2006 Cpf1 (see, e.g., Yamano et al., *Cell* 165(4):949-962, 2016; and Dong et al., *Nature* 532(7600): 522-526, 2016) also can be used in fusion polypeptides with APOBEC deaminases.

The domains within APOBEC-Cas9 fusion polypeptides provided herein can be positioned in any suitable configuration. For example, the APOBEC portion can be coupled to the N-terminus of the Cas9 portion, either directly or via a linker. Alternatively, the APOBEC portion can be fused to the C-terminus of the Cas9 portion, either directly or via a linker. In some cases, the APOBEC portion can be fused within an internal loop of Cas9. Suitable linkers include, without limitation, an amino acid or a plurality of amino acids (e.g., five to 50 amino acids, 10 to 20 amino acids, 15 to 25 amino acids, or 25 to 50 amino acids, such as $(GGGGS)_n$ (SEQ ID NO:14), $(G)n$, $(EAAAK)_n$ (SEQ ID NO:15), $(GGS)_n$, a SGSETPGTSESATPES (SEQ ID NO:16) motif (see, e.g., Guilinger et al., *Nat Biotechnol* 32(6):577-582, 2014), an $(XP)_n$ motif, or a combination thereof, where n is independently 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30). Suitable linkers also include organic groups, polymers, and chemical moieties. Useful linker motifs also are described elsewhere (see, e.g., Chen et al., *Adv Drug Deliv Rev* 65(10): 1357-1369, 2013). When included, a linker can be connected to each domain via a covalent bond, for example.

Additional components that may be present in an APOBEC-Cas9 fusion polypeptide include one or more nuclear localization sequences (NLS), cytoplasmic localization sequences, export sequences (e.g., a nuclear export sequence), or sequence tags that are useful for solubilization, purification, or detection of the fusion protein. Suitable localization signal sequences and sequences of protein tags include, without limitation, biotin carboxylase carrier protein (BCCP) tags, myc-tags, calmodulin-tags, FLAG-tags, hemagglutinin (HA)-tags, polyhistidine tags, also referred to as histidine tags or His-tags, maltose binding protein (MBP)-tags, nus-tags, glutathione-S-transferase (GST)-tags, green fluorescent protein (GFP)-tags, thioredoxin-tags, S-tags, Softags (e.g., Softag 1, Softag 3), strep-tags, biotin ligase tags, FlAsH tags, V5 tags, and SBP-tags. Fusion polypeptides also can include other functional domains, such as, without limitation, a domain from the bacteriophage UGI protein that is a universal inhibitor of uracil DNA glycosylase enzymes (UNG2 in human cells; see, e.g., Di Noia and Neuberger, *Nature* 419(6902):43-48, 2002) that can prevent the deaminated cytosine (DNA uracil) from being repaired by cellular base excision repair (see, e.g., Komor et al., *Nature* 533(7603):420-424, 2016; and Mol et al., *Cell* 82:701-708, 1995).

To target an APOBEC-Cas9 fusion polypeptide to a target site, the APOBEC-Cas9 fusion can be co-expressed with a gRNA that allows for Cas9 binding and confers sequence specificity to the APOBEC-Cas9 fusion polypeptide. Suitable gRNA sequences typically include guide sequences that are complementary to a nucleotide sequence within about 50

(e.g., 25 to 50, 40 to 50, 40 to 60, or 50 to 75) nucleotides upstream or downstream of the target nucleotide to be edited.

This document also provides methods for using an ACE reporter system as described herein to monitor the activity of APOBEC-Cas9 base editing complexes. Thus, a CRISPR RNA (gRNA) targeted to a particular sequence (e.g., in a genome or in an extrachromosomal plasmid) can act to direct the Cas9 portion of an APOBEC-Cas9 fusion polypeptide to a selected target sequence, permitting the APOBEC portion of the fusion to modify a particular cytosine residue at the desired sequence. When a particular (mutant) cytosine in the target sequence of an ACE reporter is deaminated, the restored activity of the reporter can serve as an indicator of base editing activity, and can be quantified (e.g., by comparison to a second reporter to determine a signal ratio) to indicate the level of base editing activity.

Thus, the methods provided herein can include contacting a reporter nucleic acid with an APOBEC-Cas9 fusion polypeptide in the presence of one or more CRISPR RNA molecules. The methods also can include contacting another target nucleic acid with the APOBEC-Cas9 fusion polypeptide, and the activity of the reporter (e.g., determined based on a signal generated by the reporter, or based on a ratio of signals from two reporters) can indicate activity of the APOBEC-Cas9 fusion. In some embodiments, the methods can include introducing (e.g., by transformation, transfection, transduction, or infection) into a cell (e.g., a bacterial, plant, or animal cell) (i) a reporter nucleic acid as described herein, (ii) a nucleic acid encoding an APOBEC-Cas9 fusion polypeptide, and (iii) a nucleic acid containing a gRNA sequence targeted to a DNA sequence of interest within the reporter. Such methods also can include maintaining the cell under conditions in which the nucleic acids are expressed. The nucleic acids can be introduced into cells using methods such as those known in the art. For example, a nucleic acid (e.g., an expression vector) encoding first and second reporters in an ACE system, as provided herein, and/or a nucleic acid (e.g., an expression vector) encoding an APOBEC-Cas9 fusion, can be introduced into a cell by transfection, transformation, transduction, or infection techniques such as transformation using calcium or polyethylene glycol (PEG), electroporation, or liposome-mediated transfection. It is noted that an APOBEC-Cas9 fusion polypeptide also can be introduced into a cell as a polypeptide per se, using delivery vectors associated or combined with any cellular permeabilization techniques, such as sonoporation, electroporation, lipofection, or derivatives of these or other related techniques.

When a first nucleic acid encoding an APOBEC-Cas9 fusion polypeptide and a second nucleic acid containing a gRNA are used, the first and second nucleic acids can be included within a single construct, or in separate constructs. Thus, while in some cases it may be most efficient to include sequences encoding the APOBEC-Cas9 polypeptide, and the gRNA in a single construct (e.g., a single vector), in other cases first nucleic acid and the second nucleic acid can be present in separate nucleic acid constructs (e.g., separate vectors). In some embodiments, separate crRNA and tracrRNAs can be used, and the crRNA and the tracrRNA can be in separate nucleic acid constructs (e.g., separate vectors). Again, a "vector" is a replicon, such as a plasmid, phage, or cosmid, into which another DNA segment may be inserted so as to bring about the replication of the inserted segment.

After a nucleic acid is contacted with an APOBEC-Cas9 fusion polypeptide and CRISPR RNA, or after a cell is transfected or transformed with an APOBEC-Cas9 fusion and a CRISPR RNA, or with one or more nucleic acids encoding the fusion and the CRISPR RNA, any suitable method can be used to determine whether mutagenesis has occurred at the target site. In some embodiments, a phenotypic change can indicate that a change has occurred the target site (e.g., editing of the ACE reporter to generate a mCherry-positive signal or an eGFP-positive signal). PCR-based methods also can be used to ascertain whether a target site contains a desired mutation.

The nucleic acids (and, in some cases, fusion polypeptides) described herein, or compositions containing the nucleic acids (and, in some cases, polypeptides), can be administered to a cell or to a subject (e.g., a human, a non-human mammal such as a non-human primate, a rodent, a sheep, a goat, a cow, a bat, a cat, a dog, a pig, or a rabbit, an amphibian, a reptile, a fish, or an insect) in order to specifically modify a targeted DNA sequence. In some cases, the targeted sequence can be selected based on its association with a particular clinical condition or disease, and the administration can be aimed at treating the clinical condition or disease. The term "treating" refer to reversal, alleviation, delaying the onset, or inhibiting the progress of the condition or disease, or one or more symptoms of the condition or disease. In some cases, administration can occur after onset of the clinical condition or disease (after one or more symptoms of the condition have developed, for example, or after the disease has been diagnosed). In some cases, however, administration may occur in the absence of symptoms, such that onset or progression of the clinical condition or disease is prevented or delayed. This may be the case when the subject is identified as being susceptible to the condition, for example, or when the subject has been previously treated for the condition and symptoms have resolved, but recurrence is possible.

In some embodiments, the methods provided herein can be used to introduce a point mutation into a target (non-marker) nucleic acid by deaminating a target cytosine. For example, the targeted deamination of a particular cytosine may correct a genetic defect (e.g., a genetic defect is associated with a clinical condition or disease). In some embodiments, the methods provided herein can be used to introduce a deactivating point mutation into a sequence encoding a gene product associated with a clinical condition or disease (e.g., an oncogene). In some cases, for example, a deactivating mutation can create a premature stop codon in a coding sequence, resulting in the expression of a truncated gene product that may not be functional, or may lack the normal function of the full-length protein.

In some embodiments, the methods provided can be used to restore the function of a dysfunctional gene. For example, an APOBEC-Cas9 fusion polypeptide can be used in vitro or in vivo to correct a disease-associated mutation (e.g., in cell culture or in a subject). Thus, this document provides methods for treating subjects identified as having a clinical condition or disease that is associated with a point mutation. Such methods can include administering to a subject an APOBEC-Cas9 fusion polypeptide, or a nucleic acid encoding an APOBEC-Cas9 fusion polypeptide, in an amount effective to correct the point mutation or to introduce a deactivating mutation into the sequence associated with the disease. The disease can be, without limitation, a proliferative disease, a genetic disease, or a metabolic disease.

It is to be noted that, while the examples provided herein relate to APOBEC-Cas9 fusions, the use of other DNA-targeting molecules is contemplated. Thus, for example, a modified APOBEC polypeptide can be coupled to a DNA-targeting domain from a polypeptide such as a meganuclease (e.g., a wild type or variant protein of the homing endonuclease family, such as those belonging to the dodecapeptide family (LAGLIDADG; SEQ ID NO:17), a transcription activator-like (TAL) effector protein, or a zinc-finger (ZF) protein. Such proteins and their characteristics, function, and use are described elsewhere. See, e.g., WO 2004/067736/ Porteus, Nature 459:337-338, 2009; Porteus and Baltimore, Science 300:763, 2003; Bogdanove et al., Curr Opin Plant Biol 13:394-401, 2010; and Boch et al., Science 326(5959): 1509-1512, 2009.

The invention will be further described in the following examples, which do not limit the scope of the invention described in the claims.

EXAMPLES

Example 1—Materials and Methods

Cell Lines:

293T cells were maintained in Dulbecco's Modified Eagle's Medium (DMEM; Hyclone) supplemented with 10% fetal bovine serum (FBS; Gibco) and 0.5% penicillin/ streptomycin. HeLa cells were maintained in Roswell Park Memorial Institute (RPMI; Hyclone) supplemented with 10% FBS (Gibco) and 0.5% penicillin/streptomycin. 293T and HeLa cells were transfected with TransIT LTI (Minis) according to the manufacturer's protocol. SSM2c, CHO, and COS-7 cells were maintained in DMEM (Euroclone) supplemented with 10% FBS (Carlo Erba), 2 mM L-glutamine (Carlo Erba), and 1 mM penicillin/streptomycin (Carlo Erba). SSM2c were transfected with PEI (Sigma-Aldrich) according to the manufacturer's protocol. CHO and COS-7 cells were transfected with LIPOFECTAMINE® LTX (Invitrogen) according to the manufacturer's protocol. Single time point episomal editing experiments were harvested 72 hours post-transfection, and chromosomal editing experiments were harvested 96 hours post-transfection.

Base Editing Constructs:

The rat APOBEC1-Cas9-UGI-NLS construct (BE3) was provided by David Liu at Harvard University (Komor et al., supra). A3A and A3Bctd cDNA sequences, each disrupted by an L1 intron to prevent toxicity in E. coli (Hultquist et al., J Virol 85:11220-11234, 2011), were amplified using the primers listed in TABLE 1 and used to replace rat APOBEC1 in BE3 using a NotI site in the multiple cloning site (MCS) and a XmaI site in the XTEN linker. gRNAs targeting mCherry or non-specific (NS) sequence as a control (TABLE 1) were cloned into MLM3636 obtained from J. Keith Joung at Harvard University, through Addgene (Plasmid #43860) using the associated protocol (see, "Joung Lab gRNA Cloning Protocol," Version 1.2. October, 2015; available online at media.addgene.org/data/plasmids/43/43860/ 43860-attachment_T35tt6ebKxov.pdf). An L1 intron was amplified from the A3Ai construct using primers in TABLE 1 and cloned into the SacI site in the rat APOBEC1 region of BE3 to create the BE3i editing construct. The nucleotide sequence of BE3i follows, with the intron in lower case:

(SEQ ID NO: 125)

```
ATATGCCAAGTACGCCCCCTATTGACGTCAATGACGGTAAATGGCCCGCCTGGC

ATTATGCCCAGTACATGACCTTATGGGACTTTCCTACTTGGCAGTACATCTACGT

ATTAGTCATCGCTATTACCATGGTGATGCGGTTTTGGCAGTACATCAATGGGCG

TGGATAGCGGTTTGACTCACGGGGATTTCCAAGTCTCCACCCCATTGACGTCA

ATGGGAGTTTGTTTTGGCACCAAAATCAACGGGACTTTCCAAAATGTCGTAAC

AACTCCGCCCCATTGACGCAAATGGGCGGTAGGCGTGTACGGTGGGAGGTCTA

TATAAGCAGAGCTGGTTTAGTGAACCGTCAGATCCGCTAGAGATCCGCGGCCG

CTAATACGACTCACTATAGGGAGAGCCGCCACCATGAGCTCAGAGACTGGCCC

AGTGGCTGTGGACCCCACATTGAGgtgagtccaggagatgtttcagcactgttgcctttagtctcgaggca acttagacaactgagtattgatctgagcacagcagggtgtgagctgtttgaagatactgggggttggggggtgaagaaactgcaga ggactaactgggctgagacccagtggcaatgttttagggcctaaggaatgcctctgaaaatctagatggacaactttgactttgag aaaagagaggtggaaatgaggaaaatgactttattattagatttcggtagaaagaactttcatctttccctattttttgttattcgtttt aaaacatctatctggaggcaggacaagtatggtcattaaaaagatgcaggcagaaggcatatattggctcagtcaaagtgggga actttggtggccaaacatacattgctaaggctattcctatatcagctggacacatataaaatgctgctaatgcttcattacaaacttat atcctttaattccagatggggcaaagtatgtccaggggtgaggaacaattgaaacatttgggctggagtagattttgaaagtcag ctctgtgtgtgtgtgtgtgtgtgtgtgtgtgtgtgtgcgcgcacgtgtgtttgtgtgtgtgtgagagcgtgtgtttcttttaacgttttc agcctacagcatacagggttcatggtggcaagaagataacaagatttaaattatggccagtgactagtgctgcaagaagaacaa ctacctgcatttaatgggaaagcaaaatctcaggctttgagggaagttaacataggcttgattctgggtggaagctgggtgtgtagt tatctggaggccaggctggagactcagctcactatgggttcatattattgtacctttcatctcaacagACGGCGGATCG

AGCCCCATGAGTTTGAGGTATTCTTCGATCCGAGAGAGCTCCGCAAGGAGACC

TGCCTGCTTTACGAAATTAATTGGGGGGGCCGGCACTCCATTTGGCGACATAC

ATCACAGAACACTAACAAGCACGTCGAAGTCAACTTCATCGAGAAGTTCACG
```

```
ACAGAAAGATATTTCTGTCCGAACACAAGGTGCAGCATTACCTGGTTTCTCAG

CTGGAGCCCATGCGGCGAATGTAGTAGGGCCATCACTGAATTCCTGTCAAGGT

ATCCCCACGTCACTCTGTTTATTTACATCGCAAGGCTGTACCACCACGCTGACC

CCCGCAATCGACAAGGCCTGCGGGATTTGATCTCTTCAGGTGTGACTATCCAA

ATTATGACTGAGCAGGAGTCAGGATACTGCTGGAGAAACTTTGTGAATTATAG

CCCGAGTAATGAAGCCCACTGGCCTAGGTATCCCCATCTGTGGGTACGACTGT

ACGTTCTTGAACTGTACTGCATCATACTGGGCCTGCCTCCTTGTCTCAACATTC

TGAGAAGGAAGCAGCCACAGCTGACATTCTTTACCATCGCTCTTCAGTCTTGT

CATTACCAGCGACTGCCCCCACACATTCTCTGGGCCACCGGGTTGAAAAGCGG

CAGCGAGACTCCCGGGACCTCAGAGTCCGCCACACCCGAAAGTGATAAAAAG

TATTCTATTGGTTTAGCCATCGGCACTAATTCCGTTGGATGGGCTGTCATAACCG

ATGAATACAAAGTACCTTCAAAGAAATTTAAGGTGTTGGGGAACACAGACCGT

CATTCGATTAAAAAGAATCTTATCGGTGCCCTCCTATTCGATAGTGGCGAAACG

GCAGAGGCGACTCGCCTGAAACGAACCGCTCGGAGAAGGTATACACGTCGCA

AGAACCGAATATGTTACTTACAAGAAATTTTTAGCAATGAGATGGCCAAAGTT

GACGATTCTTTCTTTCACCGTTTGGAAGAGTCCTTCCTTGTCGAAGAGGACAA

GAAACATGAACGGCACCCCATCTTTGGAAACATAGTAGATGAGGTGGCATATC

ATGAAAAGTACCCAACGATTTATCACCTCAGAAAAAAGCTAGTTGACTCAACT

GATAAAGCGGACCTGAGGTTAATCTACTTGGCTCTTGCCCATATGATAAAGTTC

CGTGGGCACTTTCTCATTGAGGGTGATCTAAATCCGGACAACTCGGATGTCGA

CAAACTGTTCATCCAGTTAGTACAAACCTATAATCAGTTGTTTGAAGAGAACC

CTATAAATGCAAGTGGCGTGGATGCGAAGGCTATTCTTAGCGCCCGCCTCTCTA

AATCCCGACGGCTAGAAAACCTGATCGCACAATTACCCGGAGAGAAGAAAAA

TGGGTTGTTCGGTAACCTTATAGCGCTCTCACTAGGCCTGACACCAAATTTTAA

GTCGAACTTCGACTTAGCTGAAGATGCCAAATTGCAGCTTAGTAAGGACACGT

ACGATGACGATCTCGACAATCTACTGGCACAAATTGGAGATCAGTATGCGGAC

TTATTTTTGGCTGCCAAAAACCTTAGCGATGCAATCCTCCTATCTGACATACTG

AGAGTTAATACTGAGATTACCAAGGCGCCGTTATCCGCTTCAATGATCAAAAG

GTACGATGAACATCACCAAGACTTGACACTTCTCAAGGCCCTAGTCCGTCAGC

AACTGCCTGAGAAATATAAGGAAATATTCTTTGATCAGTCGAAAAACGGGTAC

GCAGGTTATATTGACGGCGGAGCGAGTCAAGAGGAATTCTACAAGTTTATCAA

ACCCATATTAGAGAAGATGGATGGGACGGAAGAGTTGCTTGTAAAACTCAATC

GCGAAGATCTACTGCGAAAGCAGCGGACTTTCGACAACGGTAGCATTCCACAT

CAAATCCACTTAGGCGAATTGCATGCTATACTTAGAAGGCAGGAGGATTTTTAT

CCGTTCCTCAAAGACAATCGTGAAAAGATTGAGAAAATCCTAACCTTTCGCAT

ACCTTACTATGTGGGACCCCTGGCCCGAGGGAACTCTCGGTTCGCATGGATGA

CAAGAAAGTCCGAAGAAACGATTACTCCATGGAATTTTGAGGAAGTTGTCGAT

AAAGGTGCGTCAGCTCAATCGTTCATCGAGAGGATGACCAACTTTGACAAGA

ATTTACCGAACGAAAAAGTATTGCCTAAGCACAGTTTACTTTACGAGTATTTCA

CAGTGTACAATGAACTCACGAAAGTTAAGTATGTCACTGAGGGCATGCGTAAA
```

-continued

```
CCCGCCTTTCTAAGCGGAGAACAGAAGAAAGCAATAGTAGATCTGTTATTCAA

GACCAACCGCAAAGTGACAGTTAAGCAATTGAAAGAGGACTACTTTAAGAAA

ATTGAATGCTTCGATTCTGTCGAGATCTCCGGGGTAGAAGATCGATTTAATGCG

TCACTTGGTACGTATCATGACCTCCTAAAGATAATTAAAGATAAGGACTTCCTG

GATAACGAAGAGAATGAAGATATCTTAGAAGATATAGTGTTGACTCTTACCCTC

TTTGAAGATCGGGAAATGATTGAGGAAAGACTAAAAACATACGCTCACCTGTT

CGACGATAAGGTTATGAAACAGTTAAAGAGGCGTCGCTATACGGGCTGGGGAC

GATTGTCGCGGAAACTTATCAACGGGATAAGAGACAAGCAAAGTGGTAAAAC

TATTCTCGATTTTCTAAAGAGCGACGGCTTCGCCAATAGGAACTTTATGCAGCT

GATCCATGATGACTCTTTAACCTTCAAAGAGGATATACAAAAGGCACAGGTTT

CCGGACAAGGGGACTCATTGCACGAACATATTGCGAATCTTGCTGGTTCGCCA

GCCATCAAAAAGGGCATACTCCAGACAGTCAAAGTAGTGGATGAGCTAGTTAA

GGTCATGGGACGTCACAAACCGGAAAACATTGTAATCGAGATGGCACGCGAA

AATCAAACGACTCAGAAGGGGCAAAAAAACAGTCGAGAGCGGATGAAGAGA

ATAGAAGAGGGTATTAAAGAACTGGGCAGCCAGATCTTAAAGGAGCATCCTGT

GGAAAATACCCAATTGCAGAACGAGAAACTTTACCTCTATTACCTACAAAATG

GAAGGGACATGTATGTTGATCAGGAACTGGACATAAACCGTTTATCTGATTACG

ACGTCGATCACATTGTACCCCAATCCTTTTTGAAGGACGATTCAATCGACAATA

AAGTGCTTACACGCTCGGATAAGAACCGAGGGAAAAGTGACAATGTTCCAAG

CGAGGAAGTCGTAAAGAAAATGAAGAACTATTGGCGGCAGCTCCTAAATGCG

AAACTGATAACGCAAAGAAAGTTCGATAACTTAACTAAAGCTGAGAGGGGTG

GCTTGTCTGAACTTGACAAGGCCGGATTTATTAAACGTCAGCTCGTGGAAACC

CGCCAAATCACAAAGCATGTTGCACAGATACTAGATTCCCGAATGAATACGAA

ATACGACGAGAACGATAAGCTGATTCGGGAAGTCAAAGTAATCACTTTAAAGT

CAAAATTGGTGTCGGACTTCAGAAAGGATTTTCAATTCTATAAAGTTAGGGAG

ATAAATAACTACCACCATGCGCACGACGCTTATCTTAATGCCGTCGTAGGGACC

GCACTCATTAAGAAATACCCGAAGCTAGAAAGTGAGTTTGTGTATGGTGATTA

CAAAGTTTATGACGTCCGTAAGATGATCGCGAAAAGCGAACAGGAGATAGGC

AAGGCTACAGCCAAATACTTCTTTTATTCTAACATTATGAATTTCTTTAAGACGG

AAATCACTCTGGCAAACGGAGAGATACGCAAACGACCTTTAATTGAAACCAAT

GGGGAGACAGGTGAAATCGTATGGGATAAGGGCCGGGACTTCGCGACGGTGA

GAAAAGTTTTGTCCATGCCCCAAGTCAACATAGTAAAGAAAACTGAGGTGCA

GACCGGAGGGTTTTCAAAGGAATCGATTCTTCCAAAAAGGAATAGTGATAAGC

TCATCGCTCGTAAAAAGGACTGGGACCCGAAAAAGTACGGTGGCTTCGATAG

CCCTACAGTTGCCTATTCTGTCCTAGTAGTGGCAAAAGTTGAGAAGGGAAAAT

CCAAGAAACTGAAGTCAGTCAAAGAATTATTGGGGATAACGATTATGGAGCGC

TCGTCTTTTGAAAAGAACCCCATCGACTTCCTTGAGGCGAAAGGTTACAAGGA

AGTAAAAAAGGATCTCATAATTAAACTACCAAAGTATAGTCTGTTTGAGTTAGA

AAATGGCCGAAAACGGATGTTGGCTAGCGCCGGAGAGCTTCAAAAGGGGAAC

GAACTCGCACTACCGTCTAAATACGTGAATTTCCTGTATTTAGCGTCCCATTAC

GAGAAGTTGAAAGGTTCACCTGAAGATAACGAACAGAAGCAACTTTTTGTTG
```

-continued

AGCAGCACAAACATTATCTCGACGAAATCATAGAGCAAATTTCGGAATTCAGT

AAGAGAGTCATCCTAGCTGATGCCAATCTGGACAAAGTATTAAGCGCATACAA

CAAGCACAGGGATAAACCCATACGTGAGCAGGCGGAAAATATTATCCATTTGT

TTACTCTTACCAACCTCGGCGCTCCAGCCGCATTCAAGTATTTTGACACAACGA

TAGATCGCAAACGATACACTTCTACCAAGGAGGTGCTAGACGCGACACTGATT

CACCAATCCATCACGGGATTATATGAAACTCGGATAGATTTGTCACAGCTTGGG

GGTGACTCTGGTGGTTCTACTAATCTGTCAGATATTATTGAAAAGGAGACCGGT

AAGCAACTGGTTATCCAGGAATCCATCCTCATGCTCCCAGAGGAGGTGGAAGA

AGTCATTGGGAACAAGCCGGAAAGCGATATACTCGTGCACACCGCCTACGACG

AGAGCACCGACGAGAATGTCATGCTTCTGACTAGCGACGCCCCTGAATACAAG

CCTTGGGCTCTGGTCATACAGGATAGCAACGGTGAGAACAAGATTAAGATGCT

CTCTGGTGGTTCTCCCAAGAAGAAGAGGAAAGTCTAACCGGTCATCATCACCA

TCACCATTGAGTTTAAACCCGCTGATCAGCCTCGACTGTGCCTTCTAGTTGCCA

GCCATCTGTTGTTTGCCCCTCCCCCGTGCCTTCCTTGACCCTGGAAGGTGCCA

CTCCCACTGTCCTTTCCTAATAAAATGAGGAAATTGCATCGCATTGTCTGAGTA

GGTGTCATTCTATTCTGGGGGGTGGGGTGGGGCAGGACAGCAAGGGGGAGGA

TTGGGAAGACAATAGCAGGCATGCTGGGGATGCGGTGGGCTCTATGGCTTCTG

AGGCGGAAAGAACCAGCTGGGGCTCGATACCGTCGACCTCTAGCTAGAGCTT

GGCGTAATCATGGTCATAGCTGTTTCCTGTGTGAAATTGTTATCCGCTCACAATT

CCACACAACATACGAGCCGGAAGCATAAAGTGTAAAGCCTAGGGTGCCTAATG

AGTGAGCTAACTCACATTAATTGCGTTGCGCTCACTGCCCGCTTTCCAGTCGG

GAAACCTGTCGTGCCAGCTGCATTAATGAATCGGCCAACGCGCGGGGAGAGG

CGGTTTGCGTATTGGGCGCTCTTCCGCTTCCTCGCTCACTGACTCGCTGCGCTC

GGTCGTTCGGCTGCGGCGAGCGGTATCAGCTCACTCAAAGGCGGTAATACGGT

TATCCACAGAATCAGGGGATAACGCAGGAAAGAACATGTGAGCAAAAGGCCA

GCAAAAGGCCAGGAACCGTAAAAAGGCCGCGTTGCTGGCGTTTTTCCATAGG

CTCCGCCCCCCTGACGAGCATCACAAAAATCGACGCTCAAGTCAGAGGTGGC

GAAACCCGACAGGACTATAAAGATACCAGGCGTTTCCCCCTGGAAGCTCCCTC

GTGCGCTCTCCTGTTCCGACCCTGCCGCTTACCGGATACCTGTCCGCCTTTCTC

CCTTCGGGAAGCGTGGCGCTTTCTCATAGCTCACGCTGTAGGTATCTCAGTTCG

GTGTAGGTCGTTCGCTCCAAGCTGGGCTGTGTGCACGAACCCCCCGTTCAGCC

CGACCGCTGCGCCTTATCCGGTAACTATCGTCTTGAGTCCAACCCGGTAAGAC

ACGACTTATCGCCACTGGCAGCAGCCACTGGTAACAGGATTAGCAGAGCGAG

GTATGTAGGCGGTGCTACAGAGTTCTTGAAGTGGTGGCCTAACTACGGCTACA

CTAGAAGAACAGTATTTGGTATCTGCGCTCTGCTGAAGCCAGTTACCTTCGGA

AAAAGAGTTGGTAGCTCTTGATCCGGCAAACAAACCACCGCTGGTAGCGGTG

GTTTTTTTGTTTGCAAGCAGCAGATTACGCGCAGAAAAAAAGGATCTCAAGAA

GATCCTTTGATCTTTTCTACGGGGTCTGACGCTCAGTGGAACGAAAACTCACG

TTAAGGGATTTTGGTCATGAGATTATCAAAAAGGATCTTCACCTAGATCCTTTT

AAATTAAAAATGAAGTTTTAAATCAATCTAAAGTATATATGAGTAAACTTGGTC

-continued

```
TGACAGTTACCAATGCTTAATCAGTGAGGCACCTATCTCAGCGATCTGTCTATT

TCGTTCATCCATAGTTGCCTGACTCCCCGTCGTGTAGATAACTACGATACGGGA

GGGCTTACCATCTGGCCCCAGTGCTGCAATGATACCGCGAGACCCACGCTCAC

CGGCTCCAGATTTATCAGCAATAAACCAGCCAGCCGGAAGGGCCGAGCGCAG

AAGTGGTCCTGCAACTTTATCCGCCTCCATCCAGTCTATTAATTGTTGCCGGGA

AGCTAGAGTAAGTAGTTCGCCAGTTAATAGTTTGCGCAACGTTGTTGCCATTGC

TACAGGCATCGTGGTGTCACGCTCGTCGTTTGGTATGGCTTCATTCAGCTCCGG

TTCCCAACGATCAAGGCGAGTTACATGATCCCCCATGTTGTGCAAAAAAGCGG

TTAGCTCCTTCGGTCCTCCGATCGTTGTCAGAAGTAAGTTGGCCGCAGTGTTAT

CACTCATGGTTATGGCAGCACTGCATAATTCTCTTACTGTCATGCCATCCGTAA

GATGCTTTTCTGTGACTGGTGAGTACTCAACCAAGTCATTCTGAGAATAGTGTA

TGCGGCGACCGAGTTGCTCTTGCCCGGCGTCAATACGGGATAATACCGCGCCA

CATAGCAGAACTTTAAAAGTGCTCATCATTGGAAAACGTTCTTCGGGGCGAAA

ACTCTCAAGGATCTTACCGCTGTTGAGATCCAGTTCGATGTAACCCACTCGTGC

ACCCAACTGATCTTCAGCATCTTTTACTTTCACCAGCGTTTCTGGGTGAGCAAA

AACAGGAAGGCAAAATGCCGCAAAAAAGGGAATAAGGGCGACACGGAAATG

TTGAATACTCATACTCTTCCTTTTTCAATATTATTGAAGCATTTATCAGGGTTATT

GTCTCATGAGCGGATACATATTTGAATGTATTTAGAAAAATAAACAAATAGGGG

TTCCGCGCACATTTCCCCGAAAAGTGCCACCTGACGTCGACGGATCGGGAGAT

CGATCTCCCGATCCCCTAGGGTCGACTCTCAGTACAATCTGCTCTGATGCCGCA

TAGTTAAGCCAGTATCTGCTCCCTGCTTGTGTGTTGGAGGTCGCTGAGTAGTGC

GCGAGCAAAATTTAAGCTACAACAAGGCAAGGCTTGACCGACAATTGCATGA

AGAATCTGCTTAGGGTTAGGCGTTTTGCGCTGCTTCGCGATGTACGGGCCAGA

TATACGCGTTGACATTGATTATTGACTAGTTATTAATAGTAATCAATTACGGGGT

CATTAGTTCATAGCCCATATATGGAGTTCCGCGTTACATAACTTACGGTAAATGG

CCCGCCTGGCTGACCGCCCAACGACCCCCGCCCATTGACGTCAATAATGACGT

ATGTTCCCATAGTAACGCCAATAGGGACTTTCCATTGACGTCAATGGGTGGAGT

ATTTACGGTAAACTGCCCACTTGGCAGTACATCAAGTGTATC.
```

Figure 6B:
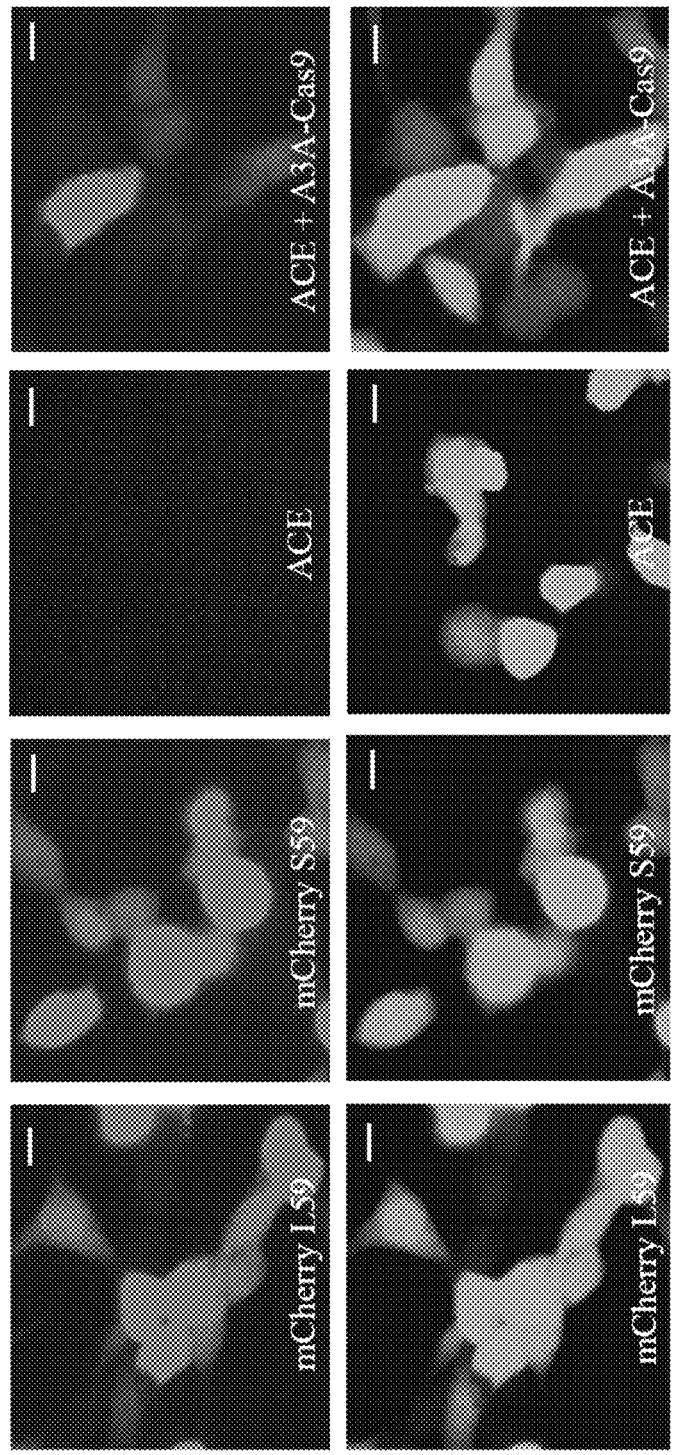

The ACE system was derived from HIV-1 NL4-3 by excising the gag-pol, vif, and vpr open reading frames using SwaI and SalI restriction sites and blunt end ligation. vpr and the first ~1,200 bp of env were removed using SacI and PsiI restriction sites and blunt end ligation to retain the Rev response element (RRE). A gBlock, synthesized by Integrated DNA Technologies (IDT) to introduce a CMV promoter with a 3' AgeI restriction site, was cloned into the nef open reading frame using BamHI and KpnI restriction sites. mCherry was PCR amplified using Phusion high-fidelity DNA polymerase (NEB) from a pcDNA3.1 expression plasmid with primers that introduced a 3' T2A self-cleaving peptide sequence (primer sequences provided in TABLE 1) and cloned into a CloneJET PCR cloning vector (Thermo Fisher). eGFP was PCR amplified from a pcDNA3.1 expression plasmid with primers (TABLE 1) introducing scrambled nucleotide sequences at the 5' and 3' ends of the gene that retained the wild-type protein sequence. This was done to eliminate recombination during reverse-transcription of the viral reporter because the 5' and 3' ~20 nt of mCherry and eGFP are identical. The eGFP PCR amplicon was cloned into the mCherry-T2A cloning vector using XhoI and KpnI restriction sites. Finally, the single mCherry-T2A-eGFP open reading frame was cloned into the modified NL4-3 vector using AgeI and KpnI restriction sites. Eight different mCherry mutants were created using site-directed mutagenesis with Phusion DNA polymerase (NEB) (primers in TABLE 1). Functional testing of several candidate mCherry L59S mutants identified one that reverted to mCherry positive with BE3. Subsequent DNA sequencing revealed a near triplication of the site-directed mutation oligonucleotide sequence, equating to a net insertion of 43 bp, likely created during PCR amplification step of the construction. The full sequence of this region is shown in FIG. 1C (SEQ ID NO:62), which includes two flanking gRNA binding sites that each contain an APOBEC-preferred 5'-TCA deamination target. For comparison, another round of site-directed mutagenesis generated a sequence-confirmed L59S mCherry single amino acid substitution mutant, which retained wild-type mCherry fluorescence activity (FIGS. 6A and 6B).

eGFP-based base editing reporters were generated by replacing wild-type eGFP with mutant eGFP PCR products. Mutant eGFP fragments were made by high-fidelity PCR with Phusion DNA polymerase (NEB) using primers listed in TABLE 1. Overlapping extension PCR was used to combine mutant eGFP fragments and add terminal restriction sites (5' XhoI and 3' KpnI). PCR products were digested with XhoI and KpnI and ligated into similarly cut parental vector. The resulting L202, L138, and Y93 single base editing reporters were confirmed by diagnostic restriction digestions and Sanger sequencing. eGFP reporter constructs were in a lentiviral backbone, and contained a bicistronic cassette in which a CMV promoter drove expression of mCherry and eGFP, separated by a self-cleavable peptide, T2A.

The A3B, A3C, A3D, A3F, A3G, and A3H editosomes were constructed in the same manner as A3A and A3Bctd. The primers used to amplify each construct are listed in TABLE 1.

Episomal DNA Editing Experiments: Semi-confluent 293T, SSM2c, CHO, and COS-7 cells in a 6-well plate format were transfected with 200 ng gRNA, 400 ng ACE, and 600 ng of each base-editor [10 minutes, RT with 6 µl of TransIT-LT1 (Minis) and 200 µl of serum-free DMEM (Hyclone)]. Cells were harvested at indicated time points for editing quantification by flow cytometry.

Chromosomal DNA Editing Experiments: A semi-confluent 10 cm plate of 293T cells was transfected with 8 µg of an HIV-1 Gag-Pol packaging plasmid, 1.5 µg of a VSV-G expression plasmid, and 3 µg of the ACE lentiviral reporter plasmid. Virus was harvested 48 hours post-transfection, frozen at −80° C. for 8 hours, thawed, and used to transduce target cells (MOI=1). 48 hours post-transduction, 600 ng APOBEC-Cas9n-UGI editor and 250 ng of targeting or NS-gRNA were transfected into a semi-confluent 6-well plate of ACE-transduced cells. Cells were harvested 96 hours post-transfection and editing was quantified by flow-cytometry.

In a subset of experiments, mCherry-positive cells were recovered by FACS, converted to genomic DNA (Gentra Puregene), and subjected to high-fidelity PCR using Phusion (NEB) to amplify mCherry target sequences (primers in TABLE 1). PCR products were gel-purified (GeneJET Gel Extraction Kit, Thermo Fisher Scientific) and cloned into a sequencing plasmid (CloneJET PCR Cloning Kit, Thermo Fisher Scientific). Sanger sequencing was done in a 96-well format (Genewiz) using primers recommended with the CloneJET PCR Cloning Kit (TABLE 1).

To carry out FANCF editing enrichment experiments, semi-confluent 293T cells transduced with ACE were co-transfected with 600 ng of A3Bctd-Cas9n-UGI and 200 ng of gRNA targeting both mCherry and FANCF in a 6-well format. 72 hours post-transfection, cells were harvested and FACS was used to collect cells expressing mCherry. gDNA was harvested and a 452 bp fragment of FANCF was PCR amplified using nested primers shown in TABLE 1. A PstI-HF (New England Biolabs) digest was done, and products were fractionated on an agarose gel to quantify editing efficiencies.

Immunoblotting:

$1\times10^6$ cells were lysed directly into 2.5× Laemmli sample buffer, separated by a 4-20% gradient SDS-PAGE, and transferred to PVDF-FL membranes (Millipore). Membranes were blocked in 5% milk in PBS and incubated with primary antibody diluted in 5% milk in PBS supplemented with 0.1% Tween20. Secondary antibodies were diluted in 5% milk in PBS supplemented with 0.1% Tween20 and 0.01% SDS. Membranes were imaged with a LICOR Odyssey instrument. Primary antibodies used in these experiments were rabbit anti-Cas9 (Abcam ab204448) and mouse anti-HSP90 (BD Transduction Laboratories 610418). Secondary antibodies used were goat anti-rabbit IRdye 800CW (LICOR 827-08365) and goat anti-mouse Alexa Fluor 680 (Molecular Probes A-21057).

Example 2—Construction and Initial Validation of the ACE Reporter System

The APOBEC- and Cas9-mediated editing reporter (ACE) system utilizes a CMV driven dual fluorescence reporter cassette (mCherry-T2A-eGFP) to enable expression and quantification of real-time editing in living mammalian cells (APOBEC editosome schematic in FIG. 1A, and reporter schematic in FIG. 1C). To maximize versatility, an HIV-based proviral vector was selected as the backbone for the system, enabling its use as a transient multi-copy plasmid-based episomal editing reporter or as a stable single-copy chromosomal DNA editing reporter. The eGFP fluorescence marker was used to quantify reporter delivery to target cells. The most important aspect of the ACE system is tight "off-to-on" gain of function fluorescence activity in which mCherry mutational inactivation creates an APOBEC deamination hotspot 5'-TCA, and then APOBEC-catalyzed editing is able to restore mCherry function. It is noted, as discussed above, that the markers can be reversed, such that an inactivated eGFP mutant can serve as the editing reporter and a wild type mCherry marker can serve to quantify reporter delivery. Other markers also can be used.

Eight different APOBEC mutational hotspots in mCherry were tested, and most failed to completely ablate fluorescence, were not located an appropriate distance from a gRNA anchoring motif (PAM), and/or did not become substrates for editing. One mutant mCherry construct proved robust, however, with no background fluorescence and a strong mCherry-positive signal upon transient co-expression of an appropriate mCherry-directed gRNA and the rat APOBEC1 editosome BE3 (fluorescence microscopy images in FIG. 1D and quantification in FIG. 1E; construct schematic in FIG. 1C). DNA editing and restoration of mCherry fluorescence required codon 59 (#59) gRNA-mediated targeting of the APOBEC-Cas9 complex to the intended hotspot because a non-specific (NS) gRNA did not restore fluorescence activity (fluorescence microscopy images in FIG. 1D and quantification in FIG. 1E). This system is portable and capable of providing real-time readouts of editing activity in a variety of different mammalian cell lines (e.g., 293T cells as shown in FIGS. 1D and 1E; COS-7, CHO, and SSM2c cells as shown in FIGS. 7A and 7B).

Surprisingly, DNA sequencing showed that the site-directed mutagenesis procedure used to generate the reporter had created a 43 bp insertion within mCherry, which shifted it out of frame for translation. The net result was generation of two codon 59 gRNA binding sites, each with an APOBEC-preferred editing hotspot 5'-TCA (the intervening region is also a potential gRNA binding site but it lacks a Cas9 PAM motif; FIG. 1C). Combining the aforementioned genetic requirements and sequence results of positive editing events (detailed below), the most likely molecular mechanism for reversion from mCherry negative to positive was simultaneous APOBEC-mediated editing of codon 59 5'-TCA hotspots to 5'-TUA (and/or flanking C's to U's) followed by cleavage of this DNA strand by the concerted action of canonical base excision repair enzymes (uracil excision by UNG2 and DNA cleavage by APE1), cleavage of the opposing DNA strand by the nickase activity of Cas9n, and repair of the resulting double-stranded breaks by non-homologous end joining (NHEJ) (outcome depicted in FIG. 1C). Activation of the ACE reporter required restoration of the full mCherry open reading frame, which at the structural level was due to fluorescence emission from a canonical β-barrel structure (FIG. 1C). An additional notable feature of the ACE reporter, and a likely additional explanation for why most constructs initially tested negative, is the structural location of mCherry residue 59 (the residue encoded by APOBEC hotspot) within a flexible loop region, which is more tolerant of amino acid substitution and flanking mutations including small insertions and deletions (e.g., a single L59S amino acid substitution retained wild-type mCherry activity; FIGS. 6A and 6B).

Figure 2A:
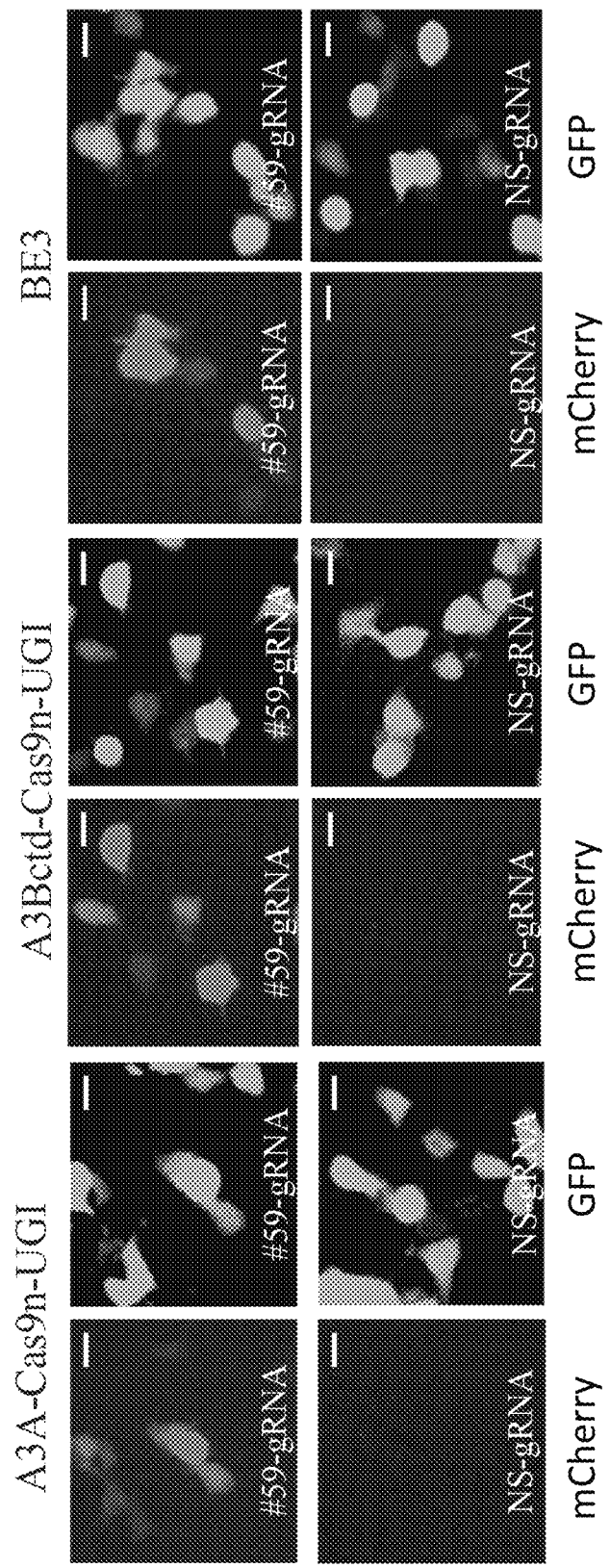
FIGS. 2A-2D show high-efficiency editing by human APOBEC3A (A3A) and human APOBEC3B C-terminal domain (A3Bctd) editosomes.
Figure 2B:
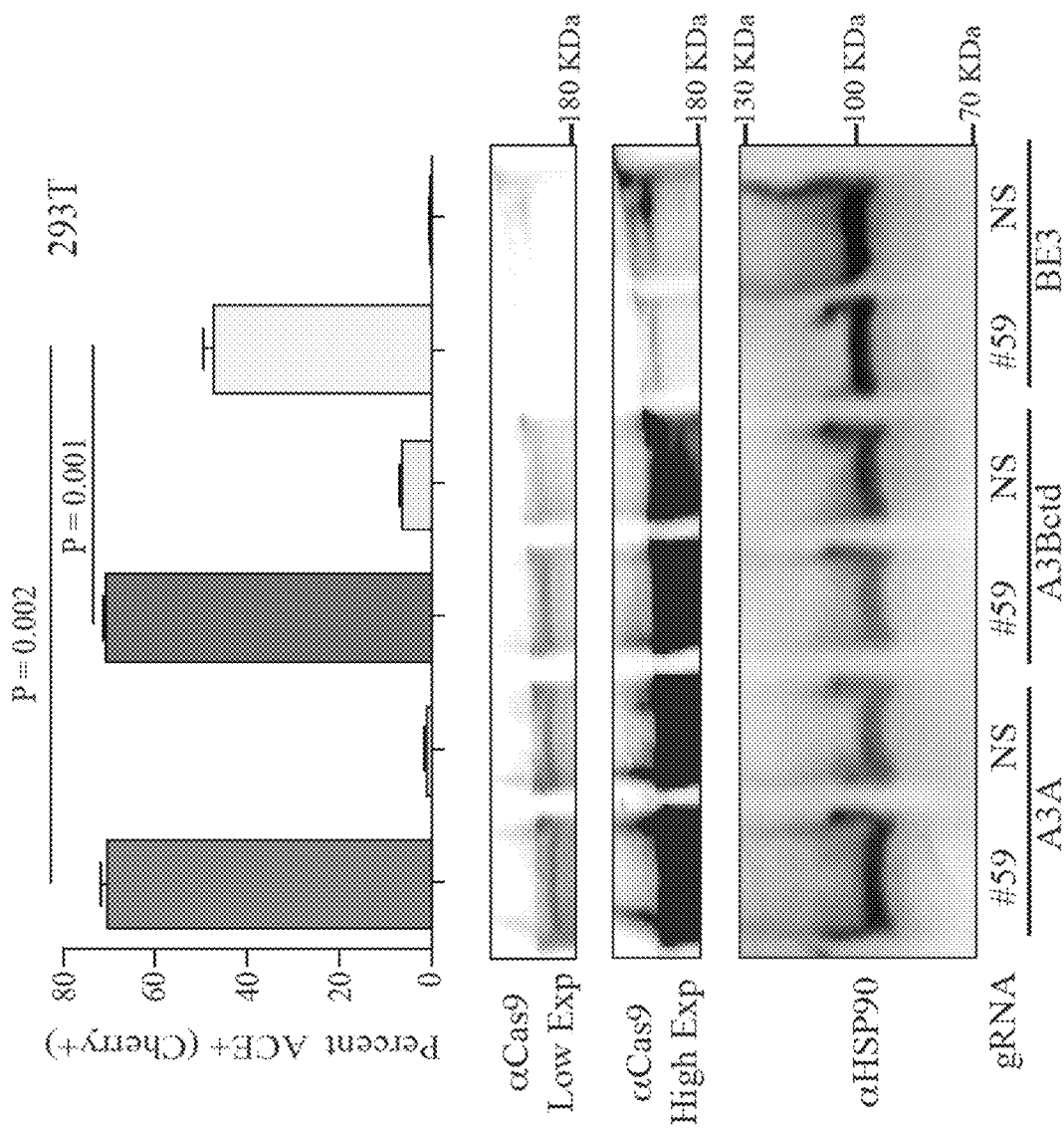
Figure 2C:
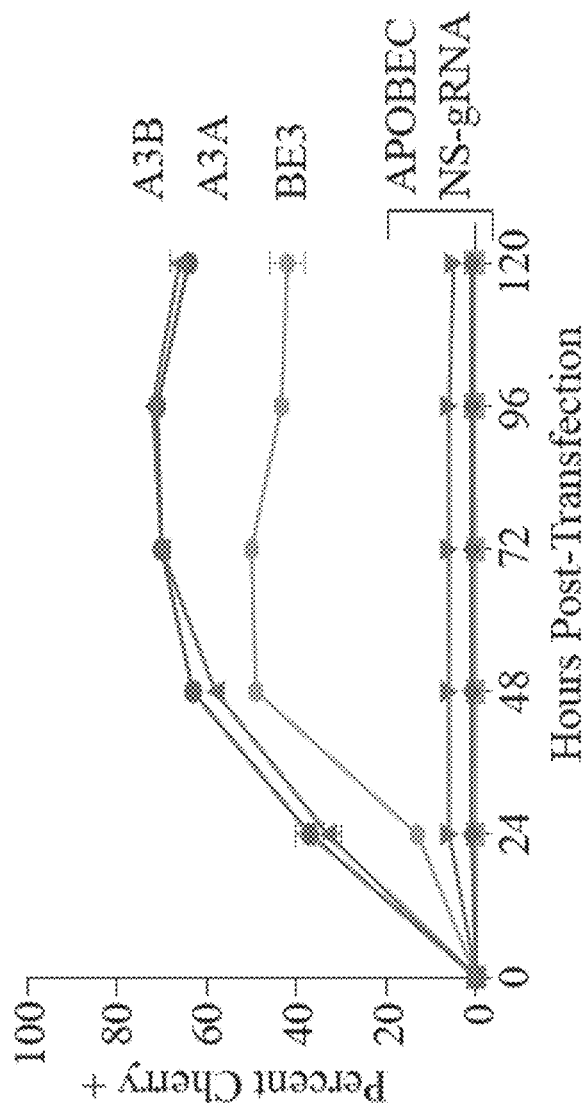
Figure 2D:
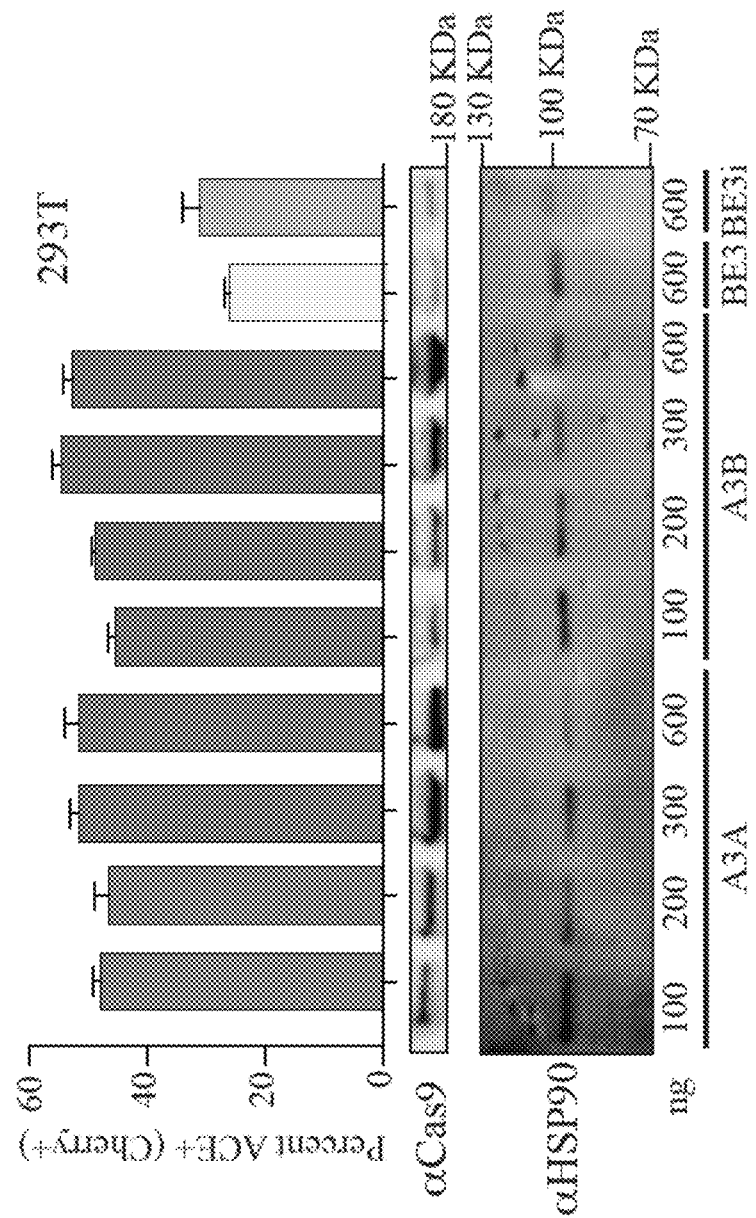

Example 3—Application of the ACE System to Create Highly Efficient Next-Generation Base Editing Constructs Based on Human APOBEC3A and APOBEC3B APOBEC3A (A3A) and APOBEC3B (A3B) are the most efficient ssDNA C-to-U deaminases in human cells (Stenglein et al., supra; Carpenter et al., supra; Burns et al., supra; and Ito et al., supra), and high-resolution crystal structures of both apo- and ssDNA-bound forms have been determined (Bohn et al., supra; Shi et al. 2015, supra; Shi et al. 2017, supra; and Kouno, supra). The catalytic domains of A3A and A3B therefore were tested for Cas9n-directed DNA editing. A3A-Cas9n-UGI and A3Bctd-Cas9n-UGI constructs were assembled and tested in parallel with BE3 to directly compare editing efficiencies. These constructs were co-transfected into 293T cells with ACE and a gRNA to direct editosomes to the insertion at mCherry codon 59 (#59) or a NS-gRNA (NS) as a negative control. In a single time point experiment, the rat APOBEC1 editosome yielded 47% mCherry-positive cells, and both A3A and A3Bctd achieved 70% mCherry-positive cells (representative fluorescence images in FIG. 2A and quantification in FIG. 2B). DNA deaminase activity was required, as catalytic glutamate mutant constructs, A3A-E72A and A3Bctd-E255A, were defective in ACE reporter activation (not shown). Higher editing efficiencies also were observed in time course studies in 293T cells, with both A3A and A3Bctd editosomes achieving nearly 40% mCherry fluorescence by 24 hours and maximal fluorescence of 70% by 72 hours before declining (as expected for transient transfection with non-replicating plasmids; FIG. 2C). Anti-Cas9 immunoblots indicated that at least some of the improved editing efficiencies might be due to higher expression levels of the A3A- and A3Bctd-Cas9n-UGI editosomes (FIG. 2B immunoblot images; FIG. 7B). A titration of A3A- and A3Bctd-Cas9n-UGI was performed to compare editing efficiencies of the newly developed editosomes to those of BE3 and, despite achieving similar expression levels (lanes 1, 5, and 9), the newly developed A3A- and A3Bctd-Cas9n-UGI editosomes still exhibited higher editing frequencies (FIG. 2D). In addition, an intron was cloned into BE3 (identical to that in the A3A and A3Bctd editosome constructs), and the newly created BE3 intron (BE3i) construct was tested against the ACE reporter to rule out intron-associated differences in protein expression (FIG. 2D). As for the original BE3, the intron-containing derivative still had expression and DNA editing levels lower than those of the A3A and A3Bctd editosomes.

Figure 3A:
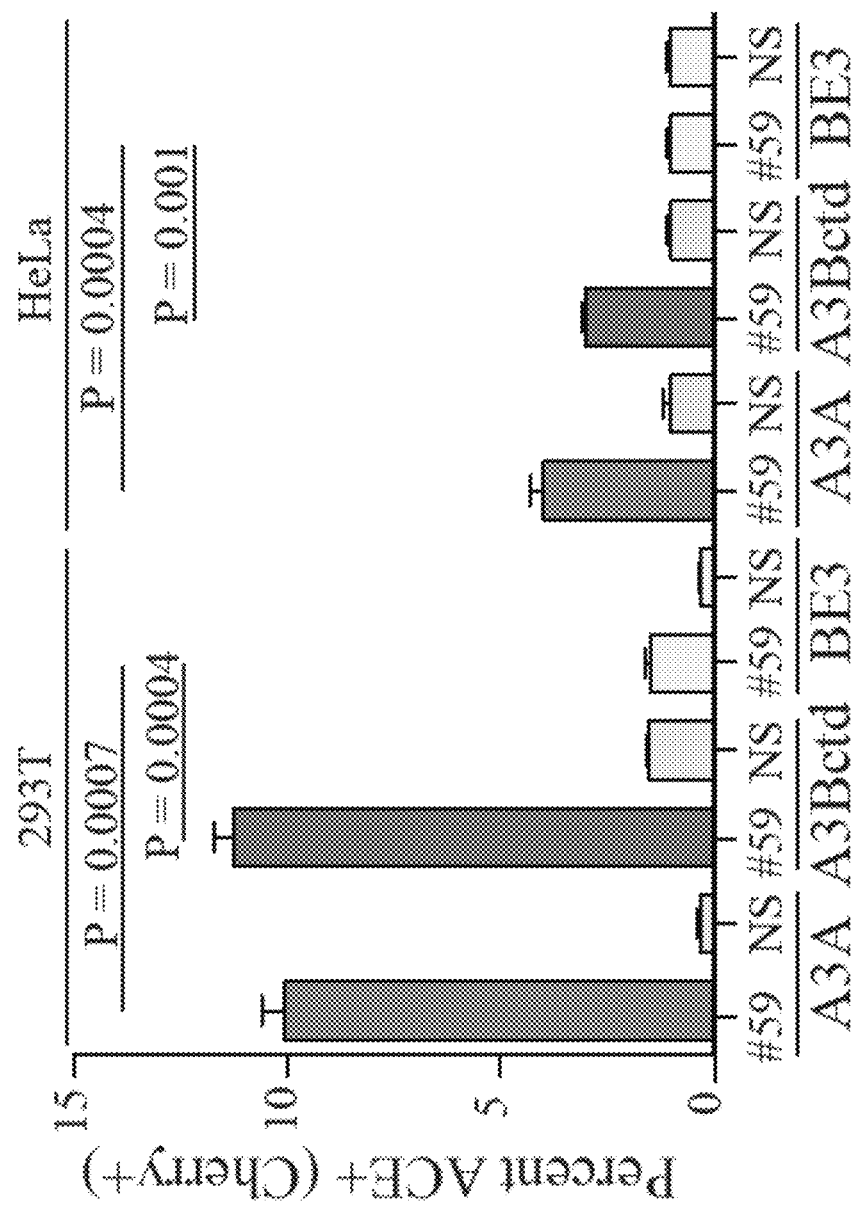
Figure 3B:
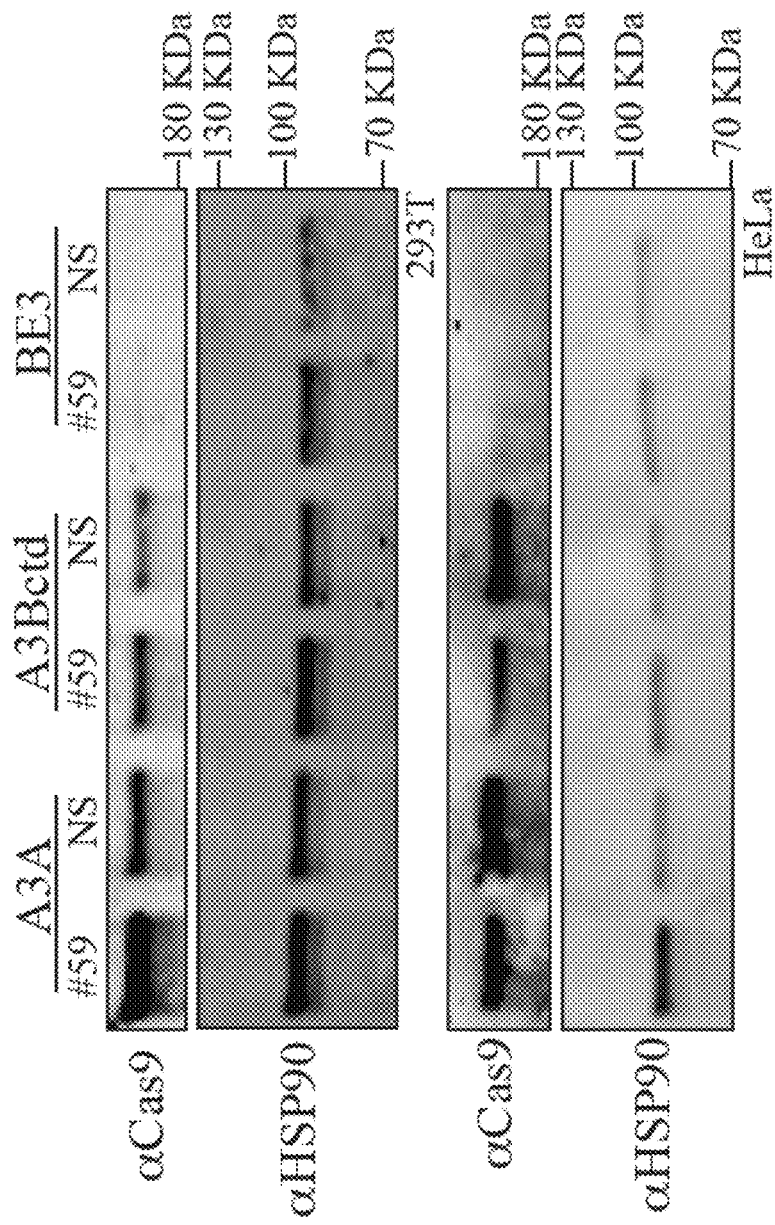

Example 4—Improved Chromosomal DNA Editing Efficiencies Using A3A and A3Bctd Editosomes To further compare the efficiencies of these editosomes, ACE was pre-delivered to 293T and HeLa cells by lentiviral transduction (MOI of 1). Following stable introduction of the reporter, the resulting mCherry-negative/eGFP-positive pools were co-transfected with editosome constructs and either a gRNA directed to the insertion at mCherry codon 59 or a NS-gRNA as a negative control. As above, the A3A and A3Bctd editosomes performed better than the rat APOBEC1 editosome (FIGS. 3A and 3B). However, the single copy nature of the ACE system in the context of the chromosome caused a 10-fold reduction in the overall efficiency of each editosome. This result was expected because reversion of a single copy chromosomal reporter, which is chromatinized to varying degrees depending on integration position, will occur less frequently than editing of one of many episomal copies in a transient co-transfection experiment.

Figure 3C:
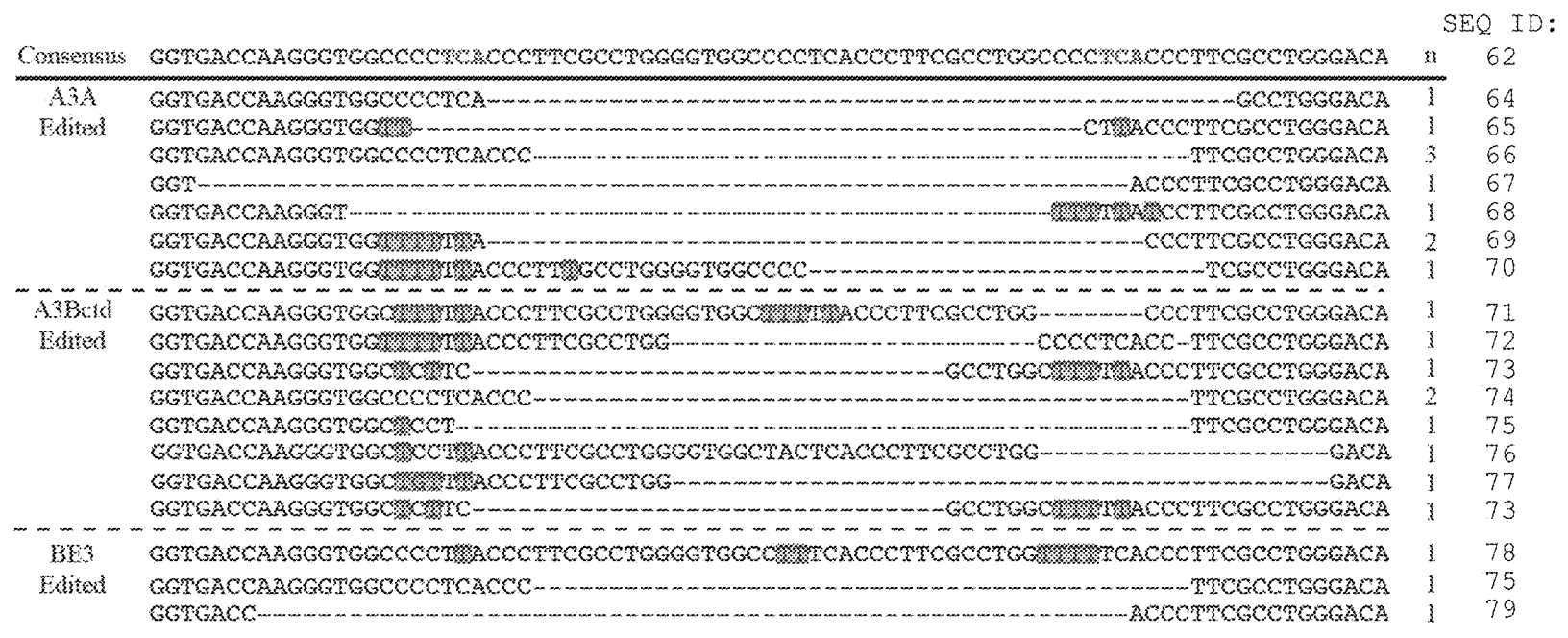

To further investigate the mechanism of ACE reporter activation, DNA sequencing was used to ask whether editing events catalyzed by APOBEC editosomes were specific to the intended 5'-TCA motifs or distributed more broadly within the ssDNA loops created by gRNA base pairing to the duplicated target region. FACS was used to enrich for mCherry-positive cells with chromosomal editing events, and single high-fidelity PCR amplicons were cloned into a plasmid vector for Sanger sequencing (FIG. 3C). As expected, almost all clones contained editing-associated deletions that caused mCherry to be shifted into the correct open reading frame, which was essential for fluorescence restoration. Interestingly, many of the sequences had C-to-T mutations in flanking regions displaced by annealing of the gRNA, but not in surrounding DNA regions that are presumably double-stranded and protected from the single-strand specific DNA deaminase activity of the APOBEC enzymes. Thus, in addition to enabling quantification of editing efficiencies in episomes and chromosomes, the ACE system unexpectedly reported both on-target and target-adjacent editing events. This may explain why several other tested sites in mCherry were not amenable to being developed into an editing reporter system.

Example 5—Canonical Cas9 DNA Cleavage Quantification Using the ACE Reporter

Figure 4:
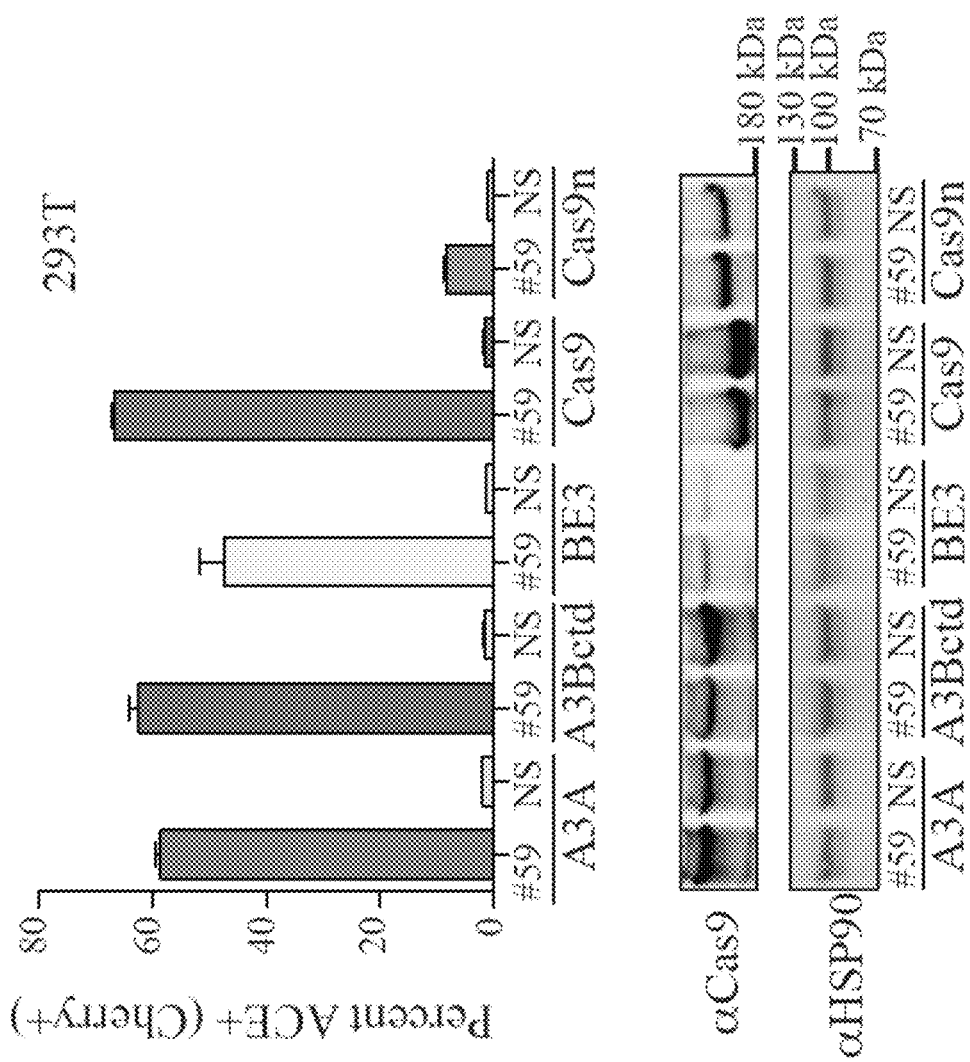
FIG. 4 shows ACE reporter activation through Cas9 nucleolytic cleavage. The top portion is a graph plotting the quantification of ACE reporter activation in 293T cells 72 hours after co-transfection of ACE reporter, mCherry codon 59 targeting gRNA or NS-gRNA, and A3A-Cas9n-UGI, A3Bctd-Cas9n-UGI, rat APOBEC1-Cas9n-UGI/BE3, Cas9, or Cas9n expression constructs (n=3; mean±SD). Anti-Cas9 and anti-HSP90 immunoblots from a representative experiment are shown below the graph.

The tight coupling of editing and deletion mutagenesis suggested that the ACE reporter is also capable of quantifying the double-stranded DNA cleavage activity of Cas9. Given the wide use of CRISPR/Cas9 in biology and medicine, a method to visualize its editing activity in real-time would be highly useful. To test this idea, the ACE system was simultaneously analyzed using the A3A and A3Bctd editosomes, BE3, and Cas9 nuclease constructs (FIG. 4). As described above, A3A and A3Bctd had editing levels higher than that of BE3. In addition, the Cas9 nuclease drove editing to levels comparable to A3A and A3Bctd editosomes, thus expanding the utility of the ACE reporter system. In comparison, a Cas9 nickase alone only elicited modest reporter activation.

Figure 5A:
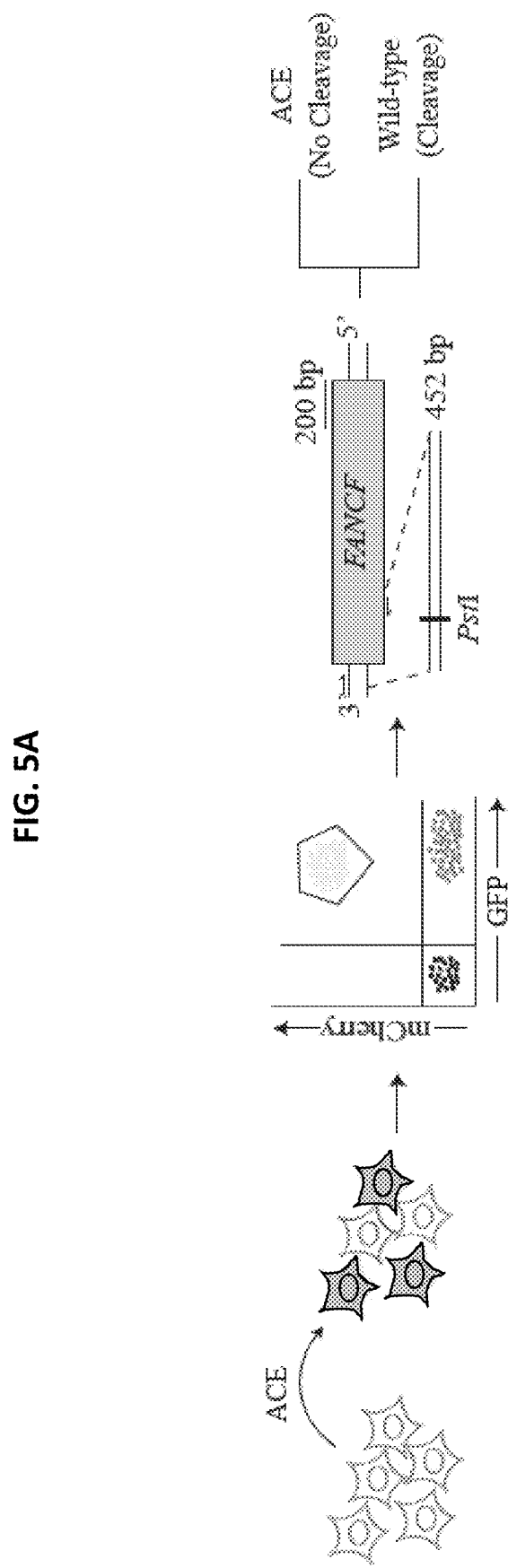
Figure 5B:
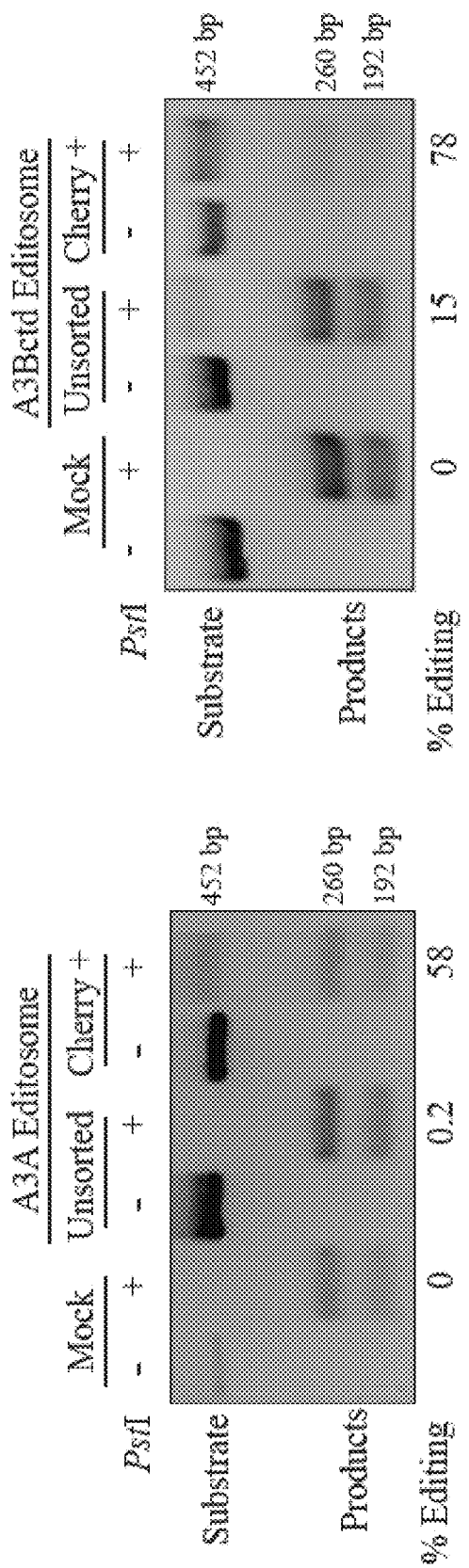

Example 6—Application of the ACE Reporter System to Enrich for Editing Events at Heterologous Chromosomal Sites Studies were then conducted to determine whether the ACE system could enrich for chromosomal DNA editing events at an unlinked genetic locus with disease relevance. ACE-transduced eGFP-positive 293T cells were transfected with A3A-, A3Bctd-, or rat APOBEC1-Cas9n-UGI base editing constructs and gRNAs targeting mCherry codon 59 and FANCF codon 5. After 96 hours of incubation, mCherry-positive (ACE-edited) cells were purified by FACS and editing events at FANCF were assessed using a PCR and restriction enzyme-based assay (FIG. 5A). Wild-type FANCF DNA amplicons were 452 bp in length, and restriction by PstI (5'-CTGCAG) resulted in fragments of 192 and 260 bp that were visible by agarose gel electrophoresis. APOBEC-mediated editing would potentially destroy the PstI cleavage site and preserve the full-length fragment. The A3A and A3Bctd reactions yielded >10,000 mCherry-positive cells for this analysis, while the rat APOBEC1 editosome yielded too few fluorescent cells for reliable purification (concordant with low frequency chromosomal editing data shown in FIGS. 3A and 3B). Nevertheless, the restriction assay yielded clear results, with FANCF editing events being highly enriched in sorted mCherry-positive cells in comparison to unsorted pools (FIG. 5B; 290-fold and 5-fold for A3A and A3Bctd editosomes, respectively). Sequencing data showed that ACE-sorted cells were edited at the FANCF locus, and nearly all edited sequences had mutations in the PstI cut site (FIG. 5C). These data indicated that the ACE reporter system can be broadly useful for isolating subpopulations of cells with heterologous chromosomal editing events.

Example 7—Single Base Editing of eGFP

Figure 8A:
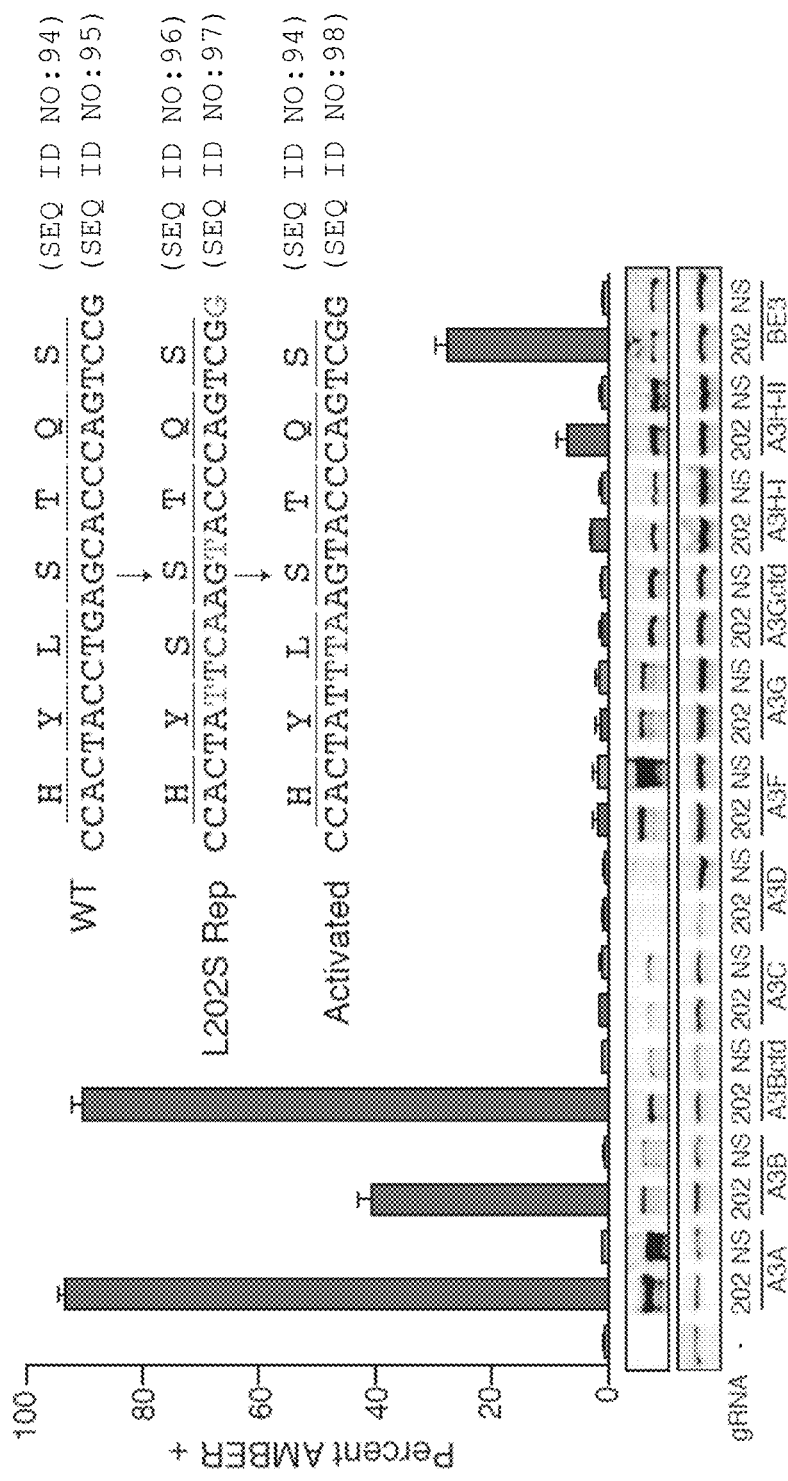
FIGS. 8A-8F show AMBER results for eGFP codons 202, 138, and 93 in transient transfection experiments. Quantification of transient transfection experiments for the indicated APOBEC panel of base-editors, appropriate gRNAs, and the eGFP codon 202 reporter (FIG. 8A, with representative images in FIG. 8B), codon 138 reporter (FIG. 8C, with representative images in FIG. 8D), and codon 93 reporter (FIG. 8E, with representative images in FIG. 8F). A non-specific (NS) gRNA was used as a negative control (n=3; average±SD). Immunoblots for Cas9 and HSP90 are shown below each histogram.
Figure 8B:
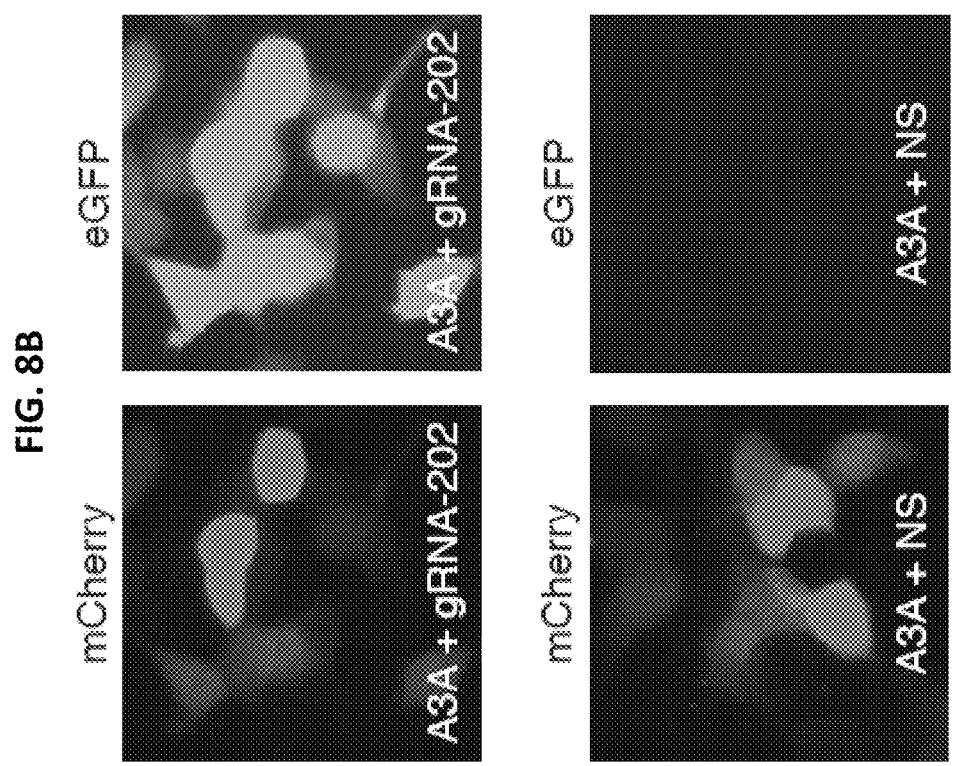
Figure 8C:
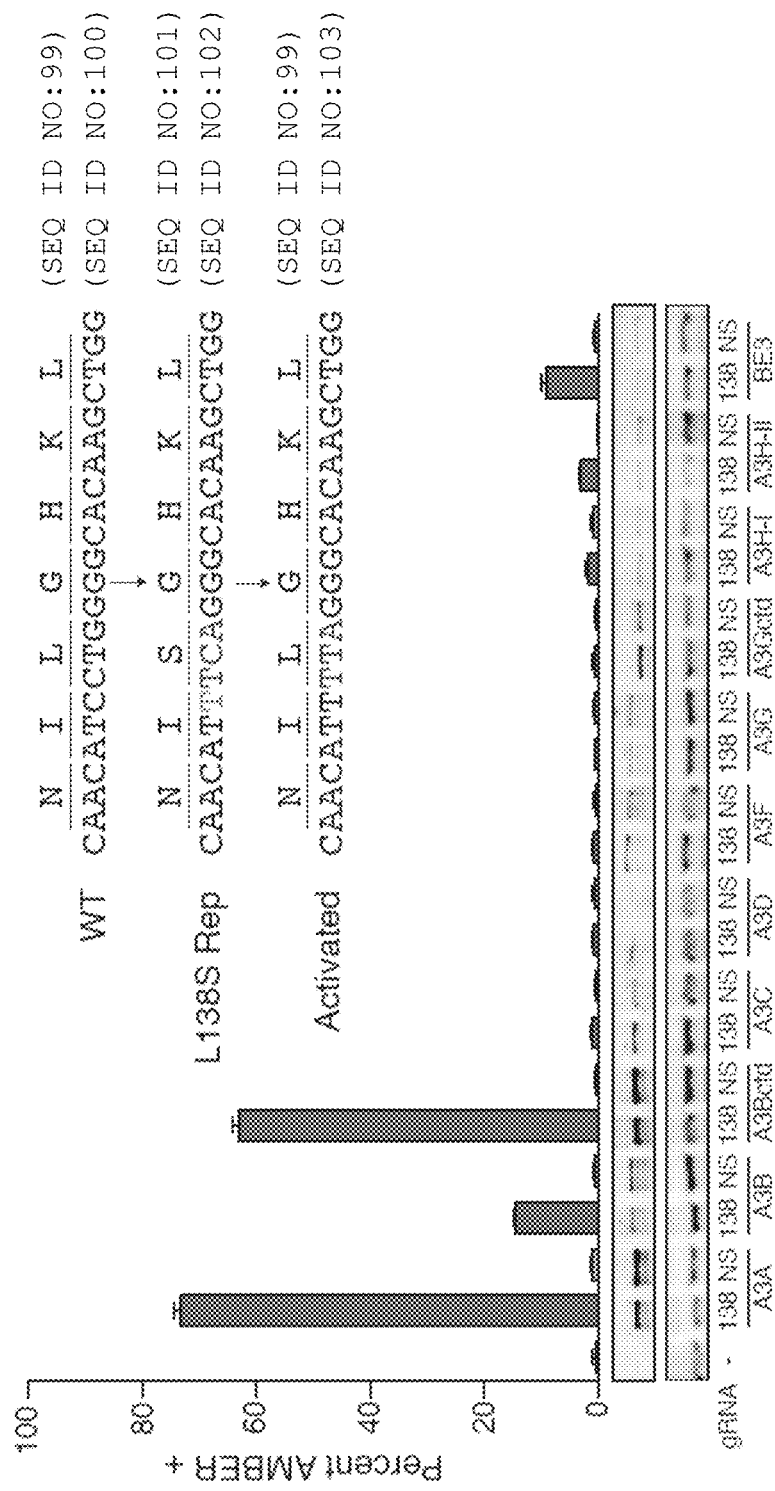
Figure 8D:
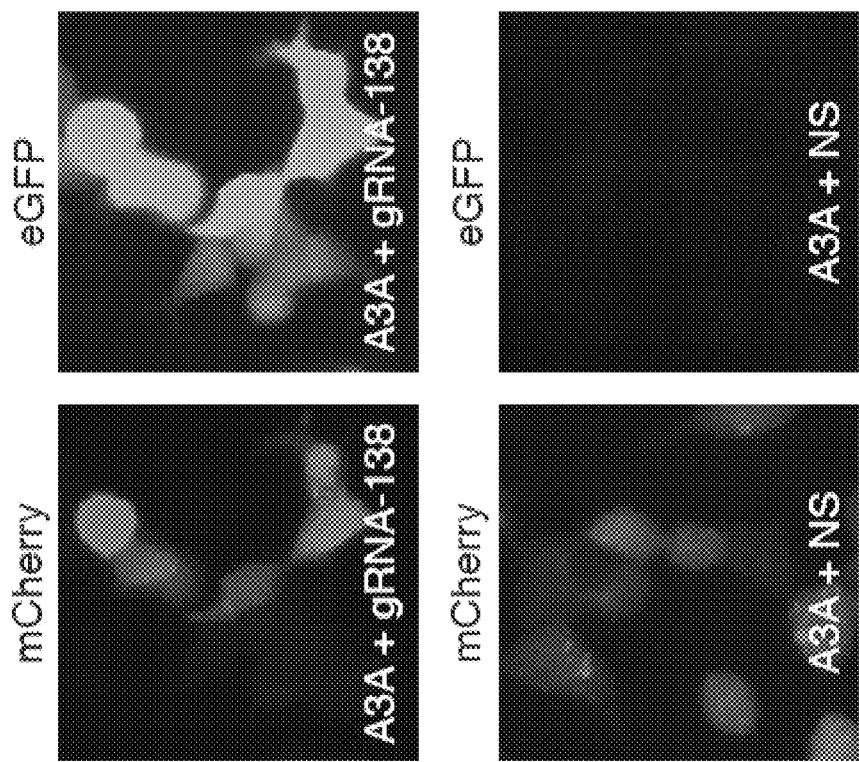
Figure 8E:
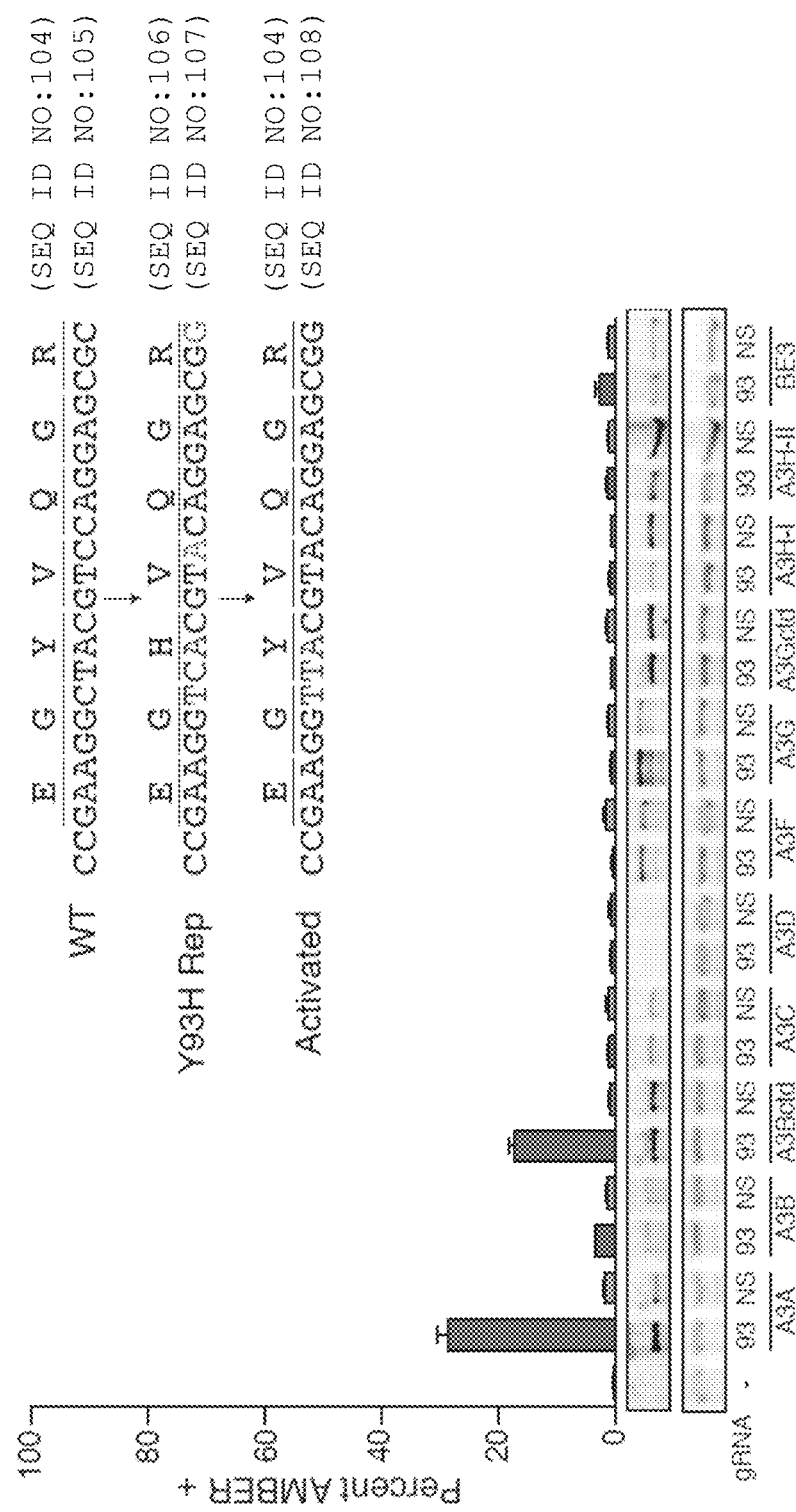
Figure 8F:
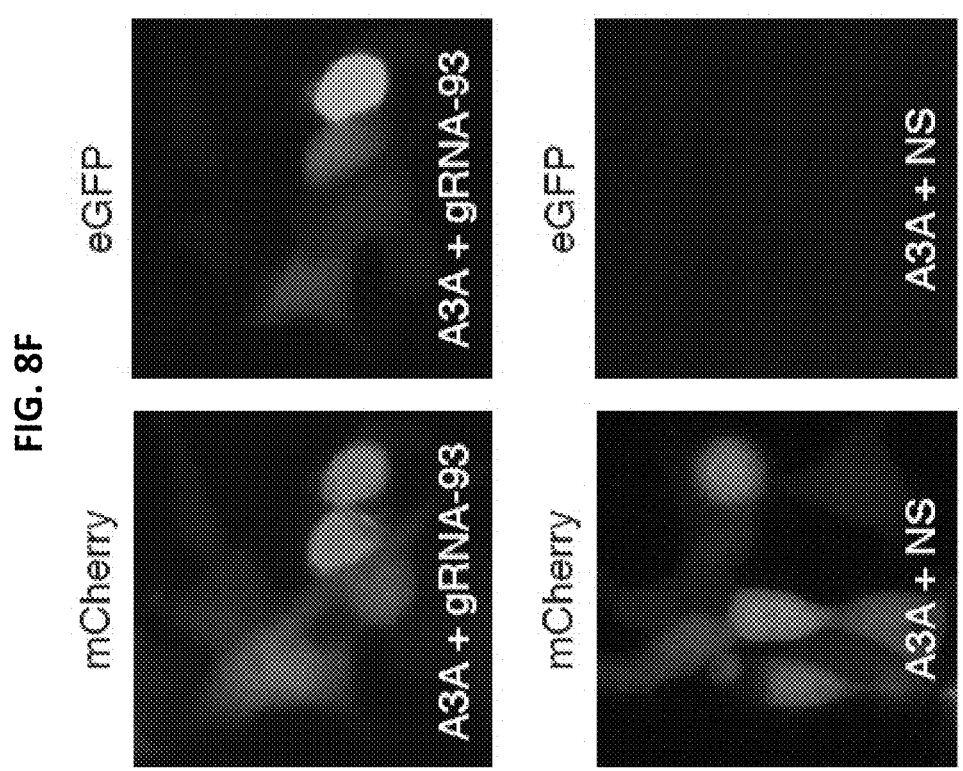

In addition, a panel of AMBER (APOBEC-mediated base editing reporter) constructs was developed in which a single on-target C-to-T editing event would restore eGFP fluorescence and enable real-time quantification of DNA editing. Three codons in eGFP were identified where a T-to-C mutation would ablate fluorescence and simultaneously create a potential APOBEC editing site (L202, L138, and Y93; inset in FIGS. 8A, 8C, and 8E, respectively). One or more silent mutations were purposely introduced alongside these specific changes in order to reduce the number of nearby editing sites, decrease the likelihood of DSBs, and optimize the PAM required for gRNA recognition. In particular, eGFP leucine to serine mutations were created by changing 5'-CTG to 5'-TCA at the indicated positions. When edited by an APOBEC, these mutations reverted to a 5'-TTA, thus reverting the amino acid from a serine back to a leucine. eGFP tyrosine to histidine mutations were created by mutating a wobble base upstream to a thymine and the 5'-TAC to a 5'-CAC. When edited by an APOBEC, this reverted to a 5'-TAC, restoring the tyrosine residue and fluorescence. Each inactivated eGFP editing reporter was positioned downstream of a wild-type mCherry gene that functioned as a marker for assessing transfection and transduction efficiencies. Single base editing efficiencies were therefore quantified by dividing the fraction of eGFP-positive cells by the fraction of mCherry-positive cells.

Reporter utility was first tested by comparing efficiencies of single base editing in transiently transfected 293T cells by the BE3 editosome (Komor et al., supra), APOBEC3A and APOBEC3B C-terminal catalytic domain(ctd)-Cas9n-UGI complexes as described herein, as well as editosome constructs for APOBEC3B (full-length), APOBEC3C, APOBEC3D, APOBEC3F, APOBEC3G, and two naturally occurring variants of APOBEC3H (haplotype I and II). This panel therefore included the entire seven enzyme human APOBEC3 repertoire. For each editosome complex, efficiencies were highest for the L202 reporter, lower for the L138 reporter, and lowest for the Y93 reporter (FIGS. 8A-8B, 8C-8D, and 8E-8F, respectively). Moreover, within a given reporter data set, APOBEC3A and APOBEC3Bctd editosomes showed the highest activity, followed by APOBEC3B (full-length), rat APOBEC1, and APOBEC3H-II. All other editosomes showed negligible activity, which may have been due in part on poor expression (APOBEC3D), different dinucleotide preference (APOBEC3G), or other reasons. DNA sequencing was not used to analyze these editing events due to vast excesses of non-edited reporter plasmids in each transient transfection reaction.

Next, chromosomal DNA editing efficiencies were compared by transiently cotransfecting each editosome construct and appropriate eGFP gRNA into 293T cell pools pre-engineered to contain a single copy of each editing reporter by lentivirus-mediated transduction and mCherry FACS enrichment. For each editosome, overall editing efficiencies were lower than those for transiently transfected reporters, likely due to fewer editing substrates per cell (i.e., many vs one). However, relative editing and reporter efficiencies were still similar, with APOBEC3A/APOBECBctd editing more efficiently than full-length A3B, BE3, and APOBEC3H-II, and the L202 reporter performing better than the L138 and Y93 reporters (FIGS. 9A and 9B). In fact, the Y93 data are not included because eGFP fluorescence rarely rose above background.

DNA sequencing was then used to analyze on-target editing events. Sanger sequences of individually cloned PCR products showed 2/6 on-target L202 editing events for APOBEC3A editosomes and 8/9 for APOBEC3Bctd editosomes (FIG. 9C). Similar results were obtained for L138 editing events, with 9/14 on-target for APOBEC3A and 13/16 for APOBEC3B editosomes. Both of these editing complexes also caused a proportion of off-target events upstream of the intended target cytosine (FIG. 9C). APOBEC3A also caused a low frequency of downstream off-target events (not shown). As expected, the highest frequencies of off-target events occurred within the 5'-end of the single-stranded DNA loop caused by gRNA annealing, but additional editing events, sometimes coordinated and on both DNA strands, also occurred further upstream suggesting a tendency for these two eGFP regions to become single-stranded.

In summary, this document provides novel, fluorescence-based APOBEC-mediated based editing reporters that yield rapid, efficient, and quantitative read-outs of base editing activity in living mammalian cells. These reporter systems enable comparison of DNA editing efficiencies in two different subcellular contexts—episomal high-copy conditions and chromosomal single-copy conditions. It is noted that these systems can be adapted to other mammalian and non-mammalian cell types for a wide variety of applications, such as enrichment for heterologous editing events in reporter-activated cells, and thereby may reach near-universal status along with Cas9. For example, transient transfection of ACE and an appropriate editosome into mammalian cells, along with gRNAs targeting mCherry codon 59 and a genomic site of interest, can enable rapid enrichment of editing competent cells by FACS. As shown herein for FANCF, transduction of the ACE reporter and subsequent transfection of an APOBEC editosome, along with gRNAs targeting mCherry codon 59 and FANCF, enabled FACS enrichment of mCherry-positive cells and enrichments for FANCF editing events. Similarly, the AMBER systems enable similar FACS-based enrichments as well as, importantly, quantitative single base editing in living cells. The ACE and AMBER live cell systems also can be useful for further applications, such as screening for modifiers of editing activity and for future engineering refinements, such as developing truly single-base specific editosomes and thus avoiding potentially detrimental off-target effects including DNA double-stranded breaks.

TABLE 1

Oligonucleotide sequences

| Primer | Sequence (5' to 3') | SEQ ID |
|---|---|---|
| A3A cloning forward primer | AGATCCGCGGCCGCGCCGCCACCATGATGGAAGCCAGCCCAGCATCCGGGC | 18 |
| A3A cloning reverse primer | TGAGGTCCCGGGAGTCTCGCTGCCGCTTCCGTTTCCCTGATTCTGGAGAATG | 19 |
| A3Bctd cloning forward primer | AGATCCGCGGCCGCGCCGCCACCATGGATCCAGACACATTCACTTTCAACT | 20 |
| A3Bctd cloning reverse primer | TGAGGTCCCGGGAGTCTCGCTGCCGCTGTTTCCCTGATTCTGGAGAATGGCC | 21 |
| mCherry L59S SDM forward primer | AAGGGTGGCCCCTCACCCTTCGCCTGGG | 22 |
| mCherry L59S SDM reverse primer | CCCAGGCGAAGGGTGAGGGGCCACCCTT | 23 |
| Codon #59-directed mCherry gRNA forward primer | ACACCTGGCCCCTCACCCTTCGCCTG | 24 |
| Codon #59-directed mCherry gRNA reverse primer | AAAACAGGCGAAGGGTGAGGGGCCAG | 25 |
| NS gRNA forward | ACACCGCACTACCAGAGCTAACTCAG | 26 |
| NS gRNA reverse | AAAACTGAGTTAGCTCTGGTAGTGCG | 27 |
| T2A cloning forward primer | CTGGCTACCGGTATGGTGAGCAAGGGCGAGG | 28 |
| T2A cloning reverse primer | TTAAAGGTACCAGGGCCGGGATTCTCCTCCACGTCACCGCATGTTAGAAGACTTCCTCTGCCCTCCTTGTACTCGAGATCTGCACCGGGCTTGTACAGCTCGTCCATGCC | 29 |
| eGFP cloning forward primer | GCAGATCTCGAGTACAAGGAGGGCAGAGGAAGTCTTCTAACATGCGGTGACGTGGAGGAGAATCCCGGCCCTCTGGTCAGTAAAGGTGAAGAACTGTTCACCG | 30 |
| eGFP cloning reverse primer | CTTAAAGGTACCTTATTTATATAATTCATCCATACCGAGAG | 31 |
| mCherry Amplification Forward Primer | ATGGCCATCATCAAGGAGTT | 32 |
| mCherry Amplification Reverse Primer | CTCTGCCCTCCTTGTACTCG | 33 |
| CloneJET Sequencing Forward Primer | CGACTCACTATAGGGAGAGCGGC | 34 |
| CloneJET Sequencing Reverse Primer | AAGAACATCGATTTTCCATGGCAG | 35 |
| L1 Intron into BE3 Forward | NNNGAGCTCAGAGACTGGCCCAGTGGCTGTGGACCCCACATTGAGGTGAGTCCAGGAGA | 36 |
| L1 Intron into BE3 Reverse | NNNGAGCTCTCTCGGATCGAAGAATACCTCAAACTCATGGGGCTCGATCCGCCGTCTGT | 37 |
| Y93H Mutation Forward | CCATGCCCGAAGGTCACGTACAGGAGCGGACCATCTTC | 38 |
| Y93H Mutation Reverse | GAAGATGGTCCGCTCCTGTACGTGACCTTCGGGCATGG | 39 |
| L138S Mutation Forward | GGACGGCAACATTTCAGGGCACAAGCTGGA | 40 |
| L138S Mutation Reverse | TCCAGCTTGTGCCCTGAAATGTTGCCGTCC | 41 |

TABLE 1-continued

Oligonucleotide sequences

| Primer | Sequence (5' to 3') | SEQ ID |
|---|---|---|
| L202S Mutation Forward | CGACAACCACTATTCAAGTACCCAGTCGGCCCTGA | 42 |
| L202S Mutation Reverse | TCAGGGCCGACTGGGTACTTGAATAGTGGTTGTCG | 43 |
| Full-length A3Bi cloning primer forward | AGATCCGCGGCCGCGCCGCCACCATGAATCCACAGATCAGAAATCCGATGG | 44 |
| Full-length A3Bi cloning primer reverse | TGAGGTCCCGGGAGTCTCGCTGCCGCTGTTTCCCTGATTCTGGAGAATGGCC | 45 |
| A3C cloning primer forward | AGATCCGCGGCCGCGCCGCCACCATGAATCCACAGATCAGAAACCCGATGA | 46 |
| A3C cloning primer reverse | TGAGGTCCCGGGAGTCTCGCTGCCGCTCTGGAGACTCTCCCGTAGCCTTCTT | 47 |
| A3D cloning primer forward | AGATCCGCGGCCGCGCCGCCACCATGAATCCACAGATCAGAAATCCGATGG | 48 |
| A3D cloning primer reverse | TGAGGTCCCGGGAGTCTCGCTGCCGCTCTGGAGAATCTCCCGTAGCCTTCTT | 49 |
| A3F cloning primer forward | AGATCCGCGGCCGCGCCGCCACCATGAAGCCTCACTTCAGAAACACAGTGG | 50 |
| A3F cloning primer reverse | TGAGGTCCCGGGAGTCTCGCTGCCGCTCTCGAGAATCTCCTGCAGCTTGCTG | 51 |
| A3G cloning primer forward | AGATCCGCGGCCGCGCCGCCACCATGAAGCCTCACTTCAGAAACACAGTGG | 52 |
| A3G cloning primer reverse | TGAGGTCCCGGGAGTCTCGCTGCCGCTGTTTTCCTGATTCTGGAGAATGGCC | 53 |
| A3H-I and A3H-II cloning primer forward | AGATCCGCGGCCGCGCCGCCACCATGGCTCTGTTAACAGCCGAAACATTCCG | 54 |
| A3H-i and A3H-II cloning primer reverse | TGAGGTCCCGGGAGTCTCGCTGCCGCTTCAGGACTGCTTTATCCTGTCAAGC | 55 |
| GFP Y93H gRNA forward | ACACCCCGAAGGTCACGTACAGGAG | 56 |
| GFP Y93H gRNA reverse | AAAACCTCCTGTACGTGACCTTCGGG | 57 |
| GFP L138S gRNA forward | ACACCCAACATTTCAGGGCACAAGCG | 58 |
| GFP L138S gRNA reverse | AAAACGCTTGTGCCCTGAAATGTTGG | 59 |
| GFP L202S gRNA forward | ACACCCCACTATTCAAGTACCCAGTG | 60 |
| GFP L202S gRNA reverse | AAAACACTGGGTACTTGAATAGTGGG | 61 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A nucleic acid comprising:

a first nucleotide sequence encoding a first reporter, wherein the first reporter is inactivated by a revertible mutation within the nucleotide sequence encoding the first reporter, as compared to a reference sequence for the first reporter, wherein the mutation is a T to C point mutation that can be reverted by a base editing complex, and wherein the revertible mutation is about 5 to 20 bp from a Cas protospacer adjacent motif (PAM); and a second nucleotide sequence encoding a second reporter that is active when it is expressed, wherein the first and second nucleotide sequences are operably linked to one or more promoters that drive expression of the first and second nucleotide sequences, and wherein the first and second nucleotide sequences are separated by a nucleotide sequence encoding a self-cleaving peptide.

2. The nucleic acid of claim 1, wherein the first and second reporters are fluorescent reporter polypeptides.

3. The nucleic acid of claim 1, wherein the first reporter or the second reporter is a mCherry polypeptide.

4. The nucleic acid of claim 3, wherein the first reporter is a mCherry polypeptide comprising the amino acid sequence set forth in SEQ ID NO:2, with the proviso that the leucine residue at position 56 of SEQ ID NO:2 is replaced with a serine residue.

5. The nucleic acid of claim 4, wherein the serine residue is encoded by a TCA codon.

6. The nucleic acid of claim 3, wherein the second reporter is a mCherry polypeptide comprising the amino acid sequence set forth in SEQ ID NO:2.

7. The nucleic acid of claim 1, wherein the first or second reporter is a green fluorescent protein (GFP) polypeptide.

8. The nucleic acid of claim 7, wherein the GFP polypeptide is an enhanced GFP (eGFP) polypeptide.

9. The nucleic acid of claim 7, wherein the first reporter is an eGFP polypeptide comprising the amino acid sequence set forth in SEQ ID NO:4, with the proviso that the leucine residue at position 202 of SEQ ID NO:4 is replaced with a serine residue, the leucine residue at position 138 of SEQ ID NO:4 is replaced by a serine residue, or the tyrosine at position 93 of SEQ ID NO:4 is replaced by a histidine residue.

10. The nucleic acid of claim 9, wherein the serine residue at position 202 or position 138 is encoded by a TCA codon, or wherein the histidine at position 93 is encoded by a CAC codon.

11. The nucleic acid of claim 7, wherein the second reporter is an eGFP polypeptide comprising the amino acid sequence set forth in SEQ ID NO:4.

12. The nucleic acid of claim 1, wherein the revertible mutation is a point mutation that can be reverted by a base editing complex comprising an apolipoprotein B mRNA-editing complex (APOBEC) polypeptide, or a portion thereof.

13. The nucleic acid of claim 12, wherein the APOBEC polypeptide is rat APOBEC1 or a portion thereof, human APOBEC3A or a portion thereof, human APOBEC3B or a portion thereof, or human APOBEC3H or a portion thereof.

14. The nucleic acid of claim 12, wherein the APOBEC polypeptide is a human APOBEC3B C-terminal domain.

15. The nucleic acid of claim 12, wherein the base editing complex comprises an APOBEC polypeptide, a Clustered Regularly Interspersed Short Palindromic Repeats (CRISPR)-associated-9 (Cas9) polypeptide, and a uracil DNA glycosylase inhibitor (UGI).

16. A vector comprising the nucleic acid of claim 1.

17. The nucleic acid of claim 2, wherein the first and second reporters are selected from the group consisting of Cyan Fluorescent Proteins, GFPs, Yellow Fluorescent Proteins, Orange Fluorescent Proteins, Red Fluorescent Proteins, Far-red fluorescent Proteins, and Switchable Fluorescent Proteins.

18. The nucleic acid of claim 17, wherein the first and second reporters are selected from the group consisting of AmCyanl, AcGFPl, ZsGreenl, ZsYellowl, mBanana, mOrange, mOrange2, DsRed-Express2, DsRed-Express, tdTomato, DsRed-Monomer, DsRed2, AsRed2, mStrawberry, HcRedl, mRaspberry, E2-Crimson, mPlum, Dendra2, Timer, and PAmCherry.

* * * * *